United States Patent
Matray et al.

(10) Patent No.: US 9,765,220 B2
(45) Date of Patent: Sep. 19, 2017

(54) WATER SOLUBLE FLUORESCENT OR COLORED DYES AND METHODS FOR THEIR USE

(71) Applicants: Sony Corporation, Tokyo (JP); Sony Corporation of America, New York, NY (US)

(72) Inventors: Tracy Matray, Snohomish, WA (US); Hesham Sherif, Redmond, WA (US); C. Frederick Battrell, Wenatchee, WA (US)

(73) Assignees: SONY CORPORATION, Minato-ku, Tokyo (JP); SONY CORPORATION OF AMERICA, New York, NY (US)

( * ) Notice: Subject to any disclaimer, the term of this patent is extended or adjusted under 35 U.S.C. 154(b) by 0 days.

(21) Appl. No.: 14/913,675

(22) PCT Filed: Aug. 22, 2014

(86) PCT No.: PCT/US2014/052331
§ 371 (c)(1),
(2) Date: Feb. 22, 2016

(87) PCT Pub. No.: WO2015/027176
PCT Pub. Date: Feb. 26, 2015

(65) Prior Publication Data
US 2016/0208100 A1    Jul. 21, 2016

Related U.S. Application Data

(60) Provisional application No. 61/868,973, filed on Aug. 22, 2013.

(51) Int. Cl.

| | | |
|---|---|---|
| C09B 3/14 | (2006.01) | |
| C09B 1/00 | (2006.01) | |
| C07H 21/04 | (2006.01) | |
| C09B 5/62 | (2006.01) | |
| C09B 11/24 | (2006.01) | |
| C09B 57/00 | (2006.01) | |
| C09B 57/08 | (2006.01) | |
| C09B 69/10 | (2006.01) | |
| C07F 9/09 | (2006.01) | |
| C07F 9/576 | (2006.01) | |
| C07F 9/655 | (2006.01) | |
| G01N 33/58 | (2006.01) | |

(52) U.S. Cl.
CPC ............... *C09B 3/14* (2013.01); *C07F 9/094* (2013.01); *C07F 9/098* (2013.01); *C07F 9/5765* (2013.01); *C07F 9/65522* (2013.01); *C07H 21/04* (2013.01); *C09B 1/00* (2013.01); *C09B 5/62* (2013.01); *C09B 11/24* (2013.01); *C09B 57/001* (2013.01); *C09B 57/08* (2013.01); *C09B 69/103* (2013.01); *C09B 69/109* (2013.01); *G01N 33/582* (2013.01); *G01N 33/583* (2013.01)

(58) Field of Classification Search
None
See application file for complete search history.

(56) References Cited

U.S. PATENT DOCUMENTS

| 5,268,486 A | 12/1993 | Waggoner et al. |
|---|---|---|
| 5,318,894 A | 6/1994 | Pugia |
| 6,140,480 A | 10/2000 | Kool |
| 6,218,108 B1 | 4/2001 | Kool |
| 6,479,650 B1 | 11/2002 | Kool |
| 6,670,193 B2 | 12/2003 | Kool |
| 7,172,907 B2 | 2/2007 | Chen et al. |
| 7,423,133 B2 | 9/2008 | Kool et al. |
| 8,217,389 B2 | 7/2012 | Nakano et al. |
| 2003/0207208 A1 | 11/2003 | Uenishi |
| 2004/0014981 A1 | 1/2004 | Lugade et al. |

(Continued)

FOREIGN PATENT DOCUMENTS

| WO | 01/69254 A2 | 9/2001 |
|---|---|---|
| WO | 02/36832 A2 | 5/2002 |

(Continued)

OTHER PUBLICATIONS

Matray et al., "Water Soluble Fluorescent or Colored Dyes and Methods for Their Use," U.S. Appl. No. 15/112,395, filed Jul. 18, 2016, 73 pages.
PubChem, "US20100012929A1-20100121-C00010_4," SID No. 140452858, retrieved Mar. 29, 2016 from URL https://pubchem.ncbi.nlm.nih.gov/substance/140452858, 6 pages.
Arian et al., "1,9-Dialkoxyanthracene as a $^1O_2$-Sensitive Linker," *J. Am. Chem. Soc.* 133:3972-3980, 2011.
Lee et al., "Monitoring the Hydrophobic Interactions of Internally Pyrene-Labeled Poly(ethylene oxide)s in Water by Fluorescence Spectroscopy," *Macromolecules* 31:9193-9200, 1998.

*Primary Examiner* — Timothy R Rozof
(74) *Attorney, Agent, or Firm* — Seed IP Law Group LLP

(57) ABSTRACT

Compounds useful as fluorescent or colored dyes are disclosed. The compounds have the following structure (I): including stereoisomers, salts and tautomers thereof, wherein $R^1$, $R^2$, $R^3$, $L^1$, $L^2$, $L^3$, $L^4$, $L^5$, $L^6$, $M^1$, $M^2$, A, q, w and n are as defined herein. Methods associated with preparation and use of such compounds are also provided.

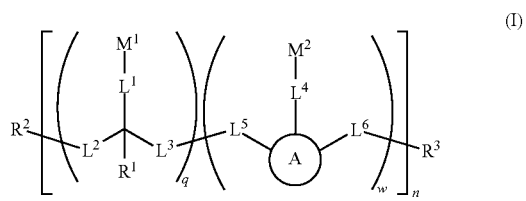

27 Claims, No Drawings

(56) References Cited

U.S. PATENT DOCUMENTS

| | | |
|---|---|---|
| 2004/0138467 A1 | 7/2004 | French et al. |
| 2004/0224372 A1 | 11/2004 | Li et al. |
| 2005/0123935 A1 | 6/2005 | Haugland et al. |
| 2007/0042398 A1 | 2/2007 | Peng et al. |
| 2007/0077549 A1 | 4/2007 | Buller et al. |
| 2008/0227939 A1 | 9/2008 | Mizoshita et al. |
| 2009/0299070 A1 | 12/2009 | Berens et al. |
| 2010/0039684 A1 | 2/2010 | Kolb et al. |
| 2012/0116079 A1 | 5/2012 | Lukhtanov et al. |
| 2012/0126175 A1* | 5/2012 | Ueno ............... C09B 1/00 252/301.16 |
| 2013/0102021 A1 | 4/2013 | Beacham et al. |
| 2013/0119363 A1 | 5/2013 | Sasaki et al. |
| 2013/0244891 A1 | 9/2013 | Waggoner et al. |
| 2016/0341736 A1 | 11/2016 | Matray et al. |

FOREIGN PATENT DOCUMENTS

| | | |
|---|---|---|
| WO | 2006/099050 A2 | 9/2006 |
| WO | 2010/026957 A1 | 3/2010 |
| WO | 2014/147642 A1 | 9/2014 |
| WO | 2015/027176 A1 | 2/2015 |

* cited by examiner

WATER SOLUBLE FLUORESCENT OR COLORED DYES AND METHODS FOR THEIR USE

BACKGROUND OF THE INVENTION

Field

The present invention is directed to novel fluorescent or colored dyes and methods for their preparation and use in various analytical methods.

Description of the Related Art

Fluorescent and/or colored dyes are known to be particularly suitable for applications in which a highly sensitive detection reagent is desirable. Dyes that are able to preferentially label a specific ingredient or component in a sample enable the researcher to determine the presence, quantity and/or location of that specific ingredient or component. In addition, specific systems can be monitored with respect to their spatial and temporal distribution in diverse environments.

Fluorescence and colorimetric methods are extremely widespread in chemistry and biology. These methods give useful information on the presence, structure, distance, orientation, complexation and/or location for biomolecules. In addition, time-resolved methods are increasingly used in measurements of dynamics and kinetics. As a result, many strategies for fluorescence or color labeling of biomolecules, such as nucleic acids and protein, have been developed.

Perylenes and related dyes have high photochemical persistency (chemical, thermal, and photochemical stability) and high fluorescence quanta yield and are used in a variety of reprographic processes, solar cells, photovoltaic devices, and dye lasers. However, perylene derivatives have been used primarily as pigments and fluorescent dyes. Perylene dyes of various colors and light-absorbing properties have been reported. For example, Becker S. et al, Chem. Eur. J., 6,213,984, (2000), report the synthesis of thermotropic perylenedicarboximide chromophores that show a color change from blue to orange. Perylene and related chromophores have seen limited use as biomolecular probes, apparently due to the strongly hydrophobic character of these types of molecules and difficulties with regiospecific labeling of biomolecules with the same.

There is thus a need in the art for water soluble dyes and biomarkers that permit visual or fluorescent detection of biomolecules without prior illumination or chemical or enzymatic activation. Ideally, such dyes and biomarkers should be intensely colored or fluorescent and should be available in a variety of colors and fluorescent wavelengths. The present invention fulfills this need and provides further related advantages.

BRIEF SUMMARY

In brief, the present invention is generally directed to compounds useful as water soluble, fluorescent or colored dyes and probes that enable visual detection of biomolecules and other analytes, as well as reagents for their preparation. Methods for visually detecting a biomolecule and for determining the size of a biomolecule are also described. The water soluble, fluorescent or colored dyes of the invention are intensely colored and/or fluorescent and can be readily observed by visual inspection or other means. In some embodiments the compounds may be observed without prior illumination or chemical or enzymatic activation. By appropriate selection of the dye, as described herein, visually detectable biomolecules of a variety of colors may be obtained.

In one embodiment, compounds having the following structure (I) are provided:

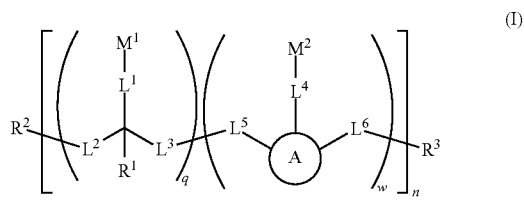

or a stereoisomer, tautomer or salt thereof, wherein $R^1$, $R^2$, $R^3$, $L^1$, $L^2$, $L^3$, $L^4$, $L^5$, $L^6$, $M^1$, $M^2$, A, q, w and n are as defined herein.

In another embodiment, a method for staining a sample is provided, the method comprises adding to said sample a representative compound as described herein in an amount sufficient to produce an optical response when said sample is illuminated at an appropriate wavelength.

In still other embodiments, the present disclosure provides a method for visually detecting a biomolecule, comprising:

(a) providing a representative compound described herein; and (b) detecting the compound by its visible properties.

Other disclosed methods include a method for visually detecting a biomolecule, the method comprising:

(a) admixing any of the disclosed compounds with one or more biomolecules; and (b) detecting the compound by its visible properties.

Other embodiments are directed to a composition comprising any one of the disclosed compounds and one or more biomolecules. Use of such composition in analytical methods for detection of the one or more biomolecules is also provided.

These and other aspects of the invention will be apparent upon reference to the following detailed description.

DETAILED DESCRIPTION OF THE INVENTION

In the following description, certain specific details are set forth in order to provide a thorough understanding of various embodiments of the invention. However, one skilled in the art will understand that the invention may be practiced without these details.

Unless the context requires otherwise, throughout the present specification and claims, the word "comprise" and variations thereof, such as, "comprises" and "comprising" are to be construed in an open, inclusive sense, that is, as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

"Amino" refers to the —$NH_2$ group.

"Carboxy" refers to the —$CO_2H$ group.

"Cyano" refers to the —CN group.

"Formyl" refers to the —C(=O)H group.

"Hydroxy" or "hydroxyl" refers to the —OH group.

"Imino" refers to the =NH group.

"Nitro" refers to the —NO$_2$ group.

"Oxo" refers to the =O substituent group.

"Sulfhydryl" refers to the —SH group.

"Thioxo" refers to the =S group.

"Alkyl" refers to a straight or branched hydrocarbon chain group consisting solely of carbon and hydrogen atoms, which is saturated or unsaturated (i.e., contains one or more double and/or triple bonds), having from one to twelve carbon atoms (C$_1$-C$_{12}$ alkyl), preferably one to eight carbon atoms (C$_1$-C$_8$ alkyl) or one to six carbon atoms (C$_1$-C$_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. Unless stated otherwise specifically in the specification, an alkyl group may be optionally substituted.

"Alkylene" or "alkylene chain" refers to a straight or branched divalent hydrocarbon chain linking the rest of the molecule to a substituent group, consisting solely of carbon and hydrogen, which is saturated or unsaturated (i.e., contains one or more double and/or triple bonds), and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the substituent group through a single or double bond. The points of attachment of the alkylene chain to the rest of the molecule and to the substituent group can be through one carbon or any two carbons within the chain. Unless stated otherwise specifically in the specification, an alkylene chain may be optionally substituted.

"Alkoxy" refers to a group of the formula —OR$_a$ where R$_a$ is an alkyl group as defined above containing one to twelve carbon atoms. Unless stated otherwise specifically in the specification, an alkoxy group may be optionally substituted.

"Alkylamino" refers to a group of the formula —NHR$_a$ or —NR$_a$R$_a$ where each R$_a$ is, independently, an alkyl group as defined above containing one to twelve carbon atoms. Unless stated otherwise specifically in the specification, an alkylamino group may be optionally substituted.

"Alkylether" refers to any alkyl group as defined above, wherein at least one carbon-carbon bond is replaced with a carbon-oxygen bond. The carbon-oxygen bond may be on the terminal end (as in an alkoxy group) or the carbon oxygen bond may be internal (i.e., C—O—C). Alkylethers include at least one carbon oxygen bond, but may include more than one. For example, polyethylene glycol (PEG) is included within the meaning of alkylether. Unless stated otherwise specifically in the specification, an alkylether group may be optionally substituted. For example, in some embodiments and alkylether is substituted with an alcohol or phosphate.

"Alkylenether" refers to any alkylene group as defined above, wherein at least one carbon-carbon bond is replaced with a carbon-oxygen bond. The carbon-oxygen bond may be on the terminal end (as in an alkoxy group) or the carbon oxygen bond may be internal (i.e., C—O—C). Alkylenethers include at least one carbon oxygen bond, but may include more than one. For example, polyethylene glycol (PEG) is included within the meaning of alkylenether. Unless stated otherwise specifically in the specification, an alkylenether group may be optionally substituted.

"Alkylphospho" refers to the —RP(=O)(R$_a$)R$_b$ group, wherein R is an alkylene group, R$_a$ is OH, O$^-$ or OR$_c$; and R$_b$ is —Oalkyl or —Oalkylether, wherein R$_c$ is a counter ion (e.g., Na+ and the like). Unless stated otherwise specifically in the specification, an alkylphospho group may be optionally substituted. For example, in certain embodiments, the —Oalkyl or —Oalkylether moiety (R$_b$) in a alkylphospho group is optionally substituted with one or more of hydroxyl, amino, sulfhydryl, phosphate, thiophosphate, phosphoalkyl, thiophosphoalkyl, phosphoalkylether or thiophosphoalkylether. "Oalkylphospho is an alkylphospho group connected to the remainder of the molecule via an oxygen atom. Unless stated otherwise specifically in the specification, an Oalkylphospho group may be optionally substituted.

"Alkyetherphospho" refers to the —RP(=O)(R$_a$)R$_b$ group, wherein R is an alkylenether group, R$_a$ is OH, O$^-$ or OR$_c$; and R$_b$ is —Oalkyl or —Oalkylether, wherein R$_c$ is a counter ion (e.g., Na+ and the like). Unless stated otherwise specifically in the specification, an alkyletherphopsho group may be optionally substituted. For example, in certain embodiments, the —Oalkyl or —Oalkylether moiety (R$_b$) in an alkyletherphospho group is optionally substituted with one or more of hydroxyl, amino, sulfhydryl, phosphate, thiophosphate, phosphoalkyl, thiophosphoalkyl, phosphoalkylether or thiophosphoalkylether. "Oalkyletherphospho is an alkyletherphospho group connected to the remainder of the molecule via an oxygen atom. Unless stated otherwise specifically in the specification, an Oalkyletherphospho group may be optionally substituted.

"Alkylthiophospho" refers to the —P(=R$_a$)(R$_b$)R$_c$ group, wherein R$_a$ is O or S, R$_b$ is OH, O$^-$, S$^-$, OR$_d$ or SR$_d$; and R$_c$ is —Oalkyl or —Oalkylether, wherein R$_d$ is a counter ion (e.g., Na+ and the like) and provided that: R$_a$ is S or R$_b$ is S$^-$ or SR$_d$; or provided that R$_a$ is S and R$_b$ is S$^-$ or SR$_d$. Unless stated otherwise specifically in the specification, a alkylthiophospho group may be optionally substituted. For example, in certain embodiments, the —Oalkyl or —Oalkylether moiety in a alkythiophospho group is optionally substituted with one or more of hydroxyl, amino, sulfhydryl, phosphate, thiophosphate, phosphoalkyl, thiophosphoalkyl, phosphoalkylether or thiophosphoalkylether. "Oalkylthiophospho is a alkylthiophospho group connected to the remainder of the molecule via an oxygen atom. Unless stated otherwise specifically in the specification, an Oalkylthiophospho group may be optionally substituted.

"Alkyletherthiophospho" refers to the —P(=R$_a$)(R$_b$)R$_c$ group, wherein R$_a$ is O or S, R$_b$ is OH, O$^-$, S$^-$, OR$_d$ or SR$_d$; and R$_c$ is —Oalkyl or —Oalkylether, wherein R$_d$ is a counter ion (e.g., Na+ and the like) and provided that: R$_a$ is S or R$_b$ is S$^-$ or SR$_d$; or provided that R$_a$ is S and R$_b$ is S$^-$ or SR$_d$. Unless stated otherwise specifically in the specification, an alkyletherthiophospho group may be optionally substituted. For example, in certain embodiments, the —Oalkyl or —Oalkylether moiety in a alkyletherthiophospho group is optionally substituted with one or more of hydroxyl, amino, sulfhydryl, phosphate, thiophosphate, phosphoalkyl, thiophosphoalkyl, phosphoalkylether or thiophosphoalkylether. "Oalkyletherthiophospho is an alkyletherthiophospho group connected to the remainder of the molecule via an oxygen atom. Unless stated otherwise specifically in the specification, an Oalkyletherthiophospho group may be optionally substituted.

"Amide" refers to the —NR$_a$R$_b$ radical, wherein R$_a$ and R$_b$ are independently H, alkyl or aryl. Unless stated otherwise specifically in the specification, an amide group may be optionally substituted.

"Aryl" refers to a hydrocarbon ring system group comprising hydrogen, 6 to 18 carbon atoms and at least one aromatic ring. For purposes of this invention, the aryl group may be a monocyclic, bicyclic, tricyclic or tetracyclic ring system, which may include fused or bridged ring systems. Aryl groups include, but are not limited to, aryl groups derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl groups that are optionally substituted.

"Aryloxy" refers to a group of the formula —OR$_a$, where R$_a$ is an aryl moiety as defined above, for example phenoxy and the like. Unless stated otherwise specifically in the specification, an aryloxy group may be optionally substituted.

"Aralkyl" refers to a group of the formula —R$_b$—R$_c$ where R$_b$ is an alkylene chain as defined above and R$_c$ is one or more aryl groups as defined above, for example, benzyl, diphenylmethyl and the like. Unless stated otherwise specifically in the specification, an aralkyl group may be optionally substituted.

"Oaralkyl" is an aralkyl group which is connected to the remainder of the molecule via an oxygen linkage. "ODMT" refers to dimethoxytrityl linked to the rest of the molecule via an O atom. Unless stated otherwise specifically in the specification, an Oaralkyl group may be optionally substituted.

"Cyanoalkyl" refers to an alkyl group comprising at least one cyano substituent. The one or more —CN substituents may be on a primary, secondary or tertiary carbon atom. Unless stated otherwise specifically in the specification, a cyanoalkyl group may be optionally substituted.

"Cycloalkyl" or "carbocyclic ring" refers to a stable non-aromatic monocyclic or polycyclic hydrocarbon group consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic cycloalkyl groups include, for example, cyclopropyl, cyclobutyl, cyclopentyl, cyclohexyl, cycloheptyl, and cyclooctyl. Polycyclic cycloalkyl groups include, for example, adamantyl, norbornyl, decalinyl, 7,7-dimethyl-bicyclo[2.2.1]heptanyl, and the like. Unless otherwise stated specifically in the specification, a cycloalkyl group may be optionally substituted.

"Cycloalkylalkyl" refers to a group of the formula —R$_b$R$_d$ where R$_b$ is an alkylene chain as defined above and R$_d$ is a cycloalkyl group as defined above. Unless stated otherwise specifically in the specification, a cycloalkylalkyl group may be optionally substituted.

"Multicyclic" refers to any molecule having more than one ring. The rings may be either, fused, spirocyclic or separated by one or more atoms (e.g., linked via an acyclic linker).

"Spirocyclic" refers to a multicyclic molecule wherein two rings share a single carbon atom.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl group, as defined above, that is substituted by one or more halo groups, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Heterocyclyl" or "heterocyclic ring" refers to a stable 3- to 18-membered non-aromatic ring group which consists of two to twelve carbon atoms and from one to six heteroatoms selected from the group consisting of nitrogen, oxygen and sulfur. Unless stated otherwise specifically in the specification, the heterocyclyl group may be a monocyclic, bicyclic, tricyclic or tetracyclic ring system, which may include fused or bridged ring systems; and the nitrogen, carbon or sulfur atoms in the heterocyclyl group may be optionally oxidized; the nitrogen atom may be optionally quaternized; and the heterocyclyl group may be partially or fully saturated. Examples of such heterocyclyl groups include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, Unless stated otherwise specifically in the specification, a heterocyclyl group may be optionally substituted.

"N-heterocyclyl" refers to a heterocyclyl group as defined above containing at least one nitrogen and where the point of attachment of the heterocyclyl group to the rest of the molecule is through a nitrogen atom in the heterocyclyl group. Unless stated otherwise specifically in the specification, a N-heterocyclyl group may be optionally substituted.

"Heterocyclylalkyl" refers to a group of the formula —R$_b$R$_e$ where R$_b$ is an alkylene chain as defined above and R$_e$ is a heterocyclyl group as defined above, and if the heterocyclyl is a nitrogen-containing heterocyclyl, the heterocyclyl may be attached to the alkyl group at the nitrogen atom. Unless stated otherwise specifically in the specification, a heterocyclylalkyl group may be optionally substituted.

"Heteroaryl" refers to a 5- to 14-membered ring system group comprising hydrogen atoms, one to thirteen carbon atoms, one to six heteroatoms selected from the group consisting of nitrogen, oxygen and sulfur, and at least one aromatic ring. For purposes of this invention, the heteroaryl group may be a monocyclic, bicyclic, tricyclic or tetracyclic ring system, which may include fused or bridged ring systems; and the nitrogen, carbon or sulfur atoms in the heteroaryl group may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group may be optionally substituted.

"N-heteroaryl" refers to a heteroaryl group as defined above containing at least one nitrogen and where the point of attachment of the heteroaryl group to the rest of the molecule is through a nitrogen atom in the heteroaryl group. Unless stated otherwise specifically in the specification, an N-heteroaryl group may be optionally substituted.

"Heteroarylalkyl" refers to a group of the formula —$R_b R_f$ where $R_b$ is an alkylene chain as defined above and $R_f$ is a heteroaryl group as defined above. Unless stated otherwise specifically in the specification, a heteroarylalkyl group may be optionally substituted.

"Hydroxylalkyl" refers to an alkyl group comprising at least one hydroxyl substituent. The one or more —OH substituents may be on a primary, secondary or tertiary carbon atom. Unless stated otherwise specifically in the specification, hydroxyalkyl group may be optionally substituted.

"Hydroxylalkylether" refers to an alkylether group comprising at least one hydroxyl substituent. The one or more —OH substituents may be on a primary, secondary or tertiary carbon atom. Unless stated otherwise specifically in the specification, hydroxyalkylether group may be optionally substituted.

"Phosphate" refers to the —OP(=O)($R_a$)$R_b$ group, wherein $R_a$ is OH, O⁻ or OR$_c$; and $R_b$ is OH, O⁻, OR$_c$, a further phosphate group (as in diphosphate and triphosphate) thiophosphate, phosphoalkyl, thiophosphoalkyl, phosphoalkylether or thiophosphoalkylether, wherein $R_c$ is a counter ion (e.g., Na+ and the like). Unless stated otherwise specifically in the specification, a phosphate group may be optionally substituted.

"Phospho" refers to the —P(=O)($R_a$)$R_b$ group, wherein $R_a$ is OH, O⁻ or OR$_c$; and $R_b$ is OH, O⁻, OR$_c$, a phosphate group (as in diphosphate and triphosphate) thiophosphate, phosphoalkyl, thiophosphoalkyl, phosphoalkylether or thiophosphoalkylether, wherein $R_c$ is a counter ion (e.g., Na+ and the like). Unless stated otherwise specifically in the specification, a phospho group may be optionally substituted.

"Phosphoalkyl" refers to the —P(=O)($R_a$)$R_b$ group, wherein $R_a$ is OH, O⁻ or OR$_c$; and $R_b$ is —Oalkyl, wherein $R_c$ is a counter ion (e.g., Na+ and the like). Unless stated otherwise specifically in the specification, a phosphoalkyl group may be optionally substituted. For example, in certain embodiments, the —Oalkyl moiety in a phosphoalkyl group is optionally substituted with one or more of hydroxyl, amino, sulfhydryl or a phosphate, thiophosphate, phosphoalkyl, thiophosphoalkyl, phosphoalkylether or thiophosphoalkylether. "Ophosphoalkyl is a phosphoalkyl group connected to the remainder of the molecule via an oxygen atom. Unless stated otherwise specifically in the specification, an ophosphoalkyl group may be optionally substituted.

"Phosphoalkylether" refers to the —P(=O)($R_a$)$R_b$ group, wherein $R_a$ is OH, O⁻ or OR$_c$; and $R_b$ is —Oalkylether, wherein $R_c$ is a counter ion (e.g., Na+ and the like). Unless stated otherwise specifically in the specification, a phosphoalkylether group may be optionally substituted. For example, in certain embodiments, the —Oalkylether moiety in a phosphoalkylether group is optionally substituted with one or more of hydroxyl, amino, sulfhydryl, phosphate, thiophosphate, phosphoalkyl, thiophosphoalkyl, phosphoalkylether or thiophosphoalkylether. "Ophosphoalkylether is a phosphoalkylether group connected to the remainder of the molecule via an oxygen atom. Unless stated otherwise specifically in the specification, an ophosphoalkylether group may be optionally substituted.

"Sulfhydrylalkyl" refers to an alkyl group comprising at least one sulfhydryl substituent. The one or more —SH substituents may be on a primary, secondary or tertiary carbon atom. Unless stated otherwise specifically in the specification, a sulfhydrylalkyl group may be optionally substituted.

"Sulfhydrylalkylether" refers to an alkylether group comprising at least one sulfhydryl substituent. The one or more —SH substituents may be on a primary, secondary or tertiary carbon atom. Unless stated otherwise specifically in the specification, a sulfhydrylalkylether group may be optionally substituted.

"Sulfonate" refers to the —OS(O)$_2$$R_a$ group, wherein $R_a$ is alkyl or aryl. Unless stated otherwise specifically in the specification, a sulfonate group may be optionally substituted.

"Thioalkyl" refers to a group of the formula —SR$_a$ where $R_a$ is an alkyl group as defined above containing one to twelve carbon atoms. Unless stated otherwise specifically in the specification, a thioalkyl group may be optionally substituted.

"Thiophosphate" refers to the —OP(=$R_a$)($R_b$)$R_c$ group, wherein $R_a$ is O or S, $R_b$ is OH, O⁻, S⁻, OR$_d$ or SR$_d$; and $R_c$ is OH, O⁻, OR$_d$, phosphate group thiophosphate, phosphoalkyl, thiophosphoalkyl, phosphoalkylether or thiophosphoalkylether, wherein $R_d$ is a counter ion (e.g., Na+ and the like) and provided that: $R_a$ is S or $R_b$ is S⁻ or SR$_d$; or provided that $R_a$ is S and $R_b$ is S⁻ or SR$_d$. Unless stated otherwise specifically in the specification, a thiophosphate group may be optionally substituted.

"Thiophospho" refers to the —OP(=$R_a$)($R_b$)$R_c$ group, wherein $R_a$ is O or S, $R_b$ is OH, O⁻, S⁻, OR$_d$ or SR$_d$; and $R_c$ is OH, O⁻, OR$_d$, a phosphate group, thiophosphate, phosphoalkyl, thiophosphoalkyl, phosphoalkylether or thiophosphoalkylether, wherein $R_d$ is a counter ion (e.g., Na+ and the like) and provided that: $R_a$ is S or $R_b$ is S⁻ or SR$_d$; or provided that $R_a$ is S and $R_b$ is S⁻ or SR$_d$. Unless stated otherwise specifically in the specification, a thiophospho group may be optionally substituted.

"Thiophosphoalkyl" refers to the —P(=$R_a$)($R_b$)$R_c$ group, wherein $R_a$ is O or S, $R_b$ is OH, O⁻, S⁻, OR$_d$ or SR$_d$; and $R_c$ is —Oalkyl, wherein $R_d$ is a counter ion (e.g., Na+ and the like) and provided that: $R_a$ is S or $R_b$ is S⁻ or SR$_d$; or provided that $R_a$ is S and $R_b$ is S⁻ or SR$_d$. Unless stated otherwise specifically in the specification, a thiophosphoalkyl group may be optionally substituted. For example, in certain embodiments, the —Oalkyl moiety in a thiophosphoalkyl group is optionally substituted with one or more of hydroxyl, amino, sulfhydryl, phosphate, thiophosphate, phosphoalkyl, thiophosphoalkyl, phosphoalkylether or thiophosphoalkylether. "Othiophosphoalkyl is a thiophosphoalkyl group connected to the remainder of the molecule via an oxygen atom. Unless stated otherwise specifically in the specification, an Othiophosphoalkyl group may be optionally substituted.

"Thiophosphoalkylether" refers to the —P(=$R_a$)($R_b$)$R_c$ group, wherein $R_a$ is O or S, $R_b$ is OH, O⁻, S⁻, $OR_d$ or $SR_d$; and $R_c$ is —Oalkylether, wherein $R_d$ is a counter ion (e.g., Na+ and the like) and provided that: $R_a$ is S or $R_b$ is S⁻ or $SR_d$; or provided that $R_a$ is S and $R_b$ is S⁻ or $SR_d$. Unless stated otherwise specifically in the specification, a thiophosphoalkylether group may be optionally substituted. For example, in certain embodiments, the —Oalkylether moiety in a thiophosphoalkyl group is optionally substituted with one or more of hydroxyl, amino, sulfhydryl, phosphate, thiophosphate, phosphoalkyl, thiophosphoalkyl, phosphoalkylether or thiophosphoalkylether. "Othiophosphoalkylether is a thiophosphoalkylether group connected to the remainder of the molecule via an oxygen atom. Unless stated otherwise specifically in the specification, an Othiophosphoalkylether group may be optionally substituted.

The term "substituted" used herein means any of the above groups (i.e., alkyl, alkylene, alkoxy, alkylamino, alkylether, alkylenether, amide, thioalkyl, aryl, aryloxy, aralkyl, Oaralkyl, cyanoalkyl, cycloalkyl, cycloalkylalkyl, haloalkyl, heterocyclyl, N-heterocyclyl, heterocyclylalkyl, heteroaryl, N-heteroaryl, heteroarylalkyl, hydroxylalkyl, aminoalkyl, hydroxylalkylether, phosphate, phosphoalkyl, phosphoalkylether, sulfhydrylalkyl, sulfhydrylalkylether, sulfonate, thiophosphate, thiophosphoalkyl and/or thiophosphoalkylether) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC(=O)R_h$, —$NR_gC(=O)$ $NR_gR_h$, —$NR_gC(=O)OR_h$, —$NR_gSO_2R_h$, —OC(=O) $NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted also means any of the above groups in which one or more hydrogen atoms are replaced with —C(=O)$R_g$, —C(=O) $OR_g$, —C(=O)$NR_gR_h$, —$CH_2SO_2R_g$, —$CH_2SO_2NR_gR_h$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In addition, each of the foregoing substituents may also be optionally substituted with one or more of the above substituents.

"Conjugation" refers to the overlap of one p-orbital with another p-orbital across an intervening sigma bond. Conjugation may occur in cyclic or acyclic compounds. A "degree of conjugation" refers to the overlap of at least one p-orbital with another p-orbital across an intervening double bond. For example, 1,3-butadine has one degree of conjugation, while benzene and other aromatic compounds typically have multiple degrees of conjugation. Fluorescent and colored compounds typically comprise at least one degree of conjugation.

"Fluorescent" refers to a molecule which is capable of absorbing light of a particular frequency and emitting light of a different frequency. Fluorescence is well-known to those of ordinary skill in the art.

"Colored" refers to a molecule which absorbs light within the colored spectrum (i.e., red, yellow, blue and the like).

A "linker" refers to a contiguous chain of at least one atom, such as carbon, oxygen, nitrogen, sulfur, phosphorous and combinations thereof, which connects a portion of a molecule to another portion of the same molecule or to a different molecule, moiety or solid support (e.g., microparticle). Linkers may connect the molecule via a covalent bond or other means, such as ionic or hydrogen bond interactions.

For purposes of the present invention, the term "biomolecule" refers to any of a variety of biological materials, including nucleic acids, carbohydrates, amino acids, polypeptides, glycoproteins, hormones, aptamers and mixtures thereof. More specifically, the term is intended to include, without limitation, RNA, DNA, oligonucleotides, modified or derivatized nucleotides, enzymes, receptors, prions, receptor ligands (including hormones), antibodies, antigens, and toxins, as well as bacteria, viruses, blood cells, and tissue cells. The visually detectable biomolecules of the invention (i.e., compounds of structure (I) having a biomolecule linked thereto) are prepared, as further described herein, by contacting a biomolecule with a compound having a reactive group that enables attachment of the biomolecule to the compound via any available atom or functional group, such as an amino, hydroxy, carboxyl, or sulfhydryl group on the biomolecule.

The terms "visible" and "visually detectable" are used herein to refer to substances that are observable by visual inspection, without prior illumination, or chemical or enzymatic activation. Such visually detectable substances absorb and emit light in a region of the spectrum ranging from about 300 to about 900 nm. Preferably, such substances are intensely colored, preferably having a molar extinction coefficient of at least about 40,000, more preferably at least about 50,000, still more preferably at least about 60,000, yet still more preferably at least about 70,000, and most preferably at least about 80,000 $M^{-1}$ $cm^{-1}$. The biomolecules of the invention may be detected by observation with the naked eye, or with the aid of a optically based detection device, including, without limitation, absorption spectrophotometers, transmission light microscopes, digital cameras and scanners. Visually detectable substances are not limited to those which emit and/or absorb light in the visible spectrum. Substances which emit and/or absorb light in the ultraviolet (UV) region (about 10 nm to about 400 nm), infrared (IR) region (about 700 nm to about 1 mm), and substances emitting and/or absorbing in other regions of the electromagnetic spectrum are also included with the scope of "visually detectable" substances.

For purposes of the invention, the term "photostable visible dye" refers to a chemical moiety that is visually detectable, as defined hereinabove, and is not significantly altered or decomposed upon exposure to light. Preferably, the photostable visible dye does not exhibit significant bleaching or decomposition after being exposed to light for at least one hour. More preferably, the visible dye is stable after exposure to light for at least 12 hours, still more preferably at least 24 hours, still yet more preferably at least one week, and most preferably at least one month. Nonlimiting examples of photostable visible dyes suitable for use in the compounds and methods of the invention include azo dyes, thioindigo dyes, quinacridone pigments, dioxazine, phthalocyanine, perinone, diketopyrrolopyrrole, quinophthalone, and truarycarbonium.

As used herein, the term "perylene derivative" is intended to include any substituted perylene that is visually detectable. However, the term is not intended to include perylene itself. The terms "anthracene derivative", "naphthalene derivative", and "pyrene derivative" are used analogously. In some preferred embodiments, a derivative (e.g., perylene, pyrene, anthracene or naphthalene derivative) is an imide, bisimide or hydrazamimide derivative of perylene, anthracene, naphthalene, or pyrene.

The visually detectable biomolecules of the invention are useful for a wide variety of biochemical and biomedical applications in which there is a need to determine the presence, location, or quantity of a particular biomolecule. In another aspect, therefore, the invention provides a method for visually detecting a biomolecule, comprising: (a) providing a biological system with a visually detectable biomolecule comprising the compound of structure (I) linked to a biomolecule; and (b) detecting the biomolecule by its visible properties. For purposes of the invention, the phrase "detecting the biomolecule by its visible properties" means that the biomolecule, without illumination or chemical or enzymatic activation, is observed with the naked eye, or with the aid of a optically based detection device, including, without limitation, absorption spectrophotometers, transmission light microscopes, digital cameras and scanners. A densitometer may be used to quantify the amount of visually detectable biomolecule present. For example, the relative quantity of the biomolecule in two samples can be determined by measuring relative optical density. If the stoichiometry of dye molecules per biomolecule is known, and the extinction coefficient of the dye molecule is known, then the absolute concentration of the biomolecule can also be determined from a measurement of optical density. As used herein, the term "biological system" is used to refer to any solution or mixture comprising one or more biomolecules in addition to the visually detectable biomolecule. Nonlimiting examples of such biological systems include cells, cell extracts, tissue samples, electrophoretic gels, assay mixtures, and hybridization reaction mixtures.

"Microparticle" refers to any of a number of small particles useful for attachment to compounds of the invention, including, but not limited to, glass beads, magnetic beads, polymeric beads, nonpolymeric beads, and the like. In certain embodiments, a microparticle comprises polystyrene beads.

"Base pairing moiety" refers to a heterocyclic moiety capable of hybridizing with a complementary heterocyclic moiety via hydrogen bonds (e.g., Watson-Crick base pairing). Base pairing moieties include natural and unnatural bases. Non-limiting examples of base pairing moieties are RNA and DNA bases such adenosine, guanosine, thymidine, cytosine and uridine and analogues thereof.

The invention disclosed herein is also meant to encompass all compounds of structure (I) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$ and $^{125}I$, respectively.

Isotopically-labeled compounds of structure (I) can generally be prepared by conventional techniques known to those skilled in the art or by processes analogous to those described below and in the following Examples using an appropriate isotopically-labeled reagent in place of the non-labeled reagent previously employed.

"Stable compound" and "stable structure" are meant to indicate a compound that is sufficiently robust to survive isolation to a useful degree of purity from a reaction mixture, and formulation into an efficacious therapeutic agent.

"Optional" or "optionally" means that the subsequently described event or circumstances may or may not occur, and that the description includes instances where said event or circumstance occurs and instances in which it does not. For example, "optionally substituted alkyl" means that the alkyl group may or may not be substituted and that the description includes both substituted alkyl groups and alkyl groups having no substitution.

"Salt" includes both acid and base addition salts.

"Acid addition salt" refers to those salts which are formed with inorganic acids such as, but not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Base addition salt" refers to those salts which are prepared from addition of an inorganic base or an organic base to the free acid. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. The present invention includes all solvates of the described compounds. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compounds of the invention may be true solvates, while in other cases the compounds of the invention may merely retain adventitious water or another solvent or be a mixture of water plus some adventitious solvent.

The compounds of the invention, or their salts, tautomers or solvates may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds. Various tautomeric forms of the compounds are easily derivable by those of ordinary skill in the art.

The chemical naming protocol and structure diagrams used herein are a modified form of the I.U.P.A.C. nomenclature system, using the ACD/Name Version 9.07 software program and/or ChemDraw Version 10.0 software naming program (CambridgeSoft). Common names familiar to one of ordinary skill in the art are also used.

As noted above, in one embodiment of the present invention, compounds useful as fluorescent and/or colored dyes in various analytical methods are provided. The compounds have the following structure (I):

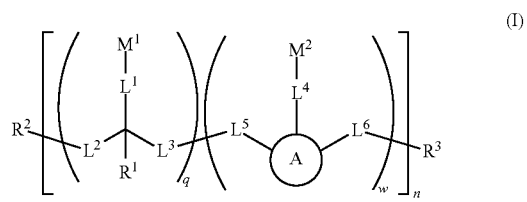

or a stereoisomer, tautomer or salt thereof, wherein:

$M^1$ and $M^2$ are, at each occurrence, independently a moiety comprising two or more double bonds and at least one degree of conjugation, and at least one occurrence of $M^1$ is a moiety comprising three or more aryl or heteroaryl rings, or combinations thereof;

A represents a cyclic moiety;

$L^1$, $L^2$, $L^3$, $L^4$, $L^5$ and $L^6$ are, at each occurrence, independently optional linkers comprising atoms selected from carbon, oxygen, sulfur, nitrogen and phosphorous;

$R^1$ is, at each occurrence, independently H, alkyl or alkoxy;

$R^2$ and $R^3$ are independently H, OH, SH, —$NH_2$, alkyl, alkylether, hydroxylalkyl, aminoalkyl, hydroxylalkylether, sulfhydrylalkyl, sulfyhdrylalkylether, cyanoalkyl, —Oaralkyl, phosphate, thiophosphate, phospho, thiophospho, alkylphospho, alkylthiophospho, —Oalkylphospho, —Oalkylthiophospho, alkyletherphospho, alkyletherthiophospho, —Oalkyletherphospho, —Oalkyletherthiophospho phosphoalkyl, phosphoalkylether, thiophosphoalkyl, thiophosphoalkylether, —Ophosphoalkyl, O-phosphoalkylether, —Othiophosphoalkyl or —Othiophosphoalkylether, or $R^2$ is a linker comprising a covalent bond to a biomolecule or microparticle, and $R^3$ is H, OH, SH, alkyl, alkylether, hydroxylalkyl, aminoalkyl, hydroxylalkylether, sulfhydrylalkyl, sulfyhdrylalkylether, cyanoalkyl, —Oaralkyl, phosphate, thiophosphate, alkylphospho, alkylthiophospho, —Oalkylphospho, —Oalkylthiophospho, alkyletherphospho, alkyletherthiophospho, —Oalkyletherphospho, —Oalkyletherthiophospho phosphoalkyl, phosphoalkylether, thiophosphoalkyl, thiophosphoalkylether, —Ophosphoalkyl, O-phosphoalkylether, —Othiophosphoalkyl or —Othiophosphoalkylether;

n is an integer from 1 to 20; and q and w are each independently 0 or 1 for each integral value of n, wherein q is 1 for at least one integral value of n.

In some embodiments, n is an integer from 1 to 10 or from 2 to 10.

In certain embodiments, $L^2$ comprises phosphorous-oxygen bonds. In other embodiments, $L^5$ comprises phosphorous-oxygen bonds.

For example, in some embodiments the compound has the following structure (III):

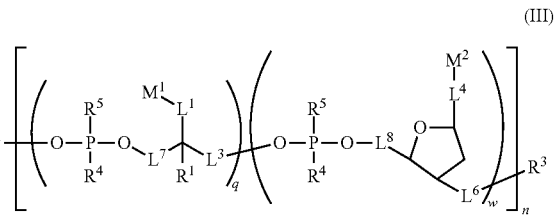

wherein:

$M^1$ and $M^2$ are, at each occurrence, independently a moiety comprising two or more double bonds and at least one degree of conjugation, and at least one occurrence of $M^1$ is a moiety comprising three or more aryl or heteroaryl rings, or combinations thereof;

$L^1$, $L^3$, $L^4$ $L^6$, $L^7$ and $L^8$ are, at each occurrence, independently optional alkylene or heteroalkylene linkers;

$R^1$ is, at each occurrence, independently H, alkyl or alkoxy;

$R^2$ is an electron pair, H, alkyl, alkylether, hydroxylalkyl, aminoalkyl, hydroxylalkylether, sulfhydrylalkyl, sulfyhdrylalkylether, cyanoalkyl, phospho, thiophospho, alkylphospho, alkylthiophospho, alkyletherphospho, alkyletherthiophospho, phosphoalkyl, phosphoalkylether, thiophosphoalkyl or thiophosphoalkylether, or $R^2$ is a linker comprising a covalent bond to a biomolecule or microparticle;

$R^3$ is H, OH, SH, —$NH_2$, alkyl, alkylether, hydroxylalkyl, aminoalkyl, hydroxylalkylether, sulfhydrylalkyl, sulfyhdrylalkylether, cyanoalkyl, —Oaralkyl, phosphate, thiophosphate, alkylphospho, alkylthiophospho, —Oalkylphospho, —Oalkylthiophospho, alkyletherphospho, alkyletherthiophospho, —Oalkyletherphospho, —Oalkyletherthiophospho phosphoalkyl, phosphoalkylether, thiophosphoalkyl, thiophosphoalkylether, —Ophosphoalkyl, O-phosphoalkylether, —Othiophosphoalkyl or —Othiophosphoalkylether;

$R^4$ is, at each occurrence, independently $O^-$, $S^-$, OZ, SZ or $N(R^6)_2$, where Z is a cation and each $R^6$ is independently H or alkyl;

$R^5$ is, at each occurrence, independently oxo, thioxo or absent;

n is an integer from 1 to 20; and q and w are each independently 0 or 1 for each integral value of n, wherein q is 1 for at least one integral value of n.

In some embodiments, the compound of structure (III) comprises at least two occurrences of the "q" unit or at least one occurrence of the "q" unit and at least one occurrence of the "w" unit. For clarity, the "q" and "w" units have the following structures:

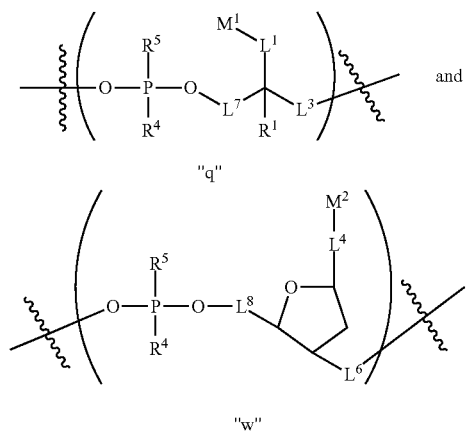

Accordingly, in some embodiments of structure (III):

n is an integer from 2 to 20, and q and w are each independently 0 or 1 for each integral value of n, wherein q is 1 for at least two integral values of n, or wherein q and w are each independently one for at least one integral value of n, which integral value may be the same or different.

In any of the foregoing embodiments, n is an integer from 2-15 or n is 2, 3, 4, 5, 6, 7, 8, 9, 10, 11, 12, 13, 14 or 15.

In some embodiments of compounds (I) or (III), w is 0 for each integral value of n. For example, in some embodiments the compound has the following structure (II):

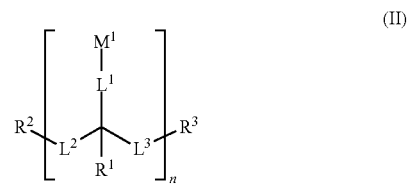

or a stereoisomer, tautomer or salt thereof, wherein:

$M^1$ is, at each occurrence, independently a moiety comprising two or more double bonds and at least one degree of conjugation, and at least one occurrence of $M^1$ is a moiety comprising three or more aryl or heteroaryl rings, or combinations thereof;

$L^1$, $L^2$ and $L^3$ are, at each occurrence, independently optional linkers comprising atoms selected from carbon, oxygen, sulfur, nitrogen and phosphorous;

$R^1$ is, at each occurrence, independently H, alkyl or alkoxy;

$R^2$ and $R^3$ are independently H, OH, SH, —$NH_2$, alkyl, alkylether, hydroxylalkyl, aminoalkyl, hydroxylalkylether, sulfhydrylalkyl, sulfyhdrylalkylether, cyanoalkyl, —Oaralkyl, phosphate, thiophosphate, phospho, thiophospho, alkylphospho, alkylthiophospho, —Oalkylphospho, —Oalkylthiophospho, alkyletherphospho, alkyletherthiophospho, —Oalkyletherphospho, —Oalkyletherthiophospho phosphoalkyl, phosphoalkylether, thiophosphoalkyl, thiophosphoalkylether, —Ophosphoalkyl, O-phosphoalkylether, —Othiophosphoalkyl or —Othiophosphoalkylether, or $R^2$ is a linker comprising a covalent bond to a biomolecule or microparticle, and $R^3$ is H, OH, SH, alkyl, alkylether, hydroxylalkyl, aminoalkyl, hydroxylalkylether, sulfhydrylalkyl, sulfyhdrylalkylether, cyanoalkyl, —Oaralkyl, phosphate, thiophosphate, alkylphospho, alkylthiophospho, —Oalkylphospho, —Oalkylthiophospho, alkyletherphospho, alkyletherthiophospho, —Oalkyletherphospho, —Oalkyletherthiophospho phosphoalkyl, phosphoalkylether, thiophosphoalkyl, thiophosphoalkylether, —Ophosphoalkyl, O-phosphoalkylether, —Othiophosphoalkyl or —Othiophosphoalkylether; and n is an integer from 1 to 20, for example from 2 to 20 or from 2 to 10.

In other embodiments of the foregoing, w is 0 for each integral value of n, and the compound has the following structure (IIa):

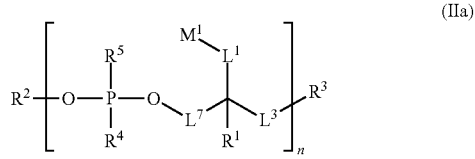

wherein:

$M^1$ is, at each occurrence, independently a moiety comprising two or more double bonds and at least one degree of conjugation, and at least one occurrence of $M^1$ is a moiety comprising four or more aryl or heteroaryl rings, or combinations thereof;

$L^1$, $L^7$ and $L^3$ are, at each occurrence, independently optional alkylene or heteroalkylene linkers;

$R^1$ is, at each occurrence, independently H, alkyl or alkoxy;

$R^2$ is H, alkyl, alkylether, hydroxylalkyl, aminoalkyl, hydroxylalkylether, sulfhydrylalkyl, sulfyhdrylalkylether, cyanoalkyl, phospho, thiophospho, alkylphospho, alkylthiophospho, alkyletherphospho, alkyletherthiophospho, phosphoalkyl, phosphoalkylether, thiophosphoalkyl or thiophosphoalkylether, or $R^2$ is a linker comprising a covalent bond to a biomolecule or microparticle;

$R^3$ is H, OH, SH, —$NH_2$, alkyl, alkylether, hydroxylalkyl, aminoalkyl, hydroxylalkylether, sulfhydrylalkyl, sulfyhdrylalkylether, cyanoalkyl, —Oaralkyl, phosphate, thiophosphate, alkylphospho, alkylthiophospho, —Oalkylphospho, —Oalkylthiophospho, alkyletherphospho, alkyletherthiophospho, —Oalkyletherphospho, —Oalkyletherthiophospho phosphoalkyl, phosphoalkylether, thiophosphoalkyl, thiophosphoalkylether, —Ophosphoalkyl, O-phosphoalkylether, —Othiophosphoalkyl or —Othiophosphoalkylether;

$R^4$ is, at each occurrence, independently $O^-$, $S^-$, OZ, SZ or $N(R^6)_2$, where Z is a cation and each $R^6$ is independently H or alkyl;

$R^5$ is, at each occurrence, independently oxo, thioxo or absent; and n is an integer from 1 to 20, for example from 2 to 20 or from 2 to 10.

In still more embodiments, the compound has the following structure (IIb):

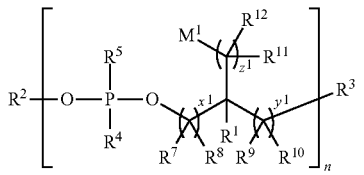

(IIb)

wherein:

$R^7$, $R^8$, $R^9$, $R^{10}$, $R^{11}$ and $R^{12}$ are, at each occurrence, independently H or alkyl; and $x^1$, $y^1$ and $z^1$ are, at each occurrence, independently an integer from 0 to 5.

In other embodiments, the compound has one of the following structures (IIc), (IId), (IIe) or (IIf):

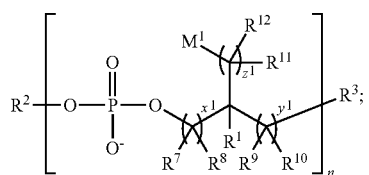

(IIc)

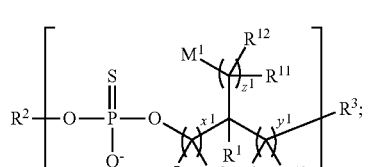

(IId)

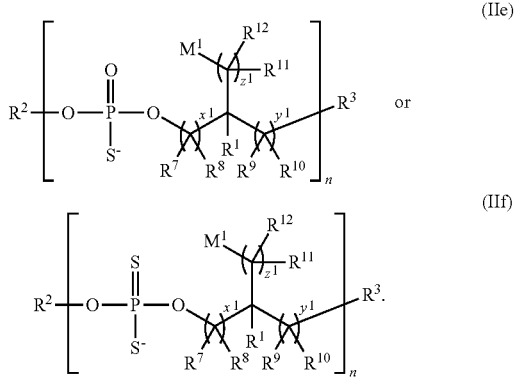

(IIe)

(IIf)

In some embodiments of compounds (IIb), (IIc), (IId), (IIe) or (IIf), $x^1$, $y^1$ and $z^1$ are, at each occurrence, 1. In other embodiments of compounds (IIb), (IIc), (IId), (IIe) or (IIf), $x^1$ is 0, at each occurrence, and $y^1$ and $z^1$ are, at each occurrence, 1. In other embodiments of compounds (IIb), (IIc), (IId), (IIe) or (IIf), n is an integer from 2 to 10. For example, in some embodiments n is 2, 3, 4, 5, 6, 7, 8, 9, or 10.

In still more embodiments, w is 1 for at least one integral value of n. For example, in some embodiments, the compound has the following structure (IIIa):

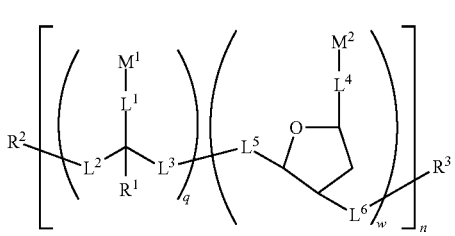

(IIIa)

or a stereoisomer, tautomer or salt thereof, wherein:

$M^1$ and $M^2$ are, at each occurrence, independently a moiety comprising two or more double bonds and at least one degree of conjugation;

$L^1$, $L^2$, $L^3$, $L^4$, $L^5$ and $L^6$ are, at each occurrence, independently optional linkers comprising atoms selected from carbon, oxygen, sulfur, nitrogen and phosphorous;

$R^1$ is, at each occurrence, independently H, alkyl or alkoxy;

$R^2$ and $R^3$ are independently H, OH, SH, —$NH_2$, alkyl, alkylether, hydroxylalkyl, aminoalkyl, hydroxylalkylether, sulfhydrylalkyl, sulfyhdrylalkylether, cyanoalkyl, —Oaralkyl, phosphate, thiophosphate, phospho, thiophospho, alkylphospho, alkylthiophospho, —Oalkylphospho, —Oalkylthiophospho, alkyletherphospho, alkyletherthiophospho, —Oalkyletherphospho, —Oalkyletherthiophospho phosphoalkyl, phosphoalkylether, thiophosphoalkyl, thiophosphoalkylether, —Ophosphoalkyl, O-phosphoalkylether, —Othiophosphoalkyl or —Othiophosphoalkylether, or $R^2$ is a linker comprising a covalent bond to a biomolecule or microparticle, and $R^3$ is H, OH, SH, alkyl, alkylether, hydroxylalkyl, aminoalkyl, hydroxylalkylether, sulfhydrylalkyl, sulfyhdrylalkylether, cyanoalkyl, —Oaralkyl, phosphate, thiophosphate, alkylphospho, alkylthiophospho, —Oalkylphospho, —Oalkylthiophospho, alkyletherphospho, alkyletherthiophospho, —Oalkyletherphospho, —Oalkyletherthiophospho phosphoalkyl, phosphoalkylether, thiophosphoalkyl, thiophosphoalkylether, —Ophosphoalkyl, O-phosphoalkylether, —Othiophosphoalkyl or —Othiophosphoalkylether;

n is an integer from 1 to 10; and q and w are each independently 0 or 1 for each integral value of n, and q and w are each 1 for at least one integral value of n.

In still other embodiments, the compound has the following structure (IIIb):

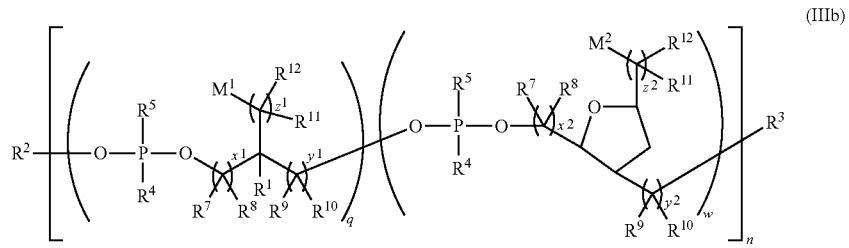

wherein:

$R^7$, $R^8$, $R^9$, $R^{10}$, $R^{11}$ and $R^{12}$ are, at each occurrence, independently H or alkyl; and $x^1$, $x^2$, $y^1$, $y^2$, $z^1$ and $z^2$ are, at each occurrence, independently an integer from 0 to 5.

In some of the foregoing embodiments, $R^5$ is oxo and $R^4$ is O$^-$ or OZ. In other of the foregoing embodiments, $R^2$ is H or an electron pair.

In other of any of the foregoing, $R^2$ is hydroxylalkyl, aminoalkyl, hydroxylalkylether, sulfhydrylalkyl or sulfhydrylalkylether. For example, in some embodiments $R^2$ has one of the following structures:

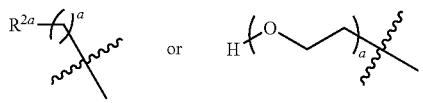

wherein:

$R^{2a}$ is —OH, —NH$_2$, or —SH; and a is an integer from 1 to 10.

In still other of any of the foregoing, $R^2$ is alkylphospho, alkylthiophospho, alkyletherphospho, alkyletherthiophospho, phosphoalkyl, phosphoalkylether, thiophosphoalkyl or thiophosphoalkylether optionally substituted with a substituent selected from —OH, —NH$_2$, and —SH. For example, in some embodiments $R^2$ has one of the following structures:

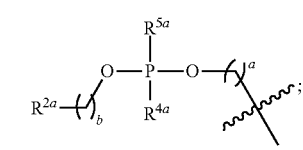

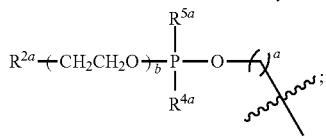

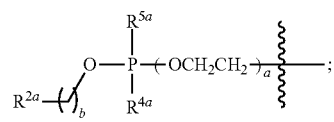

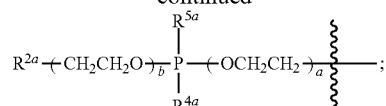

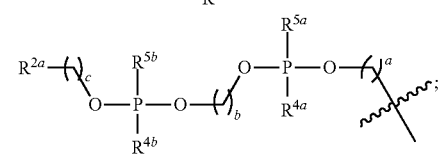

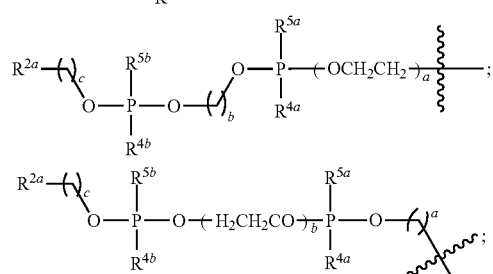

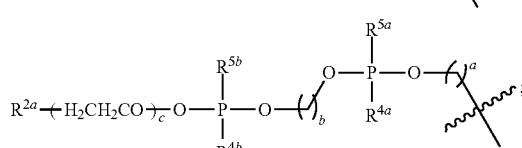

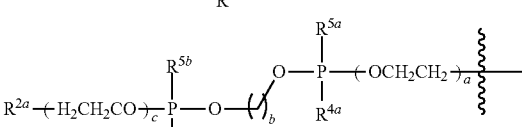

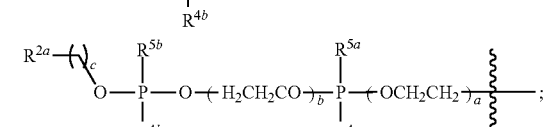

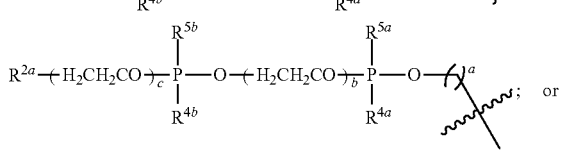

; or

-continued

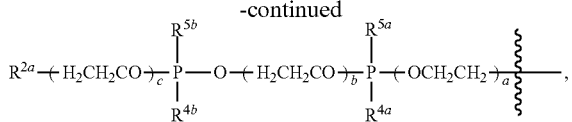

wherein:
$R^{2a}$ is —OH, —SH, —NH$_2$, phosphate or thiophosphate;
$R^{4a}$ and $R^{4b}$ are independently O$^-$, S$^-$, OZ or SZ, where Z is a cation;
$R^{5a}$ and $R^{5b}$ are independently oxo, or thioxo; and
a, b and c are each independently integers from 1 to 10.

In some embodiments, $R^3$ is OH. In still other embodiments of any of the foregoing, $R^3$ is phosphate, thiophosphate, phospho, thiophospho, —Oalkylphospho, —Oalkylthiophospho, —Oalkyletherphospho, —Oalkyletherthiophospho, —Ophosphoalkyl, —Ophosphoalkylether, —Othiophosphoalkyl or —Othiophosphoalkylether optionally substituted with a substituent selected from —OH. —NH$_2$, and —SH.

For example, in some embodiments $R^3$ has one of the following structures:

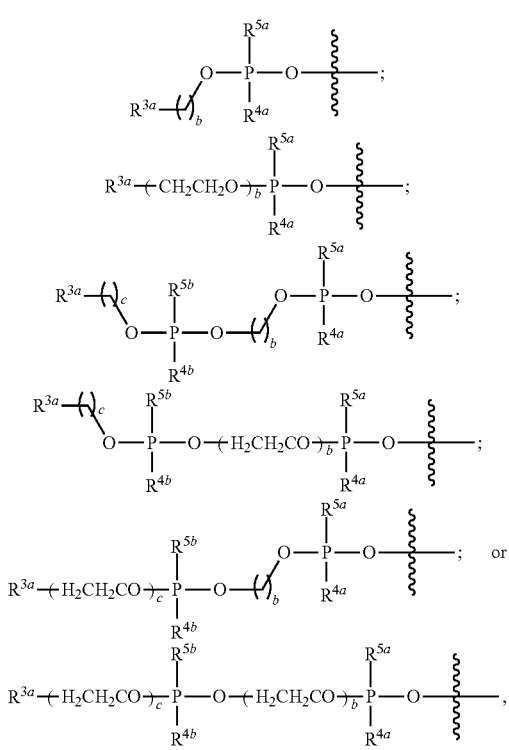

wherein:
$R^{3a}$ is —OH, —SH, —NH$_2$, phosphate or thiophosphate;
$R^{4a}$ and $R^{4b}$ are independently O$^-$, S$^-$, OZ or SZ, where Z is a cation;
$R^{5a}$ and $R^{5b}$ are independently oxo, or thioxo; and
b and c are each independently integers from 1 to 10.

In still other of any of the foregoing, $R^2$ is alkylphospho, alkylthiophospho, alkyletherphospho, alkyletherthiophospho, phosphoalkyl, phosphoalkylether, thiophosphoalkyl or thiophosphoalkylether optionally substituted with a substituent selected from —OH, —NH$_2$, and —SH and $R^3$ is phosphate, thiophosphate, phospho, thiophospho, —Oalkylphospho, —Oalkylthiophospho, —Oalkyletherphospho, —Oalkyletherthiophospho, —Ophosphoalkyl, —Ophosphoalkylether, —Othiophosphoalkyl or —Othiophosphoalkylether optionally substituted with a substituent selected from —OH, —NH$_2$, and —SH.

In even more embodiments $R^2$ has one of the following structures:

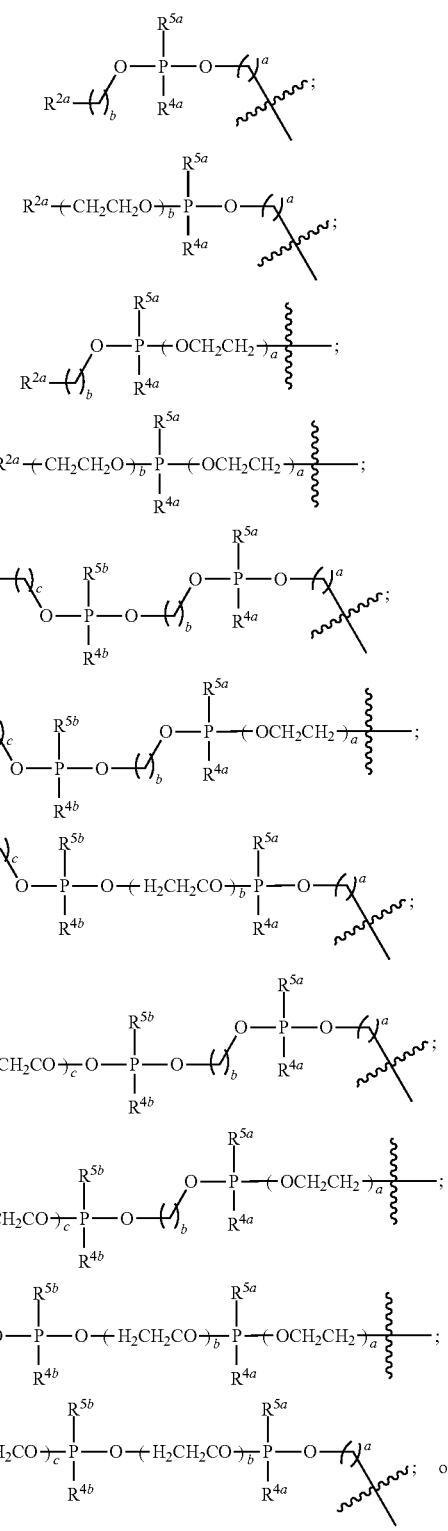

-continued

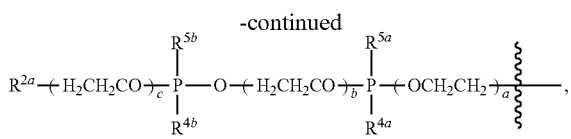

wherein:

$R^{2a}$ is —OH, —SH, —NH$_2$, phosphate or thiophosphate;

$R^{4a}$ and $R^{4b}$ are independently O$^-$, S$^-$, OZ or SZ, where Z is a cation;

$R^{5a}$ and $R^{5b}$ are independently oxo, or thioxo; and a, b and c are each independently integers from 1 to 10, and $R^3$ has one of the following structures:

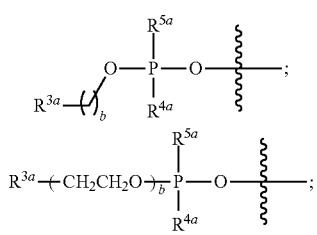

-continued

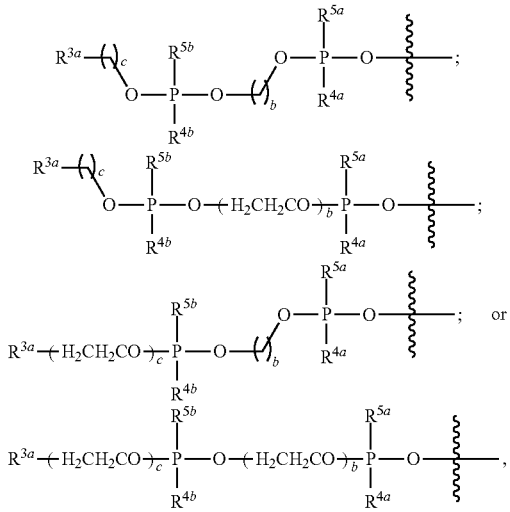

wherein:

$R^{3a}$ is —OH, —SH, —NH$_2$, phosphate or thiophosphate;

$R^{4a}$ and $R^{4b}$ are independently O$^-$, S$^-$, OZ or SZ, where Z is a cation;

$R^{5a}$ and $R^{5b}$ are independently oxo, or thioxo; and b and c are each independently integers from 1 to 10.

In other embodiments of the above, $R^{4a}$ and $R^{4b}$ are each O$^-$ and $R^{5a}$ and $R^{5b}$ are each oxo. In some other embodiments, $R^{4a}$ and $R^{4b}$ are each O$^-$ and $R^{5a}$ and $R^{5b}$ are each thioxo. In other embodiments, $R^{4a}$ and $R^{4b}$ are each S$^-$ and $R^{5a}$ and $R^{5b}$ are each thioxo. In still other embodiments, $R^{4a}$ and $R^{4b}$ are each S$^-$ and $R^{5a}$ and $R^{5b}$ are each oxo.

In more embodiments of the foregoing, at least one of a, b or c is 2. For example, in some embodiments each of a, b and c is 2.

In some different embodiments, at least one of a, b or c is 6. For example, in some embodiments each of a, b and c is 6.

In some embodiments of any of the foregoing compounds of structure (I), (II), (IIa), (IIb), (IIc), (IId), (IIe), (IIf) (III), (IIIa) or (IIIb), n is an integer from 1 to 5, from 2 to 15, from 2 to 10 or from 2 to 5.

In some embodiments of the above foregoing compounds of structure (I), (II), (IIa), (IIb), (IIc), (IId), (IIe), (IIf) (III), (IIIa) or (IIIb), $R^{2a}$ or $R^{3a}$ (or both) are alkylphospho, alkylthiophospho, alkyletherphospho, alkyletherthiophospho, phosphoalkyl, phosphoalkylether, thiophosphoalkyl or thiophosphoalkylether optionally substituted with a substituent selected from —OH, —NH$_2$, and —SH. For example, in some embodiments of any of the foregoing, $R^2$ or $R^3$ (or both: have the following structure:

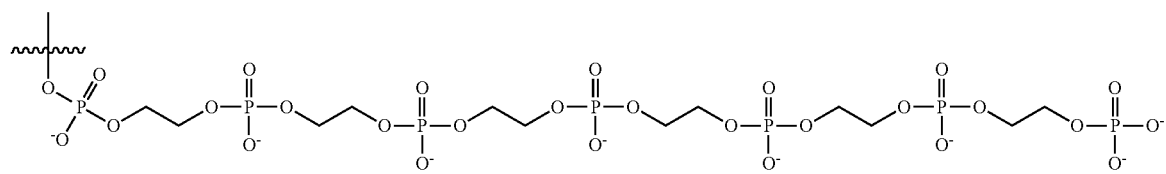

In some embodiments of any the above foregoing compounds of structure (III), (IIIa) or (IIIb), $R^2$ is H or an electron pair, $R^3$ is phosphate and the sum of q and w is at least 2. In some of these embodiments, q is 2 or more, for example 3 or more. In other of these embodiments, each of $L^1$, $L^3$ and $L^7$ are alkylene linkers, for example methylene. In still more embodiments, $L^1$ and $L^3$ are alkylene linkers, such as methylene, and $L^7$ is absent (i.e., a direct bond). In still more of the forgoing embodiments, $M^1$ comprises four or more aryl or heteroaryl rings, or combinations thereof, for example five or more.

In some other embodiments of any the above foregoing compounds of structure (I), (II), (IIa), (IIb), (IIc), (IId), (IIe), (IIf) (III), (IIIa) or (IIIb), $L^3$ is a heteroalkylene linker, for example a heteroalkylene linker comprising O—P—O bonds, S—S bonds, or combinations thereof. In some of these embodiments, $R^2$ is H or an electron pair.

In other embodiments, a compound having the following structure (IV) is provided:

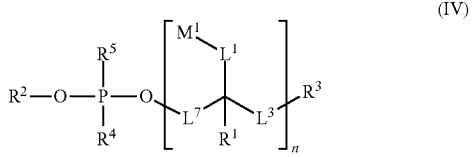

(IV)

wherein:

M¹ is, at each occurrence, independently a moiety comprising two or more double bonds and at least one degree of conjugation, and at least one occurrence of M¹ is a moiety comprising three or more aryl or heteroaryl rings, or combinations thereof;

L¹, L³, and L⁷ are, at each occurrence, independently optional alkylene or heteroalkylene linkers;

R¹ is, at each occurrence, independently H, alkyl or alkoxy;

R² is phospho, thiophospho, alkylphospho, alkylthiophospho, alkyletherphospho, alkyletherthiophospho, phosphoalkyl, phosphoalkylether, thiophosphoalkyl or thiophosphoalkylether, or R² is a linker comprising a covalent bond to a biomolecule or microparticle;

R³ is H, OH, SH, —NH₂, alkyl, alkylether, hydroxylalkyl, aminoalkyl, hydroxylalkylether, sulfhydrylalkyl, sulfyhdrylalkylether, phosphate, thiophosphate, alkylphospho, alkylthiophospho, —Oalkylphospho, —Oalkylthiophospho, alkyletherphospho, alkyletherthiophospho, —Oalkyletherphospho, —Oalkyletherthiophospho phosphoalkyl, phosphoalkylether, thiophosphoalkyl, thiophosphoalkylether, —Ophosphoalkyl, O-phosphoalkylether, —Othiophosphoalkyl or —Othiophosphoalkylether;

R⁴ is, at each occurrence, independently O⁻, S⁻, OZ, SZ or N(R⁶)₂, where Z is a cation and each R⁶ is independently H or alkyl;

R⁵ is, at each occurrence, independently oxo, thioxo or absent; and n is an integer from 1 to 20, for example 1 to 10.

In some embodiments of compound (IV), R² is alkylphospho, alkylthiophospho, alkyletherphospho, alkyletherthiophospho, phosphoalkyl, phosphoalkylether, thiophosphoalkyl or thiophosphoalkylether, wherein R² is optionally substituted with a substituent selected from —OH, —NH₂, and —SH.

For example, in certain embodiments of compound (IV), R² has one of the following structures:

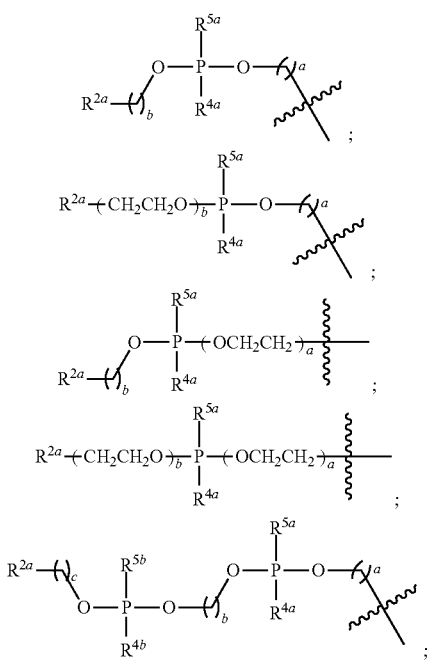

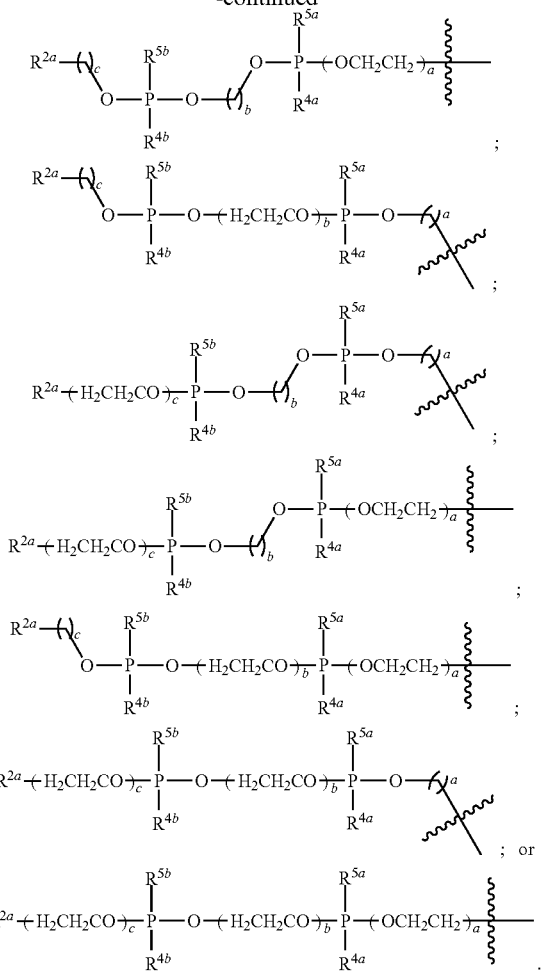

wherein:

$R^{2a}$ is —OH, —SH, —NH₂, phosphate or thiophosphate;

$R^{4a}$ and $R^{4b}$ are independently O⁻, S⁻, OZ or SZ, where Z is a cation;

$R^{5a}$ and $R^{5b}$ are independently oxo, or thioxo; and a, b and c are each independently integers from 1 to 10.

In some embodiments of compound (IV), R³ is OH. In different embodiments, R³ is, phosphate, thiophosphate, phospho, thiophospho, —Oalkylphospho, —Oalkylthiophospho, —Oalkyletherphospho, —Oalkyletherthiophospho, —Ophosphoalkyl, —Ophosphoalkylether, —Othiophosphoalkyl or —Othiophosphoalkylether optionally substituted with a substituent selected from —OH, —NH₂, and —SH.

In still other embodiments of compound (IV), R³ has one of the following structures:

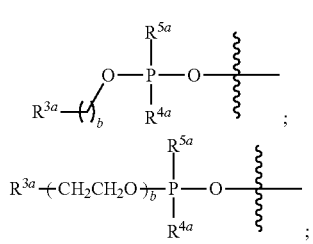

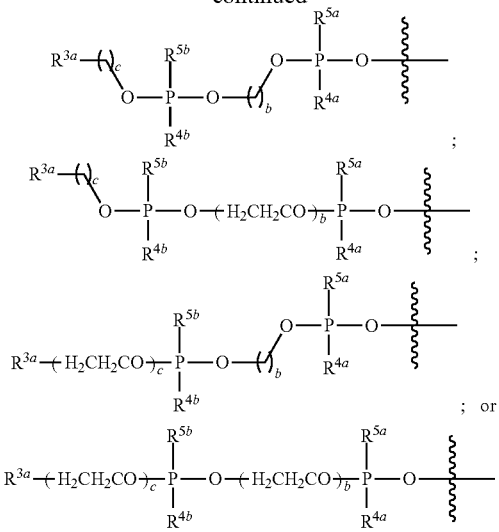

wherein:

R³ᵃ is —OH, —SH, —NH₂, phosphate or thiophosphate;

R⁴ᵃ and R⁴ᵇ are independently O⁻, S⁻, OZ or SZ, where Z is a cation;

R⁵ᵃ and R⁵ᵇ are independently oxo, or thioxo; and b and c are each independently integers from 1 to 10.

In some other embodiments of compound (IV), $R^4$ is O⁻ and $R^5$ is oxo at each occurrence.

In other embodiments of compound (IV), $L^1$, $L^3$ and $L^7$ are each alkylene linkers. In different embodiments, $L^1$ and $L^3$ are each alkylene linkers and $L^7$ is absent. In some of the foregoing embodiments, alkylene is methylene.

In some of the foregoing embodiments, $R^3$ is —OH. In other embodiments, $R^2$ is H (thus at certain pH values, the oxygen atom is negatively charged, i.e., $R^2$ is an electron pair, since the H is acidic).

In some embodiments of structure (IV), $L^7$ and $L^3$ are, at each occurrence, independently optional alkylene, phosphoalkylene or phosphoalkyleneether linkers. In some embodiments, $L^7$ or $L^3$ or both are present. In some embodiments, $L^7$ and $L^3$ are, at each occurrence, independently selected from:

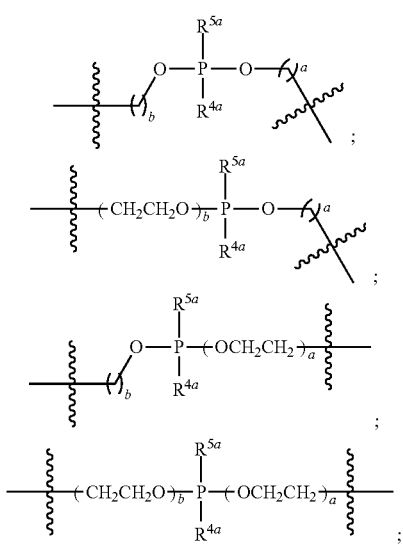

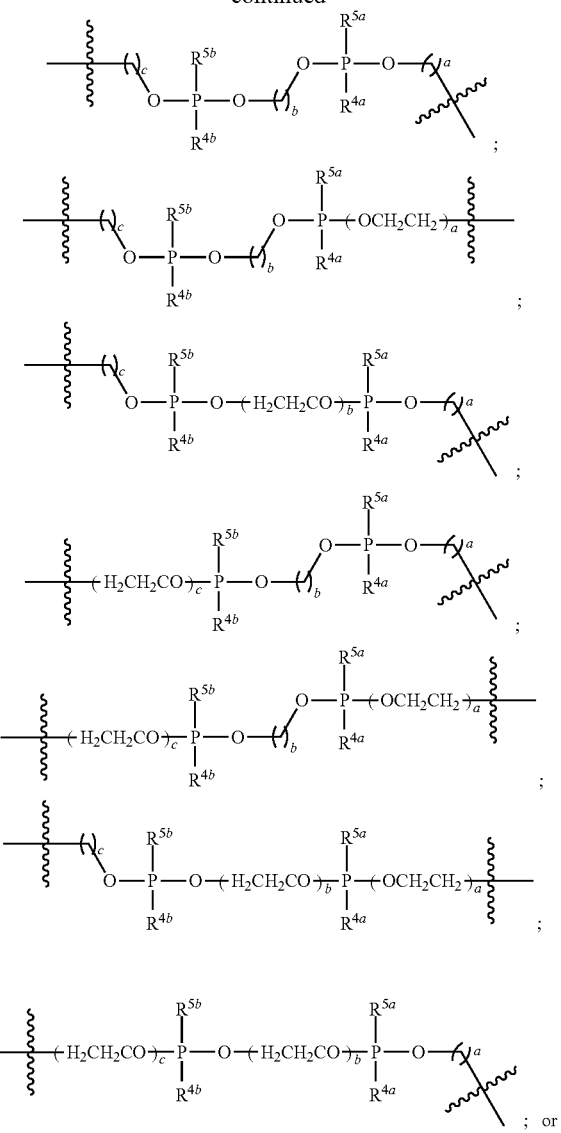

wherein:

R²ᵃ is —OH, —SH, —NH₂, phosphate or thiophosphate;

R⁴ᵃ and R⁴ᵇ are independently O⁻, S⁻, OZ or SZ, where Z is a cation;

R⁵ᵃ and R⁵ᵇ are independently oxo, or thioxo; and a, b and c are each independently integers from 1 to 10.

In some other embodiments of any the above foregoing compounds of structure (IV), one or more occurrences of $L^3$ is a heteroalkylene linker, for example a heteroalkylene linker comprising O—P—O bonds, S—S bonds, or combinations thereof. In some of these embodiments, $R^2$ is H or an electron pair. For example, in some embodiments at least one occurrence of $L^3$ has one of the following structures:

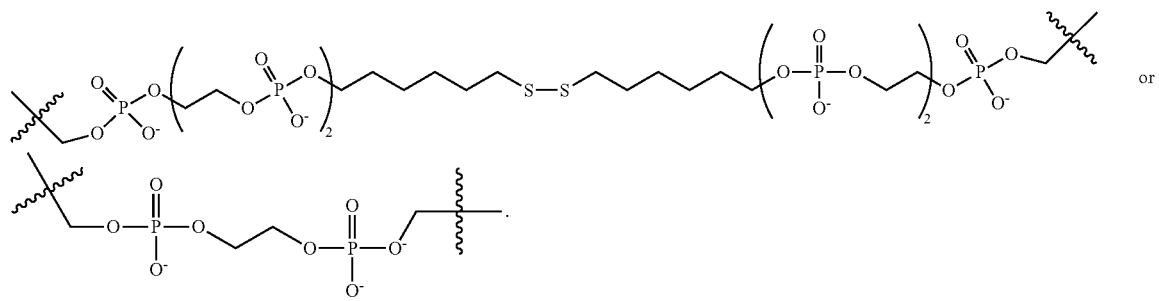

In still other embodiments, a compound having the following structure (Ig) is provided:

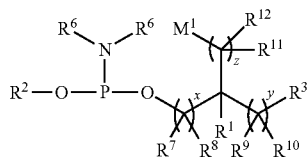

(Ig)

wherein:

$M^1$ is a moiety comprising three or more aryl or heteroaryl rings, or combinations thereof;

$R^1$ is H, $C_1$-$C_6$ alkyl or alkoxy;

$R^2$ is cyanoalkyl;

$R^3$ is H or —Oaralkyl;

$R^6$ is $C_1$-$C_6$ alkyl;

$R^7$, $R^8$, $R^9$, $R^{10}$, $R^{11}$ and $R^{12}$ are, at each occurrence, independently H or alkyl; and x, y and z are, at each occurrence, independently an integer from 0 to 5.

In some embodiments of the compound of structure (Ig), each $R^6$ is isopropyl. In other embodiments, $R^2$ is 2-cyanoethyl. In still more embodiments, $R^3$ is —Oaralkyl, for example —O-dimethoxytrityl (—ODMT).

In different embodiments of compound (Ig), x, y and z are each 1. In other embodiments, x is 0 and y and z are each 1.

In other embodiments, a compound having the following structure (Ih) is provided:

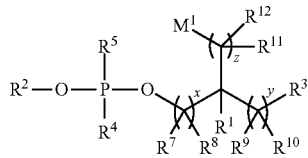

(Ih)

wherein:

$M^1$ is a moiety comprising three or more aryl or heteroaryl rings, or combinations thereof;

$R^2$ is H, an electron pair or a cation;

$R^3$ is OH;

$R^4$ is $O^-$, $S^-$, OZ, SZ where Z is a cation;

$R^5$ is oxo or thioxo;

$R^7$, $R^8$, $R^9$, $R^{10}$, $R^{11}$ and $R^{12}$ are, at each occurrence, independently H or alkyl; and x, y and z are, at each occurrence, independently an integer from 0 to 5.

In some embodiments of (Ih), x, y and z are each 1. In other embodiments, x is 0 and y and z are each 1. In still more embodiments, $R^4$ is $O^-$ or OZ and $R^5$ is oxo.

Other embodiments are directed to a compound having the following structure (Ili):

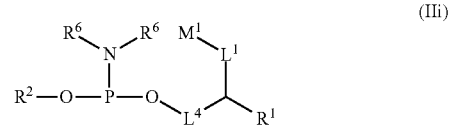

(Ili)

wherein:

$M^1$ is a moiety comprising three or more aryl or heteroaryl rings, or combinations thereof;

$R^1$ is H, $C_1$-$C_6$ alkyl or alkoxy;

$R^2$ is cyanoalkyl;

$R^6$ is $C_1$-$C_6$ alkyl; and $L^1$ and $L^4$ are each independently optional alkylene or heteroalkylene linkers.

In some embodiments of (Ii), each $R^6$ is isopropyl. In some embodiments, $R^2$ is 2-cyanoethyl. In other embodiments, $R^2$ is 2-cyanoethyl. In even other embodiments, $R^1$ is H. In yet more embodiments, $L^1$ and $L^4$ are each independently alkylene linkers, such as methylene linkers.

$M^1$ is generally a visually detectable moiety or substance. For example, $M^1$ may be visually detectable in the UV, visible or IR spectrum. In some of any of the foregoing, $M^1$ is, at each occurrence, independently fluorescent or colored. For example, in some embodiments $M^1$ is fluorescent.

In certain embodiments, $M^1$ is not a purine or pyrimidine base, such as, but not limited to guanine, cytosine, thymidine and adenine. In other embodiments, $M^1$ is not a porphyrin. In other embodiments, $M^1$ is not one of the following:

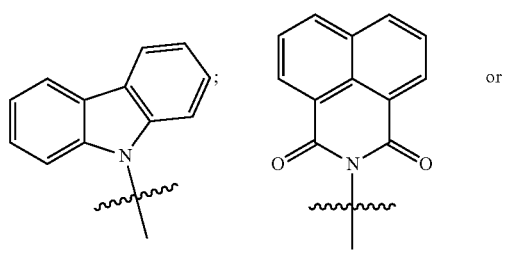

or

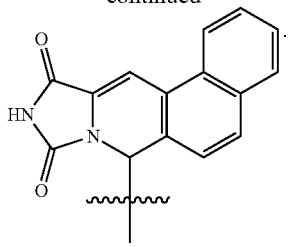

In still other embodiments of any of the foregoing, $M^1$ comprises three or more aryl or heteroaryl rings, or combinations thereof, for example four or more aryl or heteroaryl rings, or combinations thereof, or even five or more aryl or heteroaryl rings, or combinations thereof. In some embodiments, $M^1$ comprises six aryl or heteroaryl rings, or combinations thereof. In further embodiments, the rings are fused. For example in some embodiments, $M^1$ comprises three or more fused rings, four or more fused rings, five or more fused rings, or even six or more fused rings.

In some embodiments, $M^1$ is cyclic. For example, in some embodiments $M^1$ is carbocyclic. In other embodiment, $M^1$ is heterocyclic. In still other embodiments of the foregoing, $M^1$, at each occurrence, independently comprises an aryl moiety. In some of these embodiments, the aryl moiety is multicyclic. In other more specific example, the aryl moiety is a fused-multicyclic aryl moiety, for example which may comprise at least 3, at least 4, or even more than 4 aryl rings.

In other embodiments of any of the foregoing compounds of structure (I), $M^1$, at each occurrence, independently comprises at least one heteroatom. For example, in some embodiments, the heteroatom is nitrogen, oxygen or sulfur.

In still more embodiments of any of the foregoing, $M^1$, at each occurrence, independently comprises at least one substituent. For example, in some embodiments the substituent is a fluoro, chloro, bromo, iodo, amino, alkylamino, arylamino, hydroxy, sulfhydryl, alkoxy, aryloxy, phenyl, aryl, methyl, ethyl, propyl, butyl, isopropyl, t-butyl, carboxy, sulfonate, amide, or formyl group.

In some even more specific embodiments of the foregoing, $M^1$, at each occurrence, independently is a dimethylaminostilbene, quinacridone, fluorophenyl-dimethyl-BODIPY, his-fluorophenyl-BODIPY, acridine, terrylene, sexiphenyl, porphyrin, benzopyrene, (fluorophenyl-dimethyl-difluorobora-diaza-indacene)phenyl, (bis-fluorophenyl-difluorobora-diaza-indacene)phenyl, quaterphenyl, bi-benzothiazole, ter-benzothiazole, bi-naphthyl, bi-anthracyl, squaraine, squarylium, 9,10-ethynylanthracene or ter-naphthyl moiety. In other embodiments, $M^1$ is, at each occurrence, independently p-terphenyl, perylene, azobenzene, phenazine, phenanthroline, acridine, thioxanthrene, chrysene, rubrene, coronene, cyanine, perylene imide, or perylene amide or a derivative thereof. In still more embodiments, $M^1$ is, at each occurrence, independently a coumarin dye, resorufin dye, dipyrromethenboron difluoride dye, ruthenium bipyridyl dye, energy transfer dye, thiazole orange dye, polymethine or N-aryl-1,8-naphthalimide dye.

In still more embodiments of any of the foregoing, $M^1$ at each occurrence is the same. In other embodiments, each $M^1$ is different. In still more embodiments, one or more $M^1$ is the same and one or more $M^1$ is different.

In some embodiments, $M^1$ is pyrene, perylene, perylene monoimide or 6-FAM or derivative thereof. In some other embodiments, $M^1$ has one of the following structures:

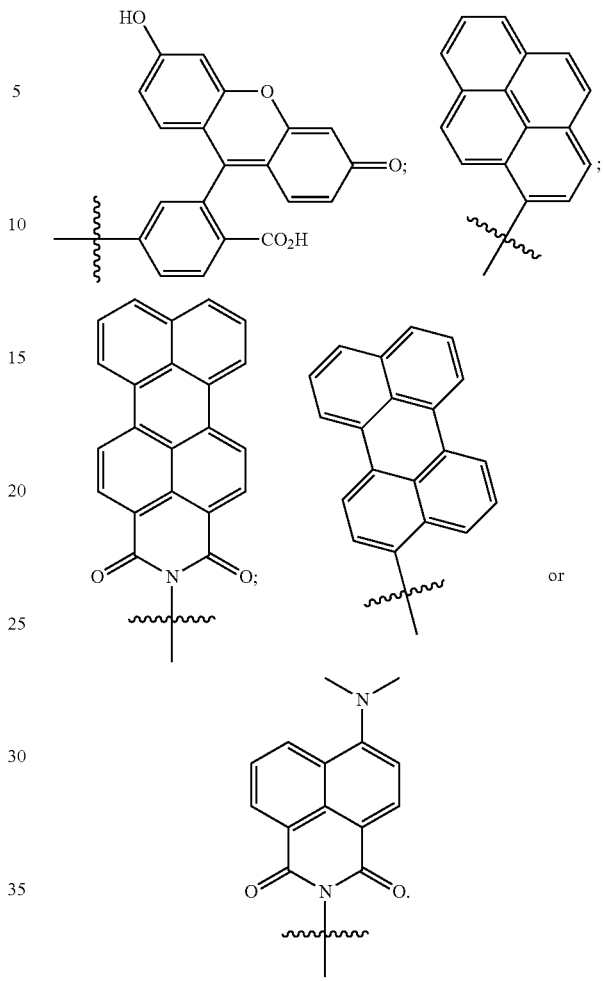

In some embodiments, $M^2$ is selected from any one of the above described $M^1$ moieties. In some embodiments, $M^1$ and $M^2$ are the same. In other embodiments, $M^1$ and $M^2$ are different.

In other embodiments, at least one occurrence of $M^2$ is a base pairing moiety. For example, in some embodiments each occurrence of $M^2$ is a base pairing moiety. In some of these embodiments, the base pairing moiety is a purine, a pyrimidine, a dihydropyrimidine or a derivative thereof. In further embodiments, the base pairing moiety has one of the following structures:

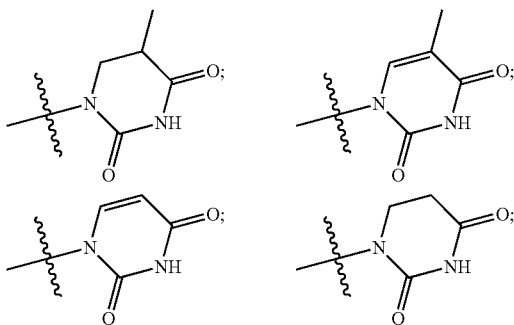

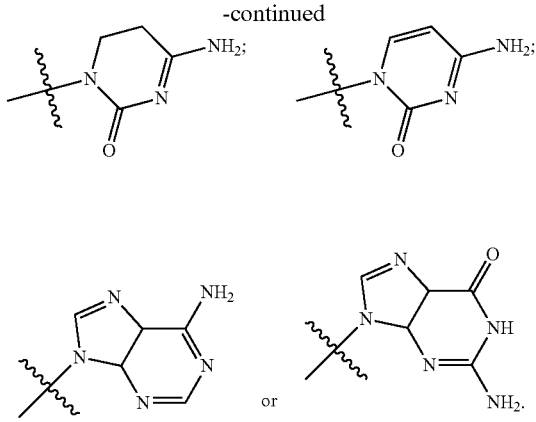

In some of the foregoing embodiments, $R^2$ is a linker comprising a covalent bond to a biomolecule or microparticle, and $R^3$ is H, OH, phosphate, thiophosphate, phosphoalkyl, phosphoalkylether, thiophosphoalkyl or thiophosphoalkylether. For example, in some embodiments $R^2$ is a linker comprising a covalent linkage to a biomolecule. For example, a nucleic acid, amino acid or a polymer thereof (e.g., polynucleotide or polypeptide). In still more embodiments, the biomolecule is an enzyme, receptor, receptor ligand, antibody, glycoprotein, aptamer or prion.

In yet other embodiments, $R^2$ is a linker comprising a covalent linkage to a microparticle. For example, in some embodiments the microparticle is a polymeric bead or nonpolymeric bead.

In some more embodiments of some of the foregoing embodiment, $R^7$, $R^8$, $R^9$, $R^{10}$, $R^{11}$ and $R^{12}$, when present, are each H.

In some other embodiments, x, y and z are each 1.

In some of any of the foregoing embodiments, $R^3$ is —OH, phosphate or thiophosphate. In other embodiments, $R^3$ is —OH, phosphate, thiophosphate, phosphoalkyl or thiophosphoalkyl. In some more embodiments, $R^3$ is phosphoalkyl or thiophosphoalkyl.

The present invention includes monomeric compounds (e.g., n=1) as well as oligomeric compound (e.g., n is 2-20 or 2-10). In other of the foregoing embodiments, n is an integer from 1 to 5. For example, in some embodiments, n is an integer from 2 to 10, or 2 to 5, such as 3. In other embodiments n is 1. In more embodiments, n is 2. In other embodiments n is 3. In more embodiments, n is 4. In other embodiments n is 5. In more embodiments, n is 6. In other embodiments n is 7. In more embodiments, n is 8. In other embodiments n is 9. In more embodiments, n is 10.

Any number of methylene spacer units (i.e., x, y and z) can be included. In some embodiments x is 0. In other embodiments x is 1. In more embodiments, x is 2. In some embodiments x is 3. In other embodiments x is 4. In more embodiments, x is 5.

In some embodiments y is 0. In other embodiments y is 1. In more embodiments, y is 2. In some embodiments y is 3. In other embodiments y is 4. In more embodiments, y is 5.

In some embodiments z is 1-5. In some embodiments z is 0. In other embodiments z is 1. In more embodiments, z is 2. In some embodiments z is 3. In other embodiments z is 4. In more embodiments, z is 5.

In other embodiments, x is 1, y is 0 and z is 1. In other embodiments, x is 0, y is 1 and z is 1.

In some specific embodiments, a compound having one of the following structures is provided:

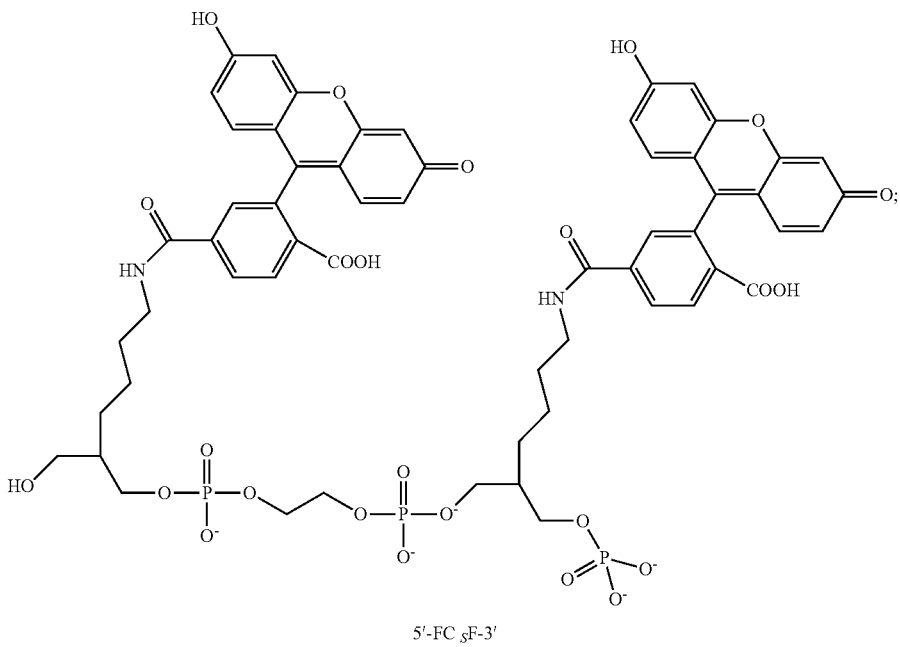

5'-FC $_s$F-3'

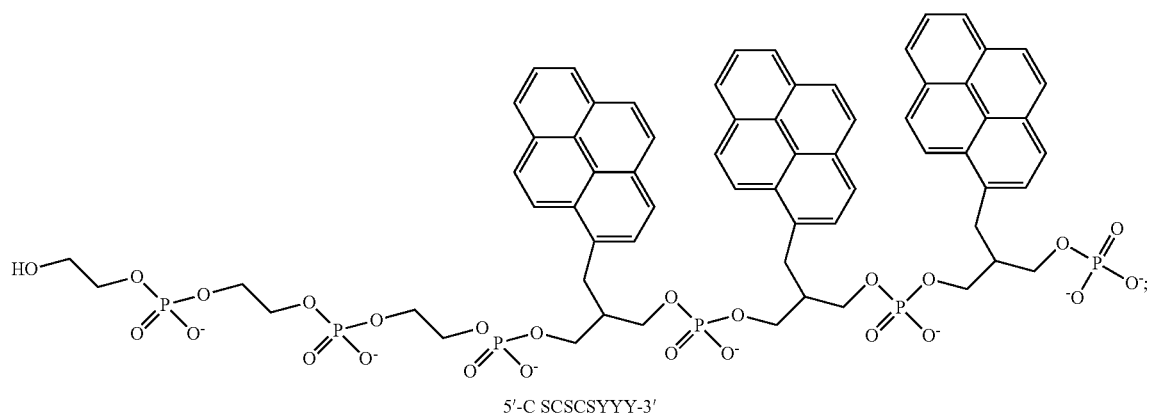
5'-C SCSCSYYY-3'
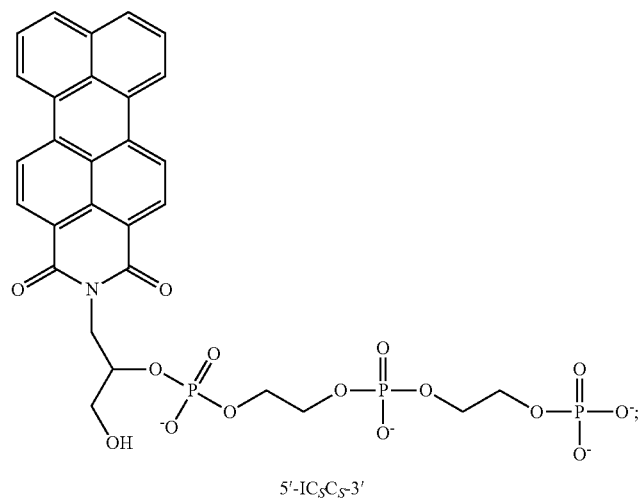
5'-IC$_S$C$_S$-3'
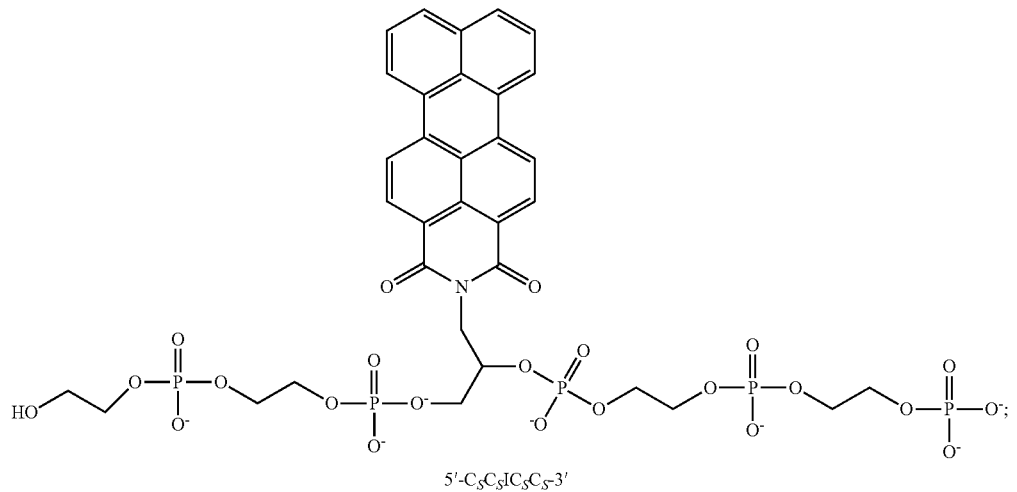
5'-C$_S$C$_S$IC$_S$C$_S$-3'

-continued
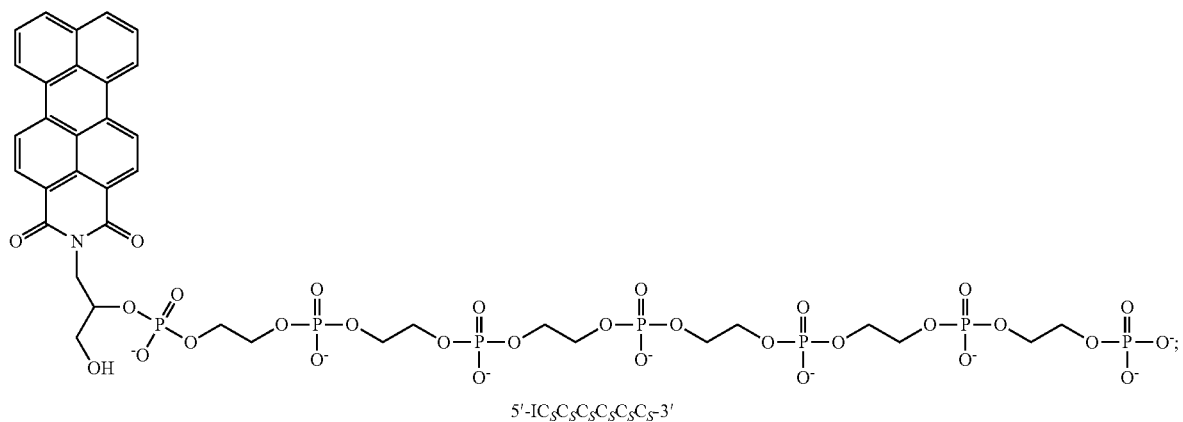
5'-IC$_S$C$_S$C$_S$C$_S$C$_S$-3'
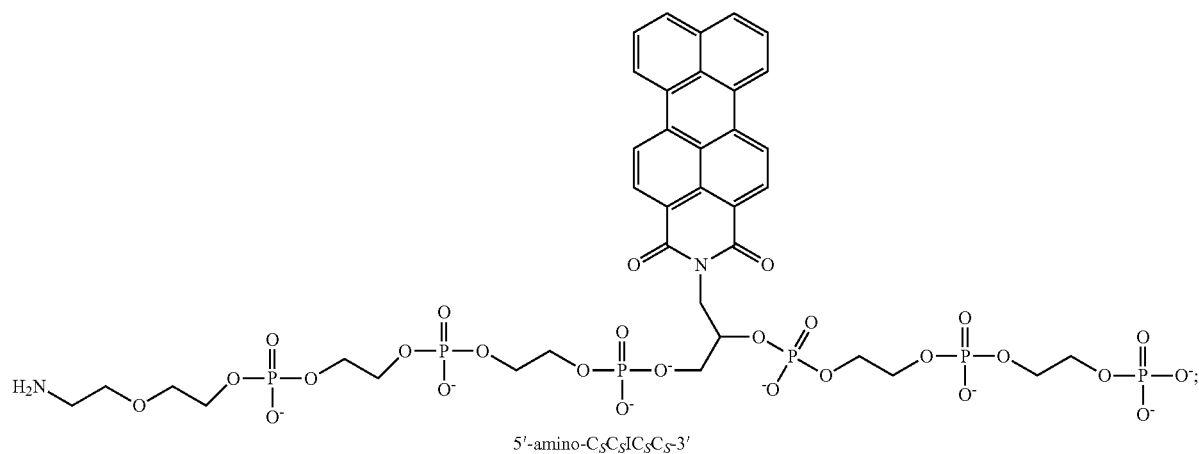
5'-amino-C$_S$C$_S$IC$_S$C$_S$-3'
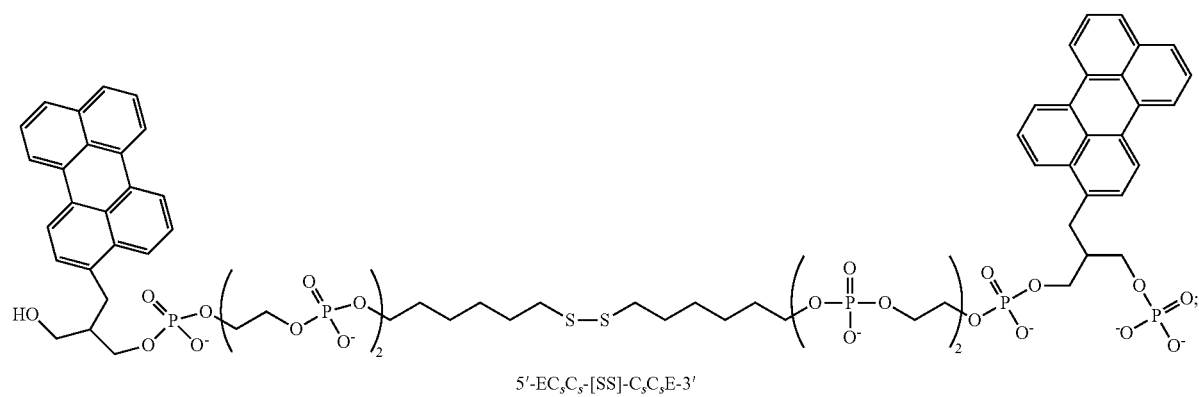
5'-EC$_S$C$_S$-[SS]-C$_S$C$_S$E-3'
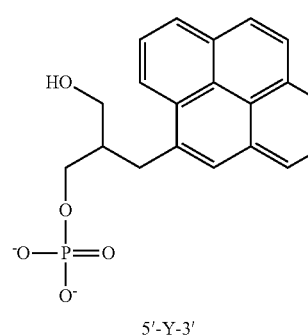
5'-Y-3'
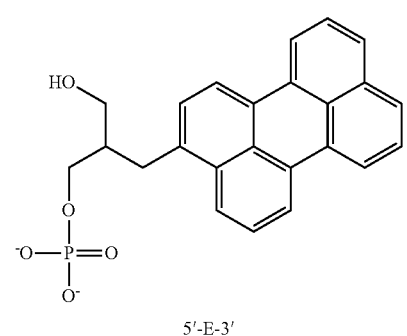
5'-E-3'
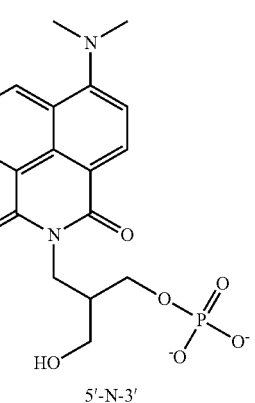
5'-N-3'

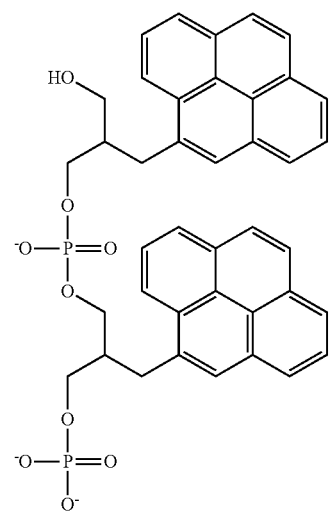
5′-YY-3′
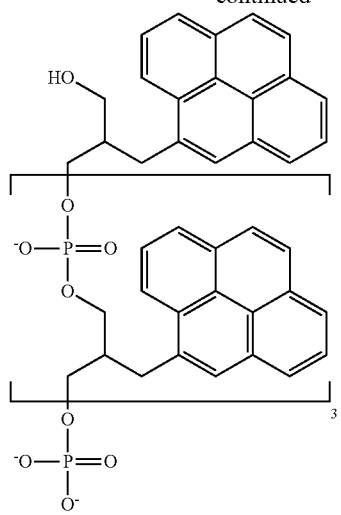
5′-YYYY-3′    5′-YYYYY-3′
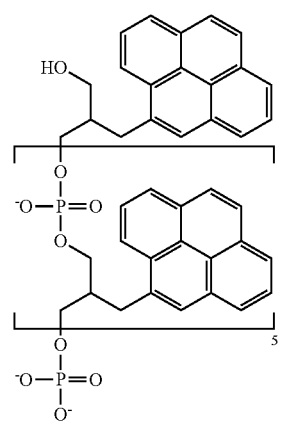
5′-YYYYYY-3′
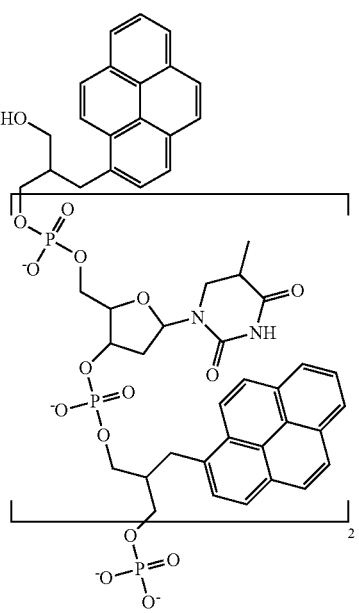
5′-YT$_h$YT$_h$Y-3′
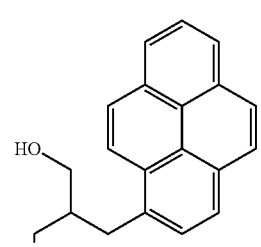
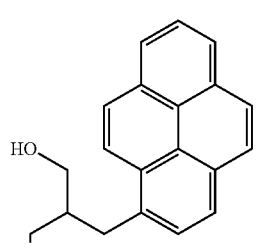

-continued
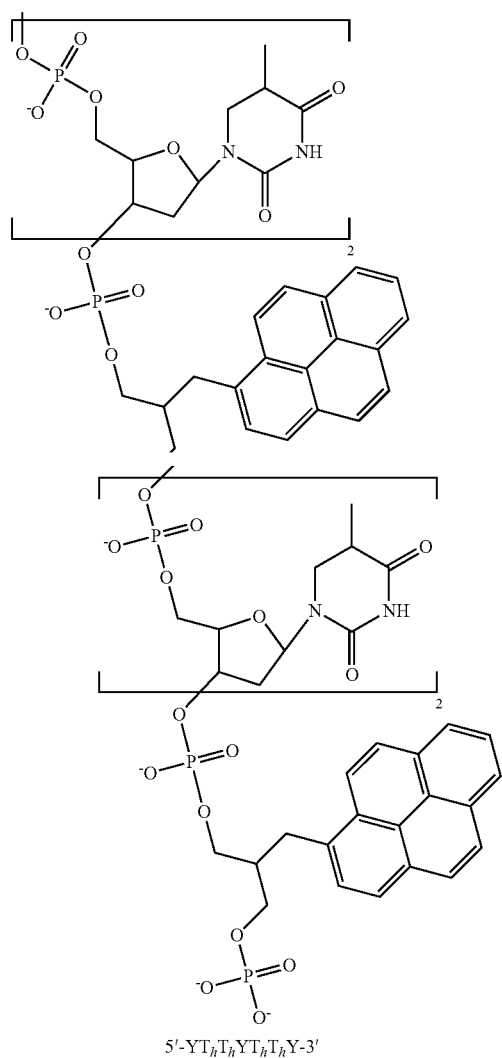
5′-YT$_h$T$_h$YT$_h$T$_h$Y-3′
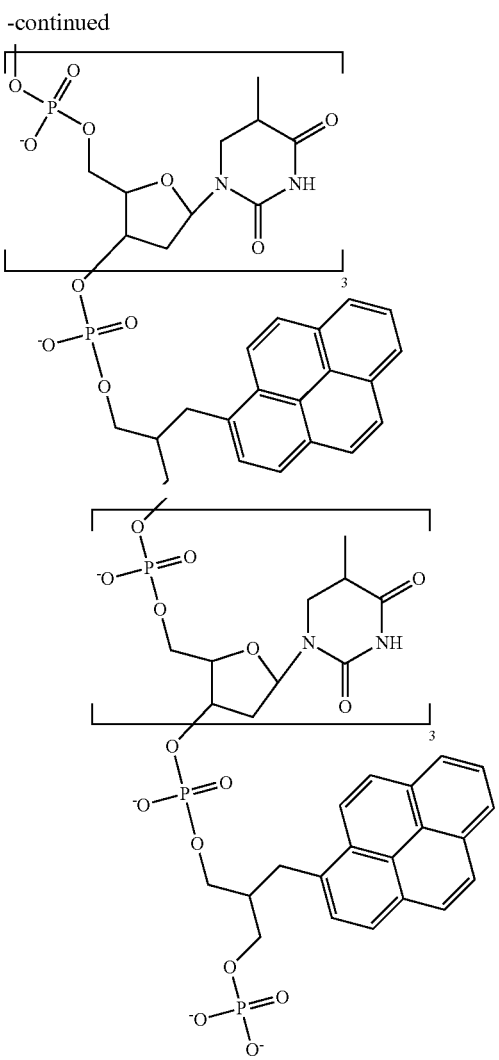
5′-YT$_h$T$_h$T$_h$YT$_h$T$_h$T$_h$Y-3′
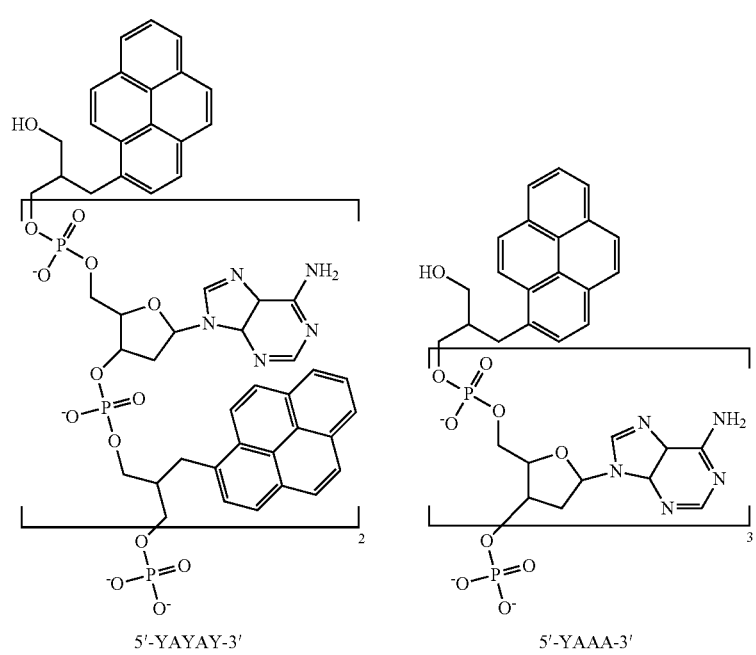
5′-YAYAY-3′     5′-YAAA-3′

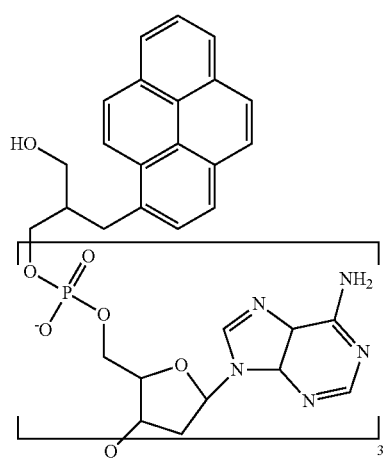
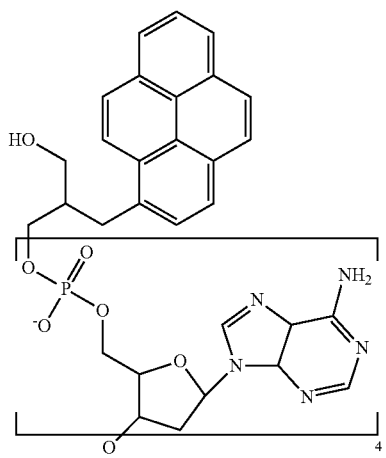
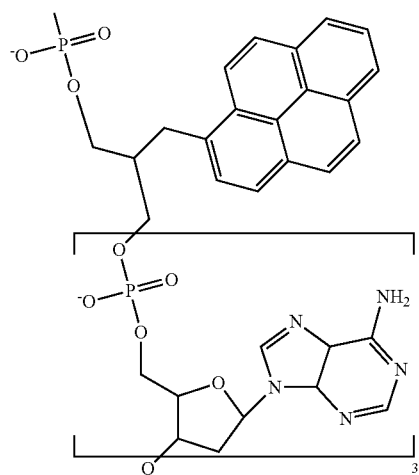
5'-YAAAYAAA-3'
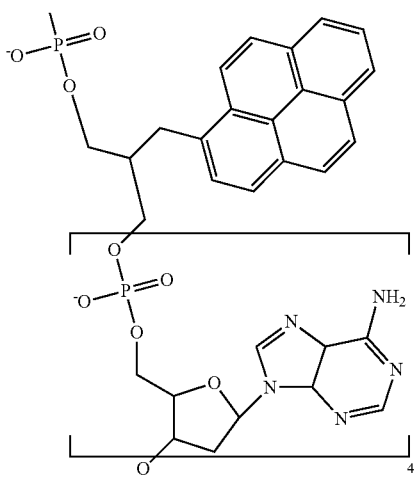
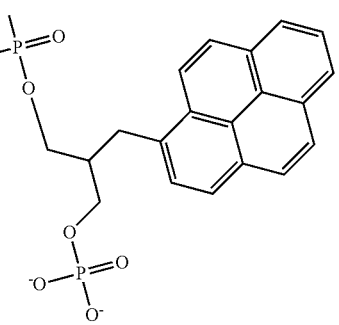
5'-YAAAAYAAAA-3'

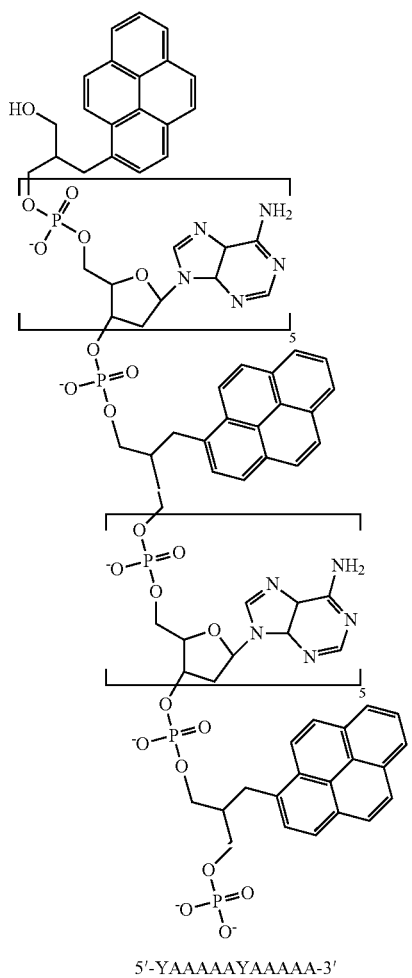

5'-YAAAAAYAAAAA-3'

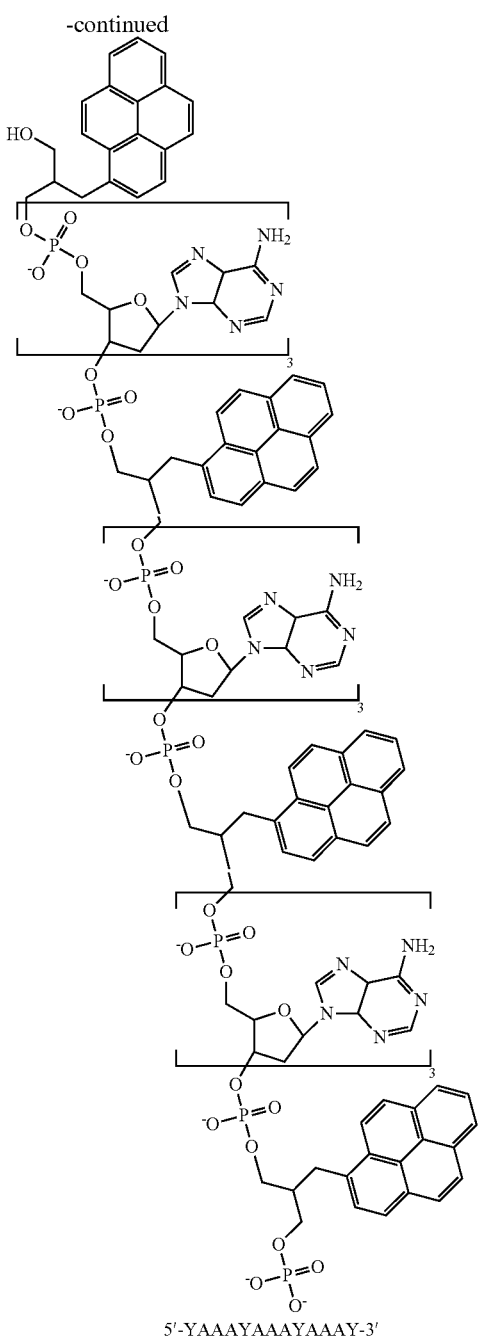

5'-YAAAYAAAYAAAY-3'

For ease of illustration, various compounds comprising phosphorous moieties (e.g., phosphate and the like) are depicted in the anionic state (e.g., $-OPO_3^{2-}$). One of skill in the art will readily understand that the charge is dependent on pH and the uncharged (e.g., protontated or salt, such as sodium or other cation) forms are also included in the scope of the invention.

Compositions comprising any of the foregoing compounds and one or more biomolecules are provided in various other embodiments. In some embodiments, use of such compositions in analytical methods for detection of the one or more biomolecules are also provided.

In still other embodiments, the compounds are useful in various analytical methods. For example, in certain embodiments the disclosure provides a method of staining a sample, the method comprising adding to said sample a compound of structure (I), wherein $R^2$ is a linker comprising a covalent bond to a biomolecule or microparticle, and $R^3$ is H, OH, phosphate, thiophosphate, phosphoalkyl, phosphoalkylether, thiophosphoalkyl or thiophosphoalkylether in an amount sufficient to produce an optical response when said sample is illuminated at an appropriate wavelength.

In some embodiments of the foregoing methods, $R^2$ is a linker comprising a covalent linkage to a biomolecule. For example, a nucleic acid, amino acid or a polymer thereof (e.g., polynucleotide or polypeptide). In still more embodiments, the biomolecule is an enzyme, receptor, receptor ligand, antibody, glycoprotein, aptamer or prion.

In yet other embodiments of the foregoing method, $R^2$ is a linker comprising a covalent linkage to a microparticle. For example, in some embodiments the microparticle is a polymeric bead or nonpolymeric bead.

In even more embodiments, said optical response is a fluorescent response.

In other embodiments, said sample comprises cells, and some embodiments further comprise observing said cells by flow cytometry.

In still more embodiments, the method further comprises distinguishing the fluorescence response from that of a second fluorophore having detectably different optical properties.

In other embodiments, the disclosure provides a method for visually detecting a biomolecule, comprising:
(a) providing a compound of structure (I), wherein $R^2$ is a linker comprising a covalent bond to the biomolecule, and $R^3$ is H, OH, phosphate, thiophosphate, phosphoalkyl, phosphoalkylether, thiophosphoalkyl or thiophosphoalkylether; and
(b) detecting the compound by its visible properties.

For example, a nucleic acid, amino acid or a polymer thereof (e.g., polynucleotide or polypeptide). In still more embodiments, the biomolecule is an enzyme, receptor, receptor ligand, antibody, glycoprotein, aptamer or prion.

In other embodiments, a method for visually detecting a biomolecule is provided, the method comprising:
(a) admixing any of the foregoing compounds with one or more biomolecules; and
(b) detecting the compound by its visible properties.

It is understood that any embodiment of the compounds of structure (I), as set forth above, and any specific choice set forth herein for a $R^1$, $R^2$, $R^3$, $L^1$, $L^2$, $L^3$, $L^4$, $L^5$, $L^6$, $M^1$, $M^2$, A, q, w or n variable in the compounds of structure (I), as set forth above, may be independently combined with other embodiments and/or variables of the compounds of structure (I) to form embodiments of the inventions not specifically set forth above. In addition, in the event that a list of choices is listed for any particular R or M group in a particular embodiment and/or claim, it is understood that each individual choice may be deleted from the particular embodiment and/or claim and that the remaining list of choices will be considered to be within the scope of the invention.

It is understood that in the present description, combinations of substituents and/or variables of the depicted formulae are permissible only if such contributions result in stable compounds.

It will also be appreciated by those skilled in the art that in the process described herein the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

Furthermore, all compounds of the invention which exist in free base or acid form can be converted to their salts by treatment with the appropriate inorganic or organic base or acid by methods known to one skilled in the art. Salts of the compounds of the invention can be converted to their free base or acid form by standard techniques.

The following Reaction Schemes illustrate exemplary methods of making compounds of this invention. It is understood that one skilled in the art may be able to make these compounds by similar methods or by combining other methods known to one skilled in the art. It is also understood that one skilled in the art would be able to make, in a similar manner as described below, other compounds of structure (I) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described in this invention.

Reaction Scheme I

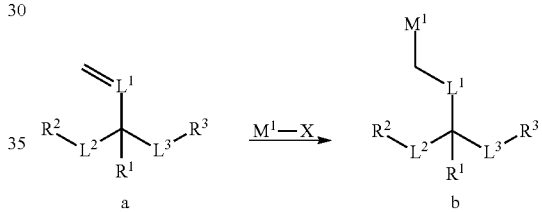

Reaction Scheme I illustrates and exemplary method for preparing compounds of structure I. Referring to Reaction Scheme 1, compounds of structure a can be purchased or prepared by methods well-known to those of ordinary skill in the art. Reaction of a with $M^1$-X, where x is a halogen such as bromo, under Suzuki coupling conditions known in the art results in compounds of structure b. Compounds of structure b can be modified to obtain number of other compounds of structure I. For example, compounds of structure b can be oligomerized to obtain other compounds of structure I (i.e., where n is greater than 1, such as 2-10). Exemplary methods for oligomerization include methods analogous to phosphoramadite-based solid-phase oligonucleotide synthesis, which is well known in the art.

Reaction Scheme II

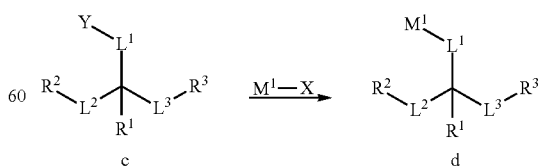

Reaction Scheme II illustrates an alternative method for preparation of compounds of structure I. In this approach, a compound of structure c, which can be purchased or prepared by well-known techniques, is reacted with $M^1$-Z to yield compounds of structure d. Here, Y and Z represent function groups having complementary reactivity (i.e., functional groups which react to form a covalent bond). Z may be pendant to $M^1$ or a part of the structural backbone of M, for example a cyclic anhydride. Y may be any number of functional groups, such as amino.

Compounds of structure (I) comprising ribose moieties are prepared according to analogous procedures or purchased from commercial sources (e.g., as phosphoramadites).

In certain embodiments, the compounds of structure I are oligomers comprising from 2-10 repeating units. Such oligomers can be prepared using methods analogous to well-known automated DNA synthesis methods. DNA synthesis methods are well-known in the art. Briefly, two alcohol groups are functionalized with a dimethoxytrityl (DMT) group and a 2-cyanoethyl-N,N-diisopropylamino phosphoramidite group, respectively. The phosphoramidite group is coupled to an alcohol group, typically in the presence of an activator such as tetrazole, followed by oxidation of the phosphorous atom with iodine. The dimethoxytrityl group can be removed with acid (e.g., chloroacetic acid) to expose the free alcohol, which can be reacted with a phosphoramidite group. The 2-cyanoethyl group can be removed after oligomerization by treatment with aqueous ammonia.

Preparation of the phosphoramidites used in the oligomerization methods is also well-known in the art. For example, a primary alcohol (e.g., $R^3$) can be protected as a DMT group by reaction with DMT-Cl. A secondary alcohol (e.g., $R^2$) is then functionalized as a phosphoramidite by reaction with an appropriate reagent such as 2-cyanoethyl N,N-dissopropylchlorophosphoramidite. Methods for preparation of phosphoramidites and their oligomerization are well-known in the art and described in more detail in the examples.

The following examples are provided for purposes of illustration, not limitation.

EXAMPLES

General Methods $^1$H and $^{31}$P NMR spectra were obtained on a JEOL 400 MHz spectrometer. $^{31}$P NMR spectra were referenced against 85% aqueous phosphoric acid and $^1$H spectra were referenced against TMS. Reverse phase HPLC dye analysis was performed using a Waters Acquity UHPLC system with a 2.1 mm×50 mm Acquity BEH-C18 column held at 45° C. Mass spectral analysis was performed on a Waters/Micromass Quattro micro MS/MS system (in MS only mode) using MassLynx 4.1 acquisition software. Mobile phase used for LC/MS on dyes was 100 mM 1,1,1,3,3,3-hexafluoro-2-propanol (HFIP), 8.6 mM triethylamine (TEA), pH 8. Phosphoramidites and precursor molecules were analyzed using an Agilent Infinity 1260 UHPLC system with a diode array detector and High Performance Autosampler using an Aapptec© Spirit™ Peptide C18 column (4.6 mm×100 mm, 5 μm particle size). Excitation and emission profiles experiments were recorded on a Cary Eclipse spectra photometer.

All reactions were carried out in oven dried glassware under a nitrogen atmosphere unless otherwise stated. Commercially available DNA synthesis reagents were purchased from Glen Research (Sterling, Va.) Anhydrous pyridine, toluene, dichloromethane, diisopropylethyl amine, triethylamine, acetic acid, pyridine, and THF were purchased from Aldrich. All other chemicals were purchased from Aldrich or TCI and were used as is with no additional purification.

All oligomer dyes were synthesized on an ABI 394 DNA synthesizer using standard protocols for the phosphoramidite-based coupling approach. The chain assembly cycle for the synthesis of oligomers was the following: (i) detritylation, 3% trichloroaceticacid in dichloromethane, 1 min; (ii) coupling, 0.1 M phosphoramidite and 0.45 M tetrazole in acetonitrile, 10 min; (iii) capping, 0.5 M acetic anhydride in THF/lutidine, 1/1, v/v 15 s; (iv) oxidation, 0.1 M iodine in THF/pyridine/water, 10/10/1, v/v/v, 30 s.

Chemical steps within the cycle were followed by acetonitrile washing and flushing with dry argon for 0.2-0.4 min. Cleavage from the support and removal of base and phosphoramidate protecting groups was achieved by treatment with ammonia for 1 hour at room temperature. Oligomer dyes were then analyzed by reverse phase HPLC as described above.

Example 1

Synthesis of Phosphoramidite Dye Monomers

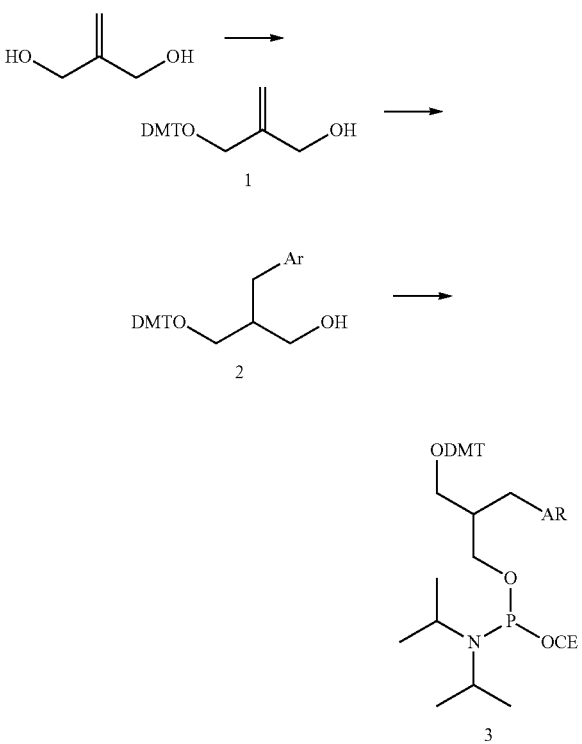

Ar = pyrene
DMT = 4,4'-dimethoxytrityl
CE = 2-cyanoethyl

1-O-(4,4'-dimethoxytrityl-2-methylene-1,3-propanediol (1)

Into a dry 500 mL round bottom flask was put a stir bar. After flushing with nitrogen, dry pyridine (240 mL) was added, and the flask was cooled in an ice bath for 15 minutes. Upon cooling DMTrCl (7.65 g, 22.5 mmol) was added after which the flask was stirred overnight in a refrigerator at 4° C. under a nitrogen atmosphere. Several drops of methanol were then added and the reaction was concentrated in vacuo to a viscous gum. The resulting gum was dissolved in EtOAc (200 mL) and washed with NaHCO$_3$ (250 mL) and sat. NaCl (250 mL). The organic layer was dried over Na$_2$SO$_4$ and concentrated in vacuo to a viscous gum. The isolated crude product wash then purified by silica gel column chromatography eluting with a gradient of EtOAc:hexanes (25:75 v/v)-(1:1 v/v) to give 1 as a clear gum (5.21 g, 60%). $^1$H NMR was recorded and found to be consistent with the structure of compound 1.

1-O-(4,4'-dimethoxytrityl)-2-hydroxymethyl-3-pyrenylpropanol (2)

Into a dry 250 mL round bottom flask fitted with a condenser was put a stir bar. The flask was purged with nitrogen, and dry THF (40 mL) and compound 1 (5.0 g, 12.8 mmol) were added. 0.5 M 9-BBN in THF (65 mL, 32 mmol) was added via syringe and the reaction was heated to reflux for 12 hrs. After allowing the reaction to cool to room temperature, 3M K$_2$CO$_3$ (11 ml) and dry DMF (100 mL) were added. 1-Bromopyrene (2.0 g, 6.5 mmol) and PdCl$_2$ (dppf) (0.65 g, 0.8 mmol) were added, and the solution was allowed to stir for 15 hrs at room temperature. The reaction mixture was poured into CH$_2$Cl$_2$ (300 mL) and washed with H$_2$O (500 mL). The aqueous layer was then back extracted with additional CH$_2$Cl$_2$ (200 mL). The combined organic layers were washed with sat. NaCl (300 mL), dried over Na$_2$SO$_4$, and concentrated in vacuo to a viscous gum. The isolated crude product wash then purified by silica gel column chromatography eluting with a gradient of EtOAc:hexanes (25:75 v/v)-(1:1 v/v) to give 2 as a clear gum (3.0 g, 79%). The $^1$H NMR spectrum was recorded and found to be consistent with the structure of compound 2.

1-O-(4,4'-dimethoxytrityl)-2-methylpyrene-3-O-(2-cyanoethyl-N,N-diisopropyl)propane phosphoramidite (3)

Into a dry 100 mL round bottom flask was put a stir bar. After purging the flask with nitrogen, CH$_2$Cl$_2$ (20 mL) and compound 2 (0.30 g, 0.50 mmol) were added. N,N-Diisopropylethylamine (0.88 mL, 5.0 mmol) and 2-cyanoethyl diisopropychlorophosphoramidite (0.45 mL, 2.0 mmol) were added via syringe. After 1 hour of stirring at room temperature, the reaction was determined to be complete by TLC analysis. The crude reaction mixture was then purified directly by silica gel column chromatography eluting with a gradient of EtOAc:hexanes:TEA (22.5:72.5:5 v/v/v) to give 3 as a white foam (0.28 g, 70%). The $^{31}$P NMR spectrum was recorded and found to be consisted with the structure of compound 3: Purity was determined by HPLC analysis with detection at 254 and 340 nm.

Other compounds with different Ar groups (e.g., perylene) were prepared in an analogous manner.

Example 2

Synthesis of Perylene Carbodiimide Dye Monomer

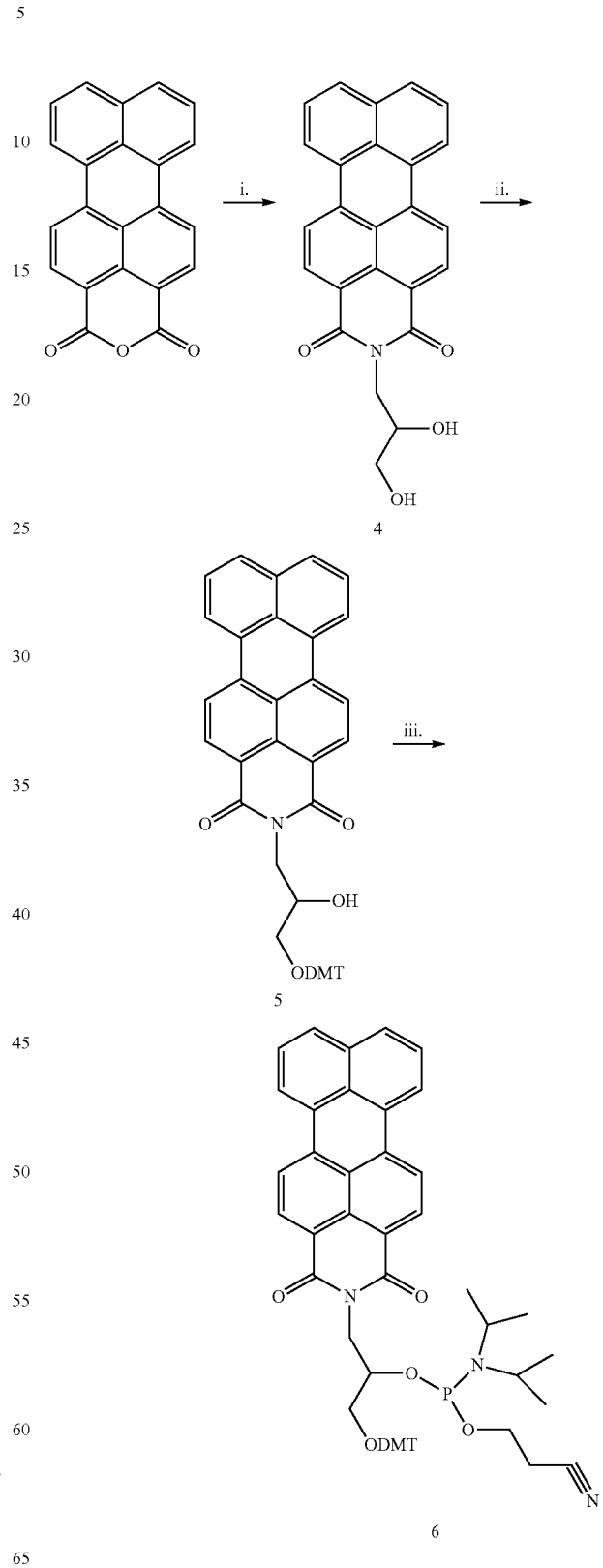

N-(2,3-propanediol) perylenemonoimide (4)

Into a dry 200 mL round bottom flask fitted with a condenser was put a stir bar and perylene monoanhydride[1] (1.83 g, 5.67 mmol). After adding 3-amino-1,2-propanediol (1.1 g, 2.1 mmol) and imidazole (14.3 g, 0.21 mol), the vessel was heated to 140° C. in an oil bath for 15 hours. The reaction was allowed to cool to room temperature and then 10% HCl was added (500 mL). The resulting deep red precipitate was collected by filtration, washed well with water and dried at 180° C. for several hours to yield 4 as a deep red solid (1.95 g, 86%).

N-(3-O-(4,4'-dimethoxytrityl-2-hydroxypropane) perylenemonoimide (5)

Into a dry 200 mL round bottom flask was put a stir bar. After purging the flask with nitrogen, dry pyridine (120 mL), compound 4 (0.44 g, 1.1 mmol), and dimethoxytritylchloride (0.45 g, 1.3 mmol) were all added, and the reaction was allowed to stir at room temperature for 48 hours. Several drops of methanol were then added, and the reaction was concentrated in vacuo to a viscous gum. The resulting gum was dissolved in $CH_2Cl_2$ (200 mL) and washed with sat. NaCl (200 mL). The aqueous layer was washed with in $CH_2Cl_2$ (3×100 mL). The combined organic layers were dried over $Na_2SO_4$ and concentrated in vacuo to a viscous gum. The isolated crude product wash then purified by silica gel column chromatography eluting with a gradient of $EtOAc:CH_2Cl_2$ (0:100 v/v)-(2:3 v/v) to give 5 as a red foam (0.25 g, 50%).

N-(3-O-(4,4'-dimethoxytrityl-2-O-(2-cyanoethyl-N, N-diisopropylamino phosphoramidite)perylenemonoimide (6)

Into a dry 50 mL round bottom flask was put a stir bar. After purging the flask with nitrogen, $CH_2Cl_2$ (5 mL) and compound 5 (0.25 g, 0.36 mmol) were added. N,N-diisopropylethylamine (0.24 mL, 1.79 mmol) and 2-cyanoethyl N,N-diisopropychlorophosphoramidite (0.16 mL, 0.72 mmol) were added via syringe. After 1 hour of stirring at room temperature, the reaction was determined to be complete by TLC analysis. The crude reaction mixture was then purified directly by silica gel column chromatography eluting with $CH_2Cl_2$:TEA (95:5 v/v) to give 6 as a dark red foam (0.26 g, 80%). The purified compound was analyzed by RP-HPLC with observation at 254 and 500 nm. Two diastereomers were found to be present.

Example 3

Synthesis of Oligomer Dyes

Oligomer dyes were synthesized on an Applied Biosystems 394 DNA/RNA synthesizer or on GE AKTÄ 10 OligoPilot on either 1 µmol or 10 µmol scales and possessed a 3'-phosphate group. Dyes were synthesized directly on CPG beads or on polystyrene solid support. The dyes were synthesized in the 3' to 5' direction by standard solid phase DNA methods. Coupling methods employed standard β-cyanoethyl phosphoramidite chemistry conditions. All phosphoramidite monomers were dissolved in acetonitrile/dichloromethane (0.1 M solutions), and were added in successive order using the following synthesis cycles: 1) removal of the 5'-dimethoxytrityl protecting group with dichloroacetic acid in toluene, 2) coupling of the next phosphoramidite with activator reagent in acetonitrile, 3) oxidation with iodine/pyridine/water, and 4) capping with acetic anhydride/1-methylimidizole/acetonitrile. The synthesis cycle was repeated until the 5' Oligofloroside was assembled. At the end of the chain assembly, the monomethoxytrityl (MMT) group or dimthoxytrityl (DMT) group was removed with dichloroacetic acid in dichloromethane or dichloroacetic acid in toluene. The dyes were cleaved from the solid support using concentrated aqueous ammonium hydroxide at room temperature for 2-4 hours. The product was concentrated in vacuo and Sephadex G-25 columns were used to isolate the main product which was analyzed by RP-HPLC. Sequences, of representative oligomers prepared according to the general method, as well as spectral properties and molecular weights (MW) determined by electrospray mass spectrometry are presented in Table 1.

TABLE 1

Representative Oligomer Dyes and Their Observed Masses and Optical Properties

| Sequence | Calculated Mass | Observed Mass | $\lambda_{max}$ (Exc.) nm | $\lambda_{max}$ (Em.) nm |
|---|---|---|---|---|
| 5'-$FC_SF$-3' | 1277.2 | 1276.8 | 492 | 519 |
| 5'-$C_SC_SC_SYYY$-3' | 1447.2 | 1447.5 | 330, 344 | 376, 395, 481 |
| 5'-$IC_SC_S$-3' | 777.2 | 777.6 | 263, 494 | 581 |
| 5'-$C_SC_SIC_SC_S$-3' | 1024.4 | 1024.4 | 263, 490 | 581 |
| 5'-amino-$C_S$ $C_SIC_SC_S$-3' | 1191.5 | 1192.9 | 263, 494 | 581 |
| 5'-$IC_SC_SC_S$ $C_SC_SC_S$-3' | 1271.6 | 1272.9 | 263, 494 | 581 |
| 5'-$EC_SC_S[SS]$ $C_SC_SE$-3' | 1648.8 | 1648.8 | 418, 446 | 453, 482 |
| 5'-Y-3' | 370.8 | 371.2 | 326, 342 | 377, 397 |
| 5'-YY-3' | 723.6 | 723.5 | 327, 343 | 376, 396, 484 |
| 5'-YYYY-3' | 1429.2 | 1429.2 | 328, 343 | 376, 397, 478 |
| 5'-YYYYY-3' | 1782.0 | 1783.9 | 328, 344 | 376, 397, 478 |
| 5'-YYYYYY-3' | 2134.8 | 2132.0 | 328, 344 | 376, 397, 478 |
| 5'-$YT_hYT_hY$-3' | 1688.8 | 1688.9 | 328, 344 | 376, 397, 484 |
| 5'-$YT_hT_hYT_h$ $T_hY$-3' | 2301.2 | 2303.6 | 328, 344 | 376, 397, 486 |
| 5'-$YT_hT_hT_h$ $YT_hT_hT_hY$-3' | 2913.6 | 2917.1 | 328, 344 | 377, 396, 485 |

TABLE 1-continued

Representative Oligomer Dyes and Their
Observed Masses and Optical Properties

| Sequence | Calculated Mass | Observed Mass | $\lambda_{max}$ (Exc.) nm | $\lambda_{max}$ (Em.) nm |
|---|---|---|---|---|
| 5'-YAYAY-3' | 1702.8 | 1703.1 | 328, 344 | 377, 396, 485 |
| 5'-YAAA-3' | 1310.4 | 1311.0 | 327, 343 | 377, 397 |
| 5'-YAAAYAA A-3' | 2602.8 | 2604.8 | 329, 346 | 377, 397 |
| 5'-YAAAAYA AAAY-3' | 3582.0 | 3581.0 | 329, 345 | 378, 399 |
| 5'-YAAAAAY AAAAY-3' | 4208.4 | 4208.0 | 329, 345 | 378, 398 |
| 5'-YAAAYAA AYAAAY-3' | 4248.0 | 4247.0 | 329, 345 | 378, 398 |

Structures for the above sequences are illustrated herein above.

All of the U.S. patents, U.S. patent application publications, U.S. patent applications, foreign patents, foreign patent applications and non-patent publications referred to in this specification, including but limited to U.S. Patent Application No. 61/868,973, filed Aug. 22, 2013, are incorporated herein by reference, in their entirety to the extent not inconsistent with the present description.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A compound having the following structure (III):

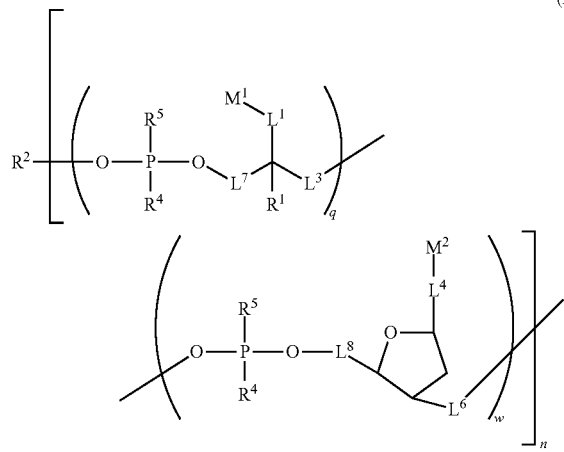

(III)

wherein:
M¹ and M² are, at each occurrence, independently a moiety comprising two or more double bonds and at least one degree of conjugation, and at least one occurrence of M¹ is a moiety comprising three or more aryl or heteroaryl rings, or combinations thereof;

L¹, L³, L⁴ L⁶, L⁷ and L⁸ are, at each occurrence, independently optional alkylene or heteroalkylene linkers;

R¹ is, at each occurrence, independently H, alkyl or alkoxy;

R² is an electron pair, H, alkyl, alkylether, hydroxyalkyl, aminoalkyl, hydroxylalkylether, sulfhydrylalkyl, sulfyhdrylalkylether, cyanoalkyl, phospho, thiophospho, alkylphospho, alkylthiophospho, alkyletherphospho, alkyletherthiophospho, phosphoalkyl, phosphoalkylether, thiophosphoalkyl or thiophosphoalkylether, or R² is a linker comprising a covalent bond to a biomolecule or microparticle;

R³ is H, OH, SH, —NH₂, alkyl, alkylether, hydroxyalkyl, aminoalkyl, hydroxylalkylether, sulfhydrylalkyl, sulfyhdrylalkylether, cyanoalkyl, —Oaralkyl, phosphate, thiophosphate, alkylphospho, alkylthiophospho, —Oalkylphospho, —Oalkylthiophospho, alkyletherphospho, alkyletherthiophospho, —Oalkyletherphospho, —Oalkyletherthiophospho phosphoalkyl, phosphoalkylether, thiophosphoalkyl, thiophosphoalkylether, —Ophosphoalkyl, O-phosphoalkylether, —Othiophosphoalkyl or —Othiophosphoalkylether;

R⁴ is, at each occurrence, independently O⁻, S⁻, OZ, SZ or N(R⁶)₂, where Z is a cation and each R⁶ is independently H or alkyl;

R⁵ is, at each occurrence, independently oxo, thioxo or absent;

n is an integer from 2 to 20; and q and w are each independently 0 or 1 for each integral value of n, wherein q is 1 for at least two integral values of n, or wherein q and w are each independently one for at least one integral value of n.

2. The compound of claim 1, wherein the compound has the following structure (IIa):

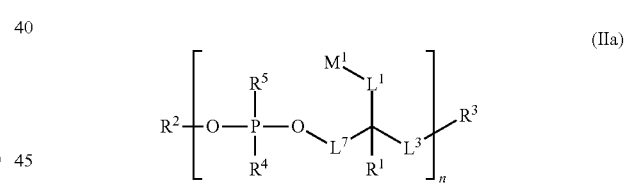

(IIa)

wherein:
M¹ is, at each occurrence, independently a moiety comprising two or more double bonds and at least one degree of conjugation, and at least one occurrence of M¹ is a moiety comprising four or more aryl or heteroaryl rings, or combinations thereof;

L¹, L⁷ and L³ are, at each occurrence, independently optional alkylene or heteroalkylene linkers;

R¹ is, at each occurrence, independently H, alkyl or alkoxy;

R² is H, alkyl, alkylether, hydroxyalkyl, aminoalkyl, hydroxylalkylether, sulfhydrylalkyl, sulfyhdrylalkylether, cyanoalkyl, phospho, thiophospho, alkylphospho, alkylthiophospho, alkyletherphospho, alkyletherthiophospho, phosphoalkyl, phosphoalkylether, thiophosphoalkyl or thiophosphoalkylether, or R² is a linker comprising a covalent bond to a biomolecule or microparticle;

R³ is H, OH, SH, —NH₂, alkyl, alkylether, hydroxyalkyl, aminoalkyl, hydroxylalkylether, sulfhydrylalkyl, sulfyhdrylalkylether, cyanoalkyl, —Oaralkyl, phosphate, thiophosphate, alkylphospho, alkylthiophospho, —Oalkylphospho, —Oalkylthiophospho, alkyletherphospho, alkyletherthiophospho, —Oalkyletherphospho, —Oalkyletherthiophospho phosphoalkyl, phosphoalkylether, thiophosphoalkyl, thiophosphoalkylether, —Ophosphoalkyl, O-phosphoalkylether, —Othiophosphoalkyl or —Othiophosphoalkylether;

$R^4$ is, at each occurrence, independently $O^-$, $S^-$, OZ, SZ or $N(R^6)_2$, where Z is a cation and each $R^6$ is independently H or alkyl;

$R^5$ is, at each occurrence, independently oxo, thioxo or absent; and n is an integer from 2 to 10.

3. The compound of claim 1, wherein the compound has one of the following structures (IIc), (IId), (IIe) or (IIf):

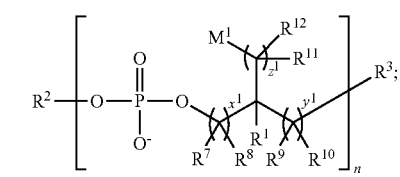
(IIc)

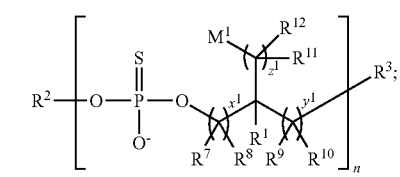
(IId)

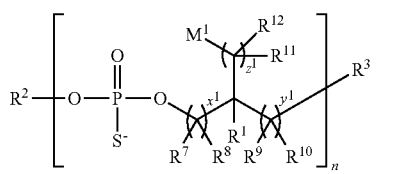
(IIe)

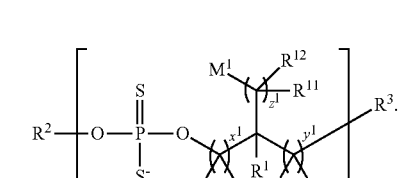
(IIf)

4. The compound of claim 1, wherein the compound has the following structure (IIIb):

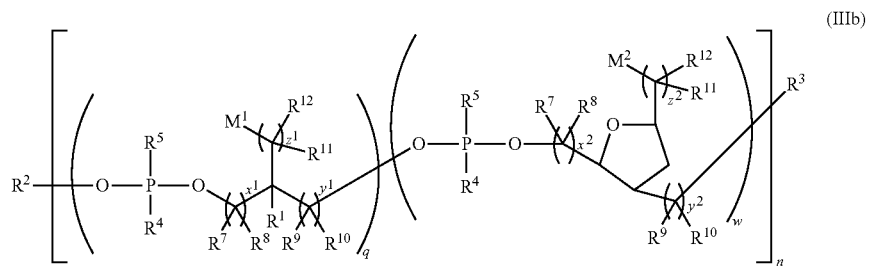
(IIIb)

wherein:

$R^7$, $R^8$, $R^9$, $R^{10}$, $R^{11}$ and $R^{12}$ are, at each occurrence, independently H or alkyl; and $x^1$, $x^2$, $y^1$, $y^2$, $z^1$ and $z^2$ are, at each occurrence, independently an integer from 0 to 5.

5. The compound of claim 1, wherein $R^2$ has one of the following structures:

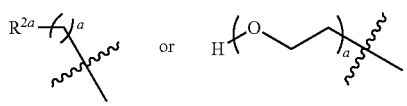

wherein:

$R^{2a}$ is —OH, —$NH_2$, or —SH; and a is an integer from 1 to 10.

6. The compound of claim 1, wherein $R^2$ has one of the following structures:

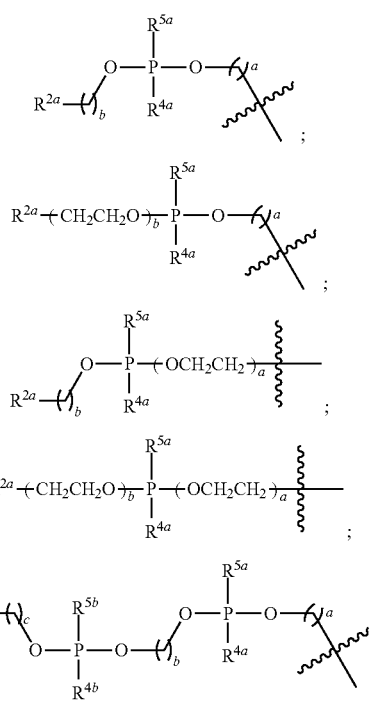

-continued

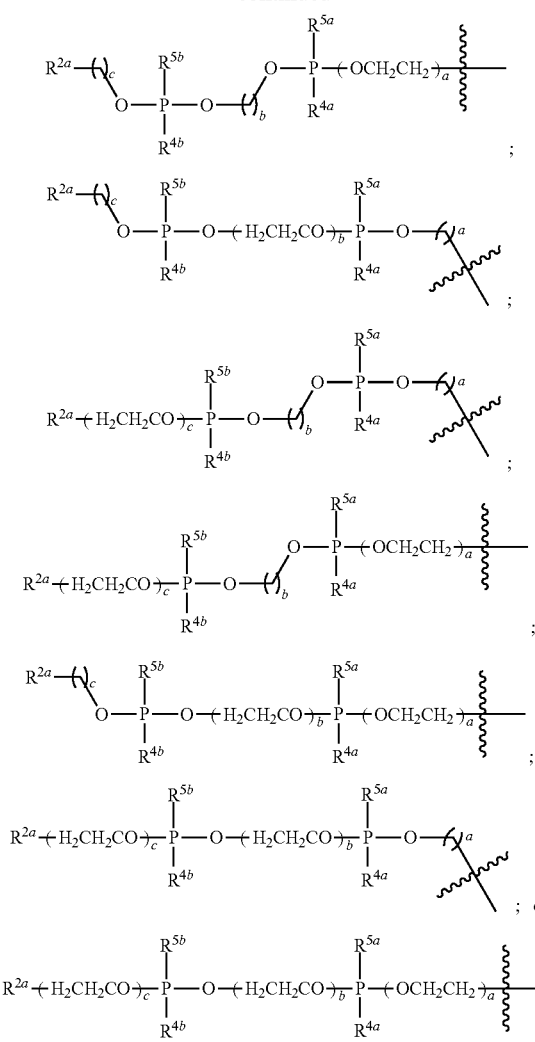

wherein:
R$^{2a}$ is —OH, —SH, —NH$_2$, phosphate or thiophosphate;
R$^{4a}$ and R$^{4b}$ are independently O$^-$, S$^-$, OZ or SZ, where Z is a cation;
R$^{5a}$ and R$^{5b}$ are independently oxo, or thioxo; and
a, b and c are each independently integers from 1 to 10.

7. The compound of claim 1, wherein R$^3$ is OH.

8. The compound of claim 1, wherein R$^3$ has one of the following structures:

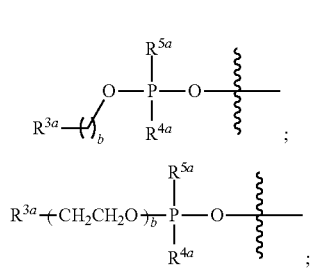

-continued

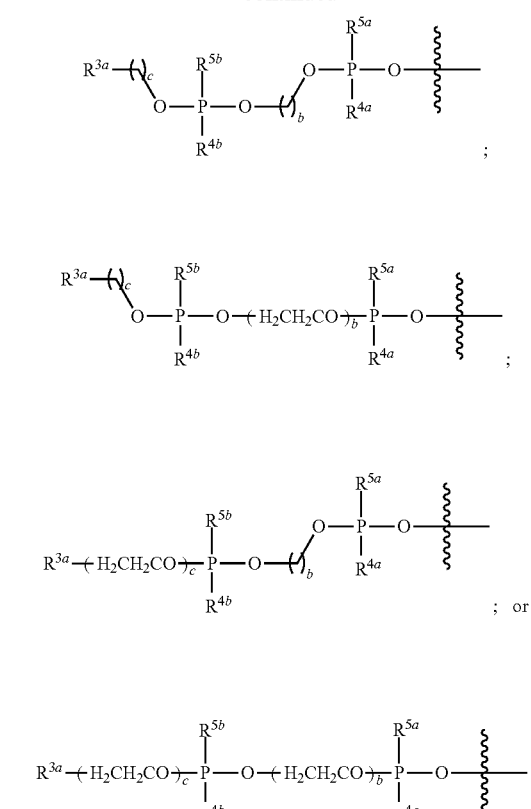

wherein:
R$^{3a}$ is —OH, —SH, —NH$_2$, phosphate or thiophosphate;
R$^{4a}$ and R$^{4b}$ are independently O$^-$, S$^-$, OZ or SZ, where Z is a cation;
R$^{5a}$ and R$^{5b}$ are independently oxo, or thioxo; and
b and c are each independently integers from 1 to 10.

9. The compound of claim 1, wherein at least one M$^1$ is a moiety comprising four or more aryl or heteroaryl rings, or combinations thereof.

10. The compound of claim 1, wherein M$^1$ is, at each occurrence, independently fluorescent or colored.

11. The compound of claim 1, wherein M$^1$ has one of the following structures:

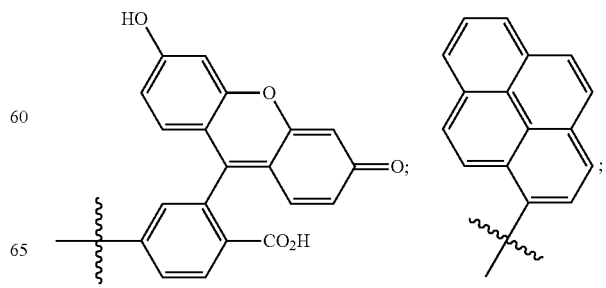

61
-continued

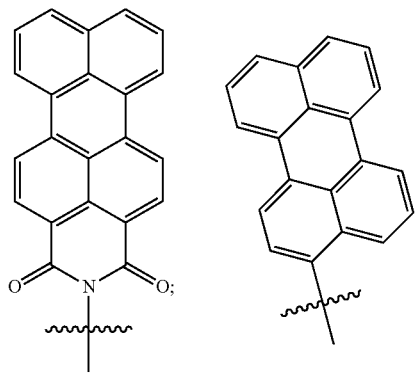

62
-continued

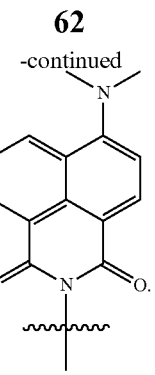

12. The compound of claim 1, wherein $R^2$ is a linker comprising a covalent bond to a biomolecule or microparticle, and $R^3$ is H, OH, phosphate, thiophosphate, phosphoalkyl, —Ophosphoalkyl, phosphoalkylether, —Ophosphoalkylether, thiophosphoalkyl, —Othiophospho, thiophosphoalkylether or —Othiophosphoalkylether.

13. A compound having one of the following structures:

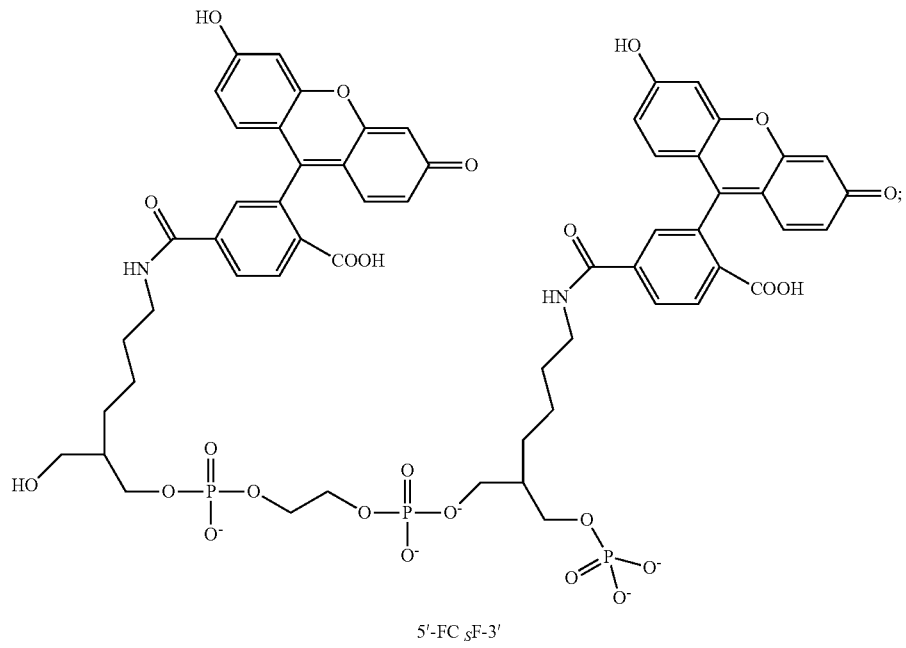

5'-FC $_s$F-3'

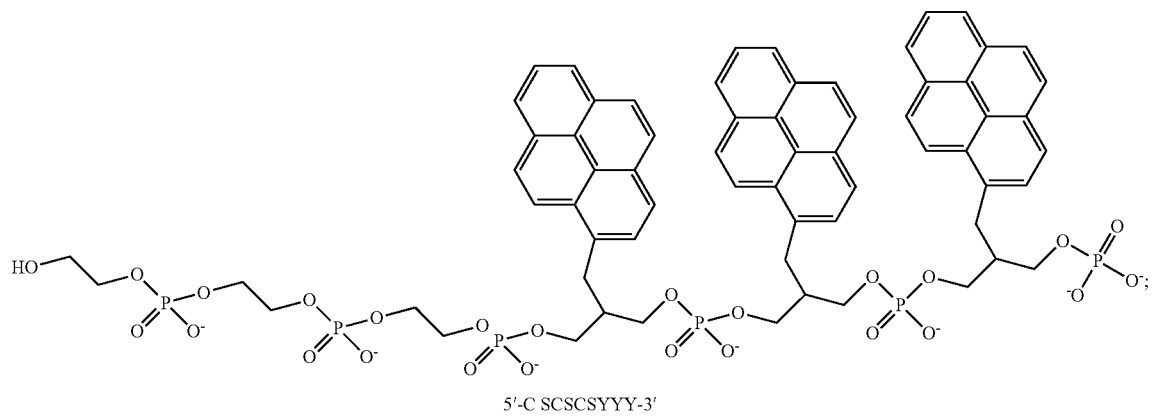

5'-C SCSCSYYY-3'

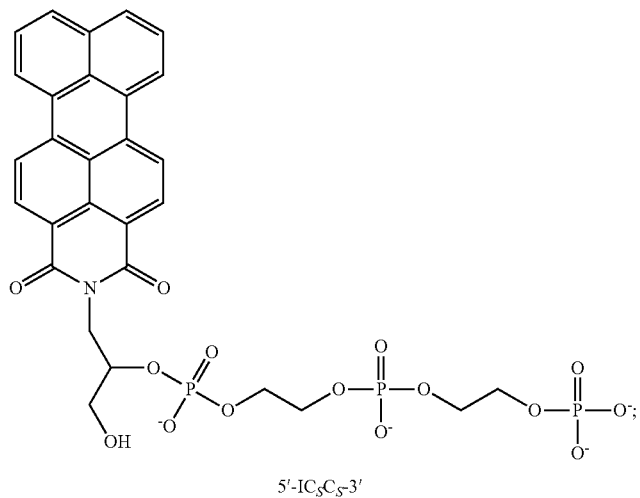
5'-IC$_S$C$_S$-3'
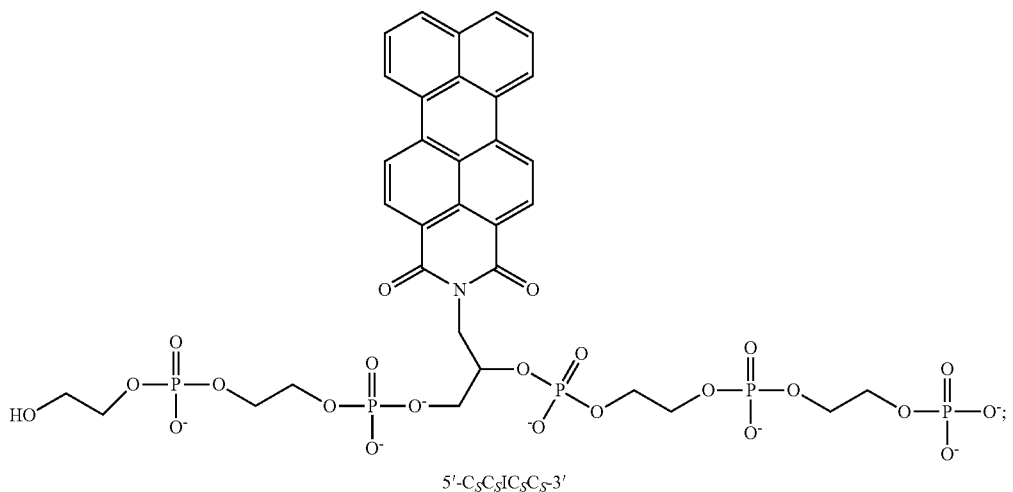
5'-C$_S$C$_S$IC$_S$C$_S$-3'
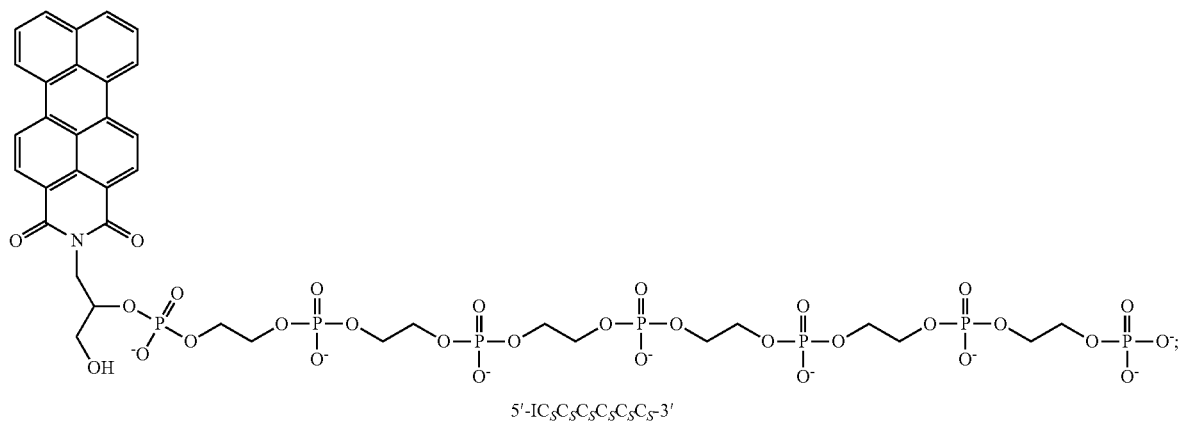
5'-IC$_S$C$_S$C$_S$C$_S$C$_S$C$_S$-3'

-continued
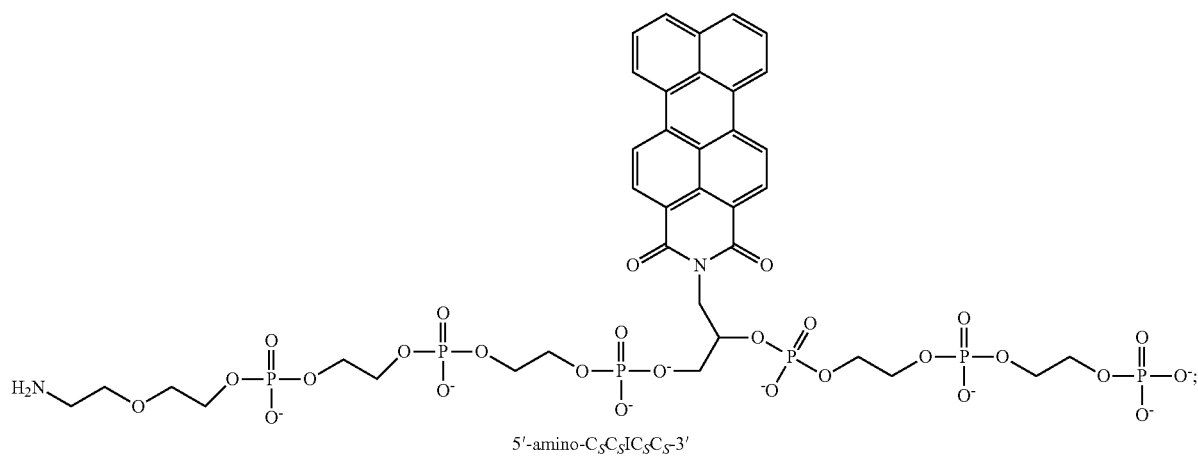
5'-amino-C₅C₅IC₅C₅-3'
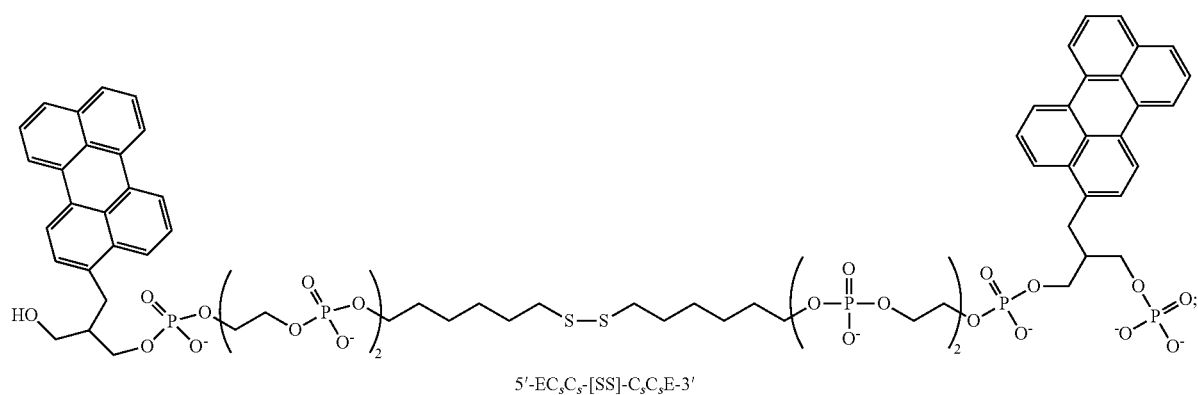
5'-EC₅C₅-[SS]-C₅C₅E-3'
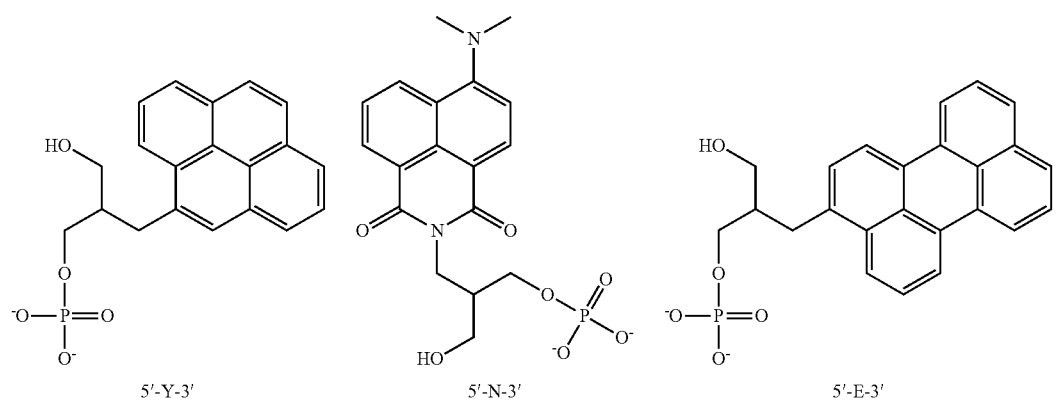
5'-Y-3'　　5'-N-3'　　5'-E-3'

67
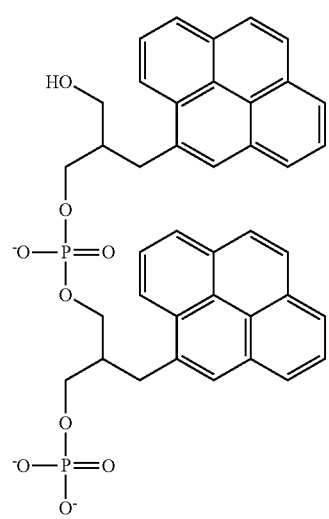
5'-YY-3'
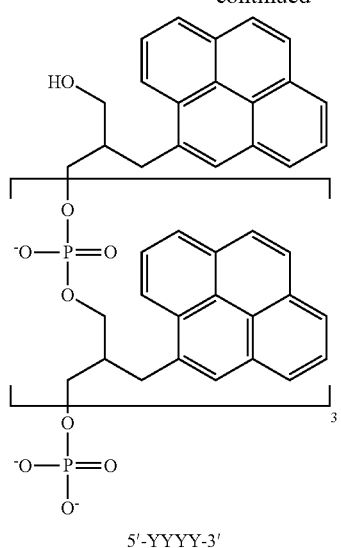
5'-YYYY-3'
68
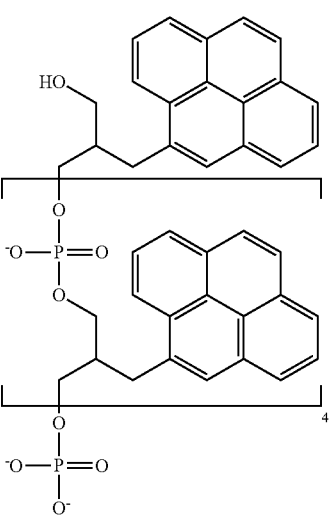
5'-YYYYY-3'
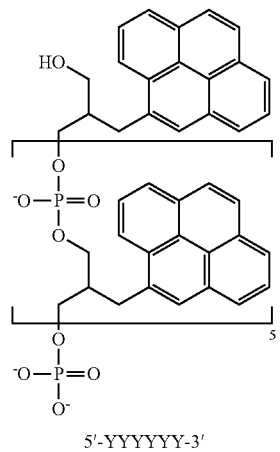
5'-YYYYYY-3'
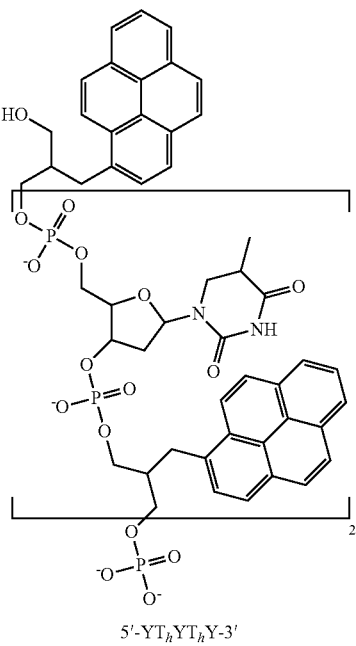
5'-YT$_h$YT$_h$Y-3'
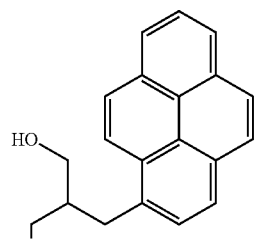
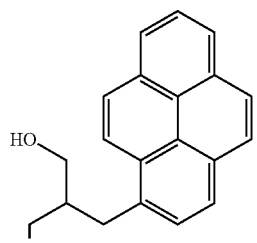

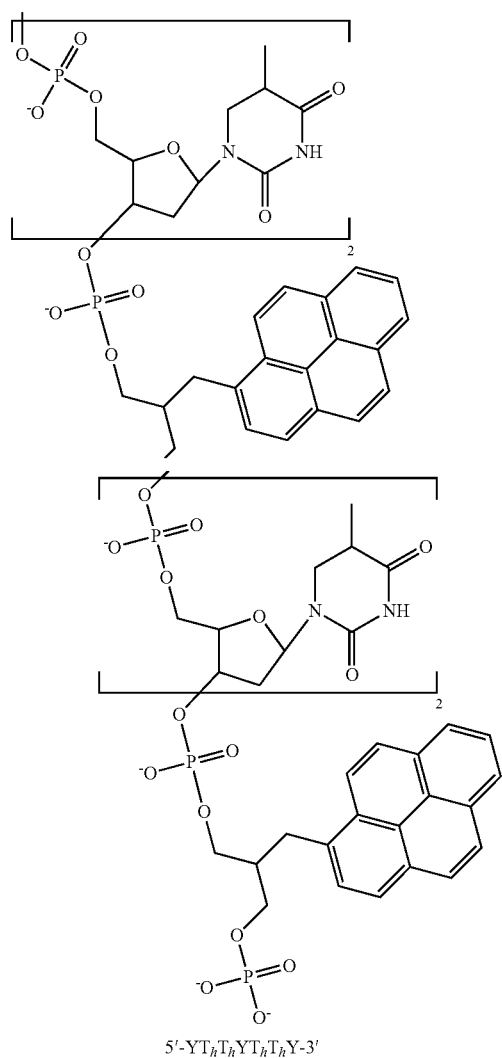
5'-YT$_h$T$_h$YT$_h$T$_h$Y-3'
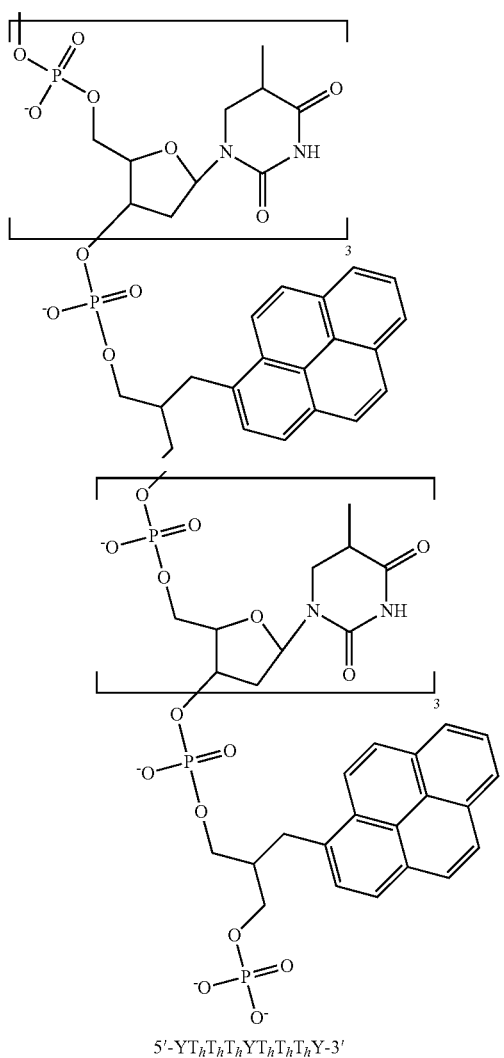
5'-YT$_h$T$_h$T$_h$YT$_h$T$_h$T$_h$Y-3'
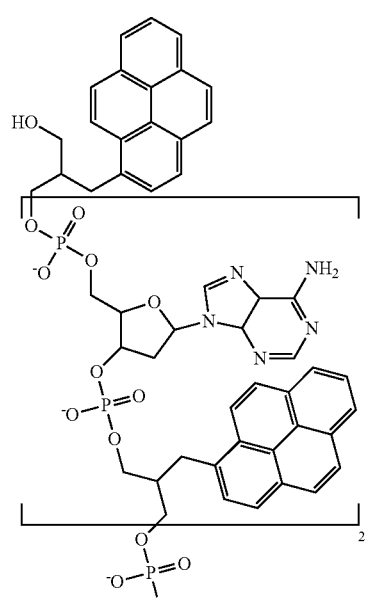
5'-YAYAY-3'
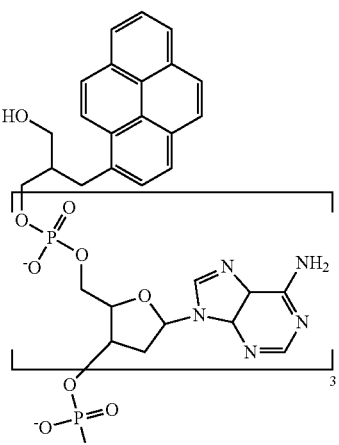
5'-YAAA-3'

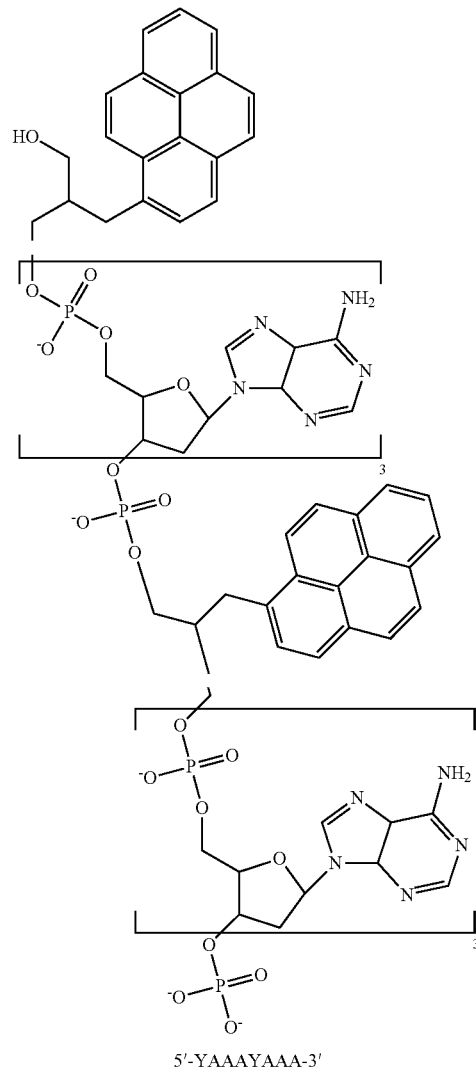
5'-YAAAYAAA-3'
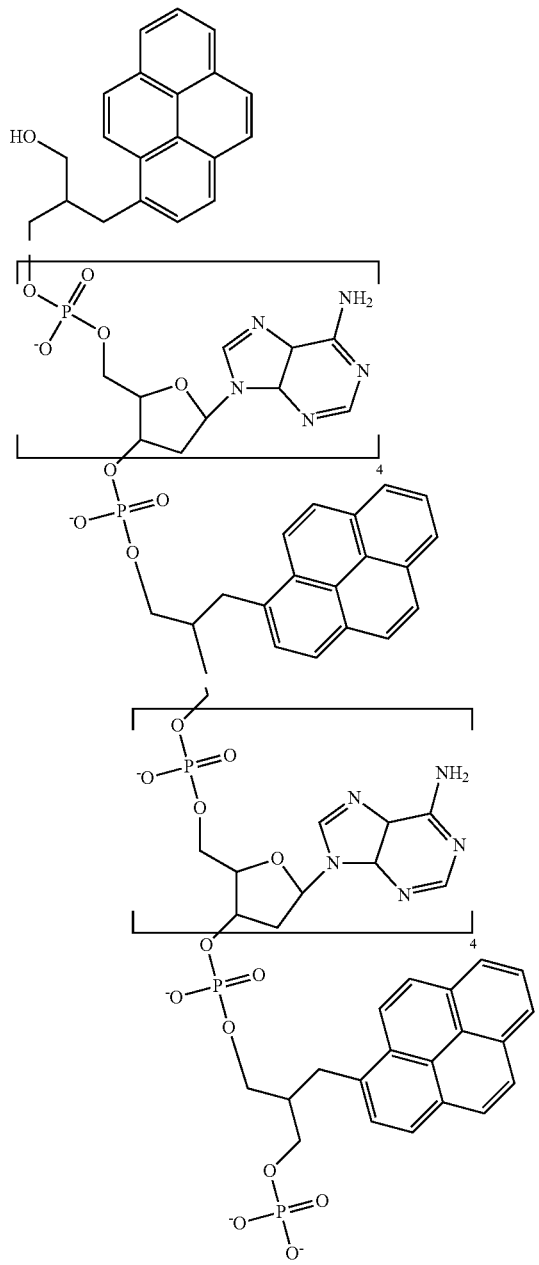
5'-YAAAAYAAAA-3'

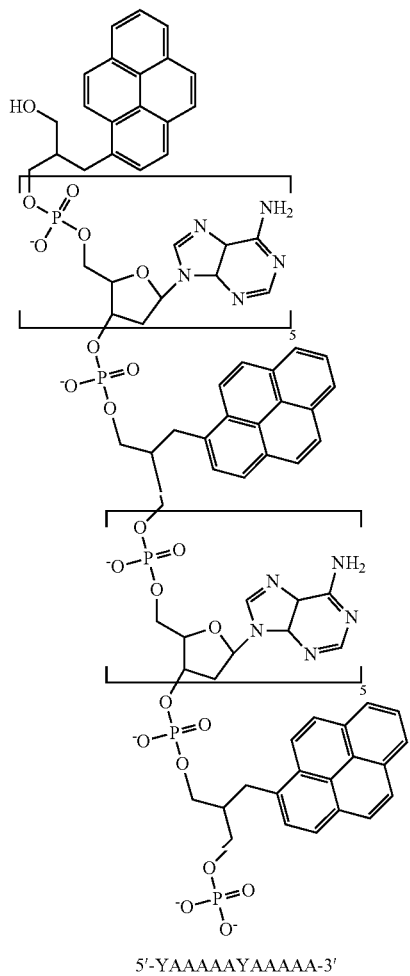

5'-YAAAAAYAAAAA-3'

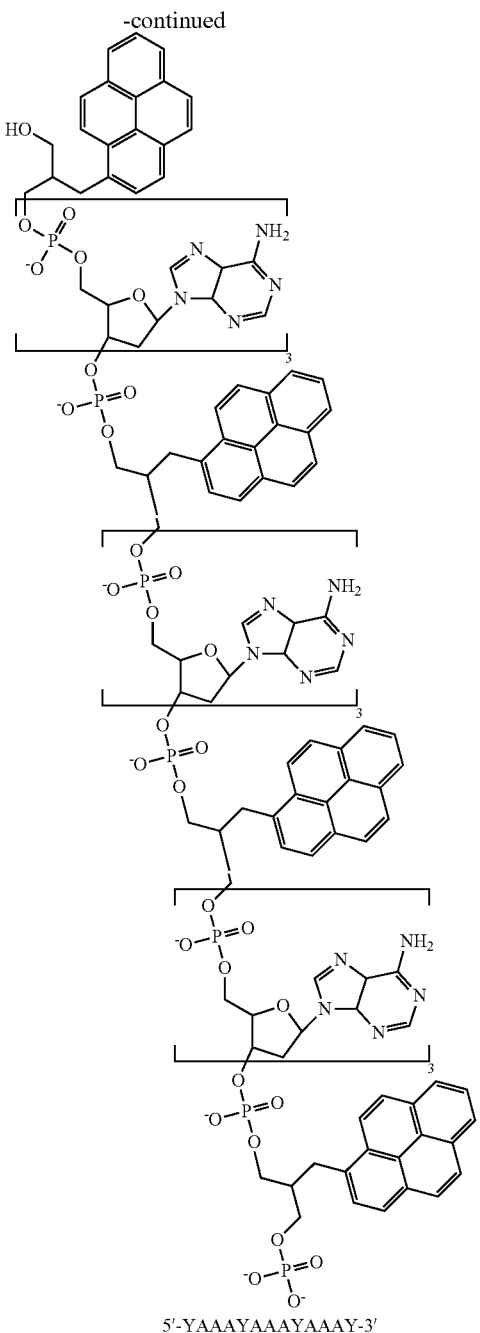

5'-YAAAYAAAYAAAY-3'

14. A method of staining a sample, comprising adding to said sample the compound of claim 12 in an amount sufficient to produce an optical response when said sample is illuminated at an appropriate wavelength.

15. A method for visually detecting a biomolecule, the method comprising:
(a) providing the compound of claim 12; and
(b) detecting the compound by its visible properties.

16. A method for visually detecting a biomolecule, the method comprising:
(a) admixing the compound of claim 1 with one or more biomolecules; and
(b) detecting the compound by its visible properties.

17. A composition comprising the compound of claim 1 and one or more biomolecules.

18. The compound of claim 1, wherein $R^2$ is hydroxylalkyl, aminoalkyl, hydroxylalkylether, sulfhydrylalkyl or sulfhydrylalkylether.

19. The compound of claim 1, wherein $R^2$ is alkylphospho, alkylthiophospho, alkyletherphospho, alkyletherthiophospho, phosphoalkyl, phosphoalkylether, thiophosphoalkyl or thiophosphoalkylether, wherein $R^2$ is optionally substituted with a substituent selected from —OH, —NH$_2$, and —SH.

20. The compound of claim 1, wherein $R^3$ is, phosphate, thiophosphate, phospho, thiophospho, —Oalkylphospho, —Oalkylthiophospho, —Oalkyletherphospho, —Oalkyletherthiophospho, —Ophosphoalkyl, —Ophosphoalkylether, —Othiophosphoalkyl or —Othiophosphoalkylether optionally substituted with a substituent selected from —OH, —NH$_2$, and —SH.

21. The compound of claim 1, wherein n is an integer from 2 to 15.

22. The compound of claim 1, wherein each M$^1$ is pyrene, perylene, perylene monoimide or 6-FAM or derivative thereof.

23. The compound of claim 1, wherein R$^2$ is a linker comprising a covalent bond to a biomolecule.

24. The compound of claim 23, wherein the biomolecule is an enzyme, receptor, receptor ligand, antibody, glycoprotein, aptamer or prion.

25. The method of claim 14, wherein said optical response is a fluorescent response.

26. The method of claim 14, wherein said sample comprises cells.

27. The method of claim 26, further comprising observing said cells by flow cytometry.

* * * * *

UNITED STATES PATENT AND TRADEMARK OFFICE
CERTIFICATE OF CORRECTION

PATENT NO. : 9,765,220 B2  
APPLICATION NO. : 14/913675  
DATED : September 19, 2017  
INVENTOR(S) : Tracy Matray et al.

Page 1 of 6

It is certified that error appears in the above-identified patent and that said Letters Patent is hereby corrected as shown below:

Column 69:

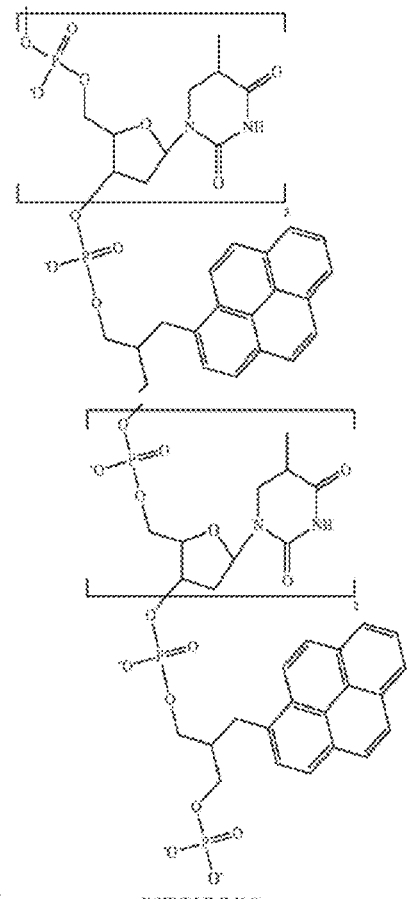
"         " should read, --

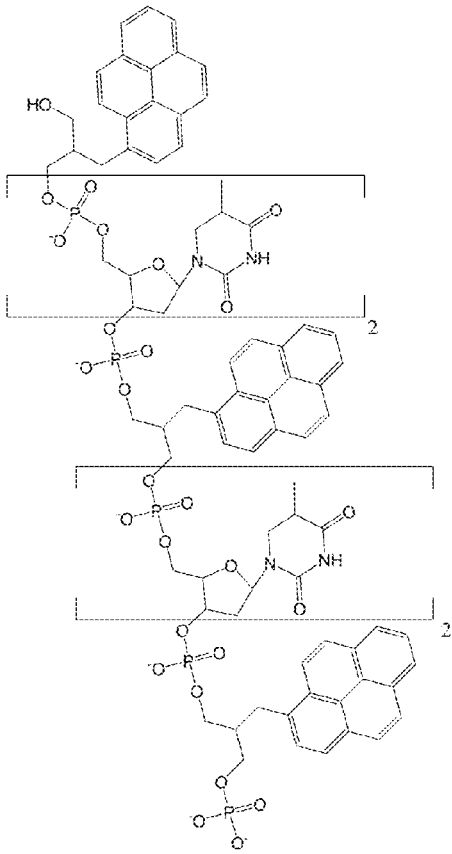
5'-YT$_h$T$_h$YT$_h$T$_h$Y-3'    --.

Signed and Sealed this  
Eighth Day of May, 2018

Andrei Iancu  
*Director of the United States Patent and Trademark Office*

CERTIFICATE OF CORRECTION (continued)
U.S. Pat. No. 9,765,220 B2

Column 70:

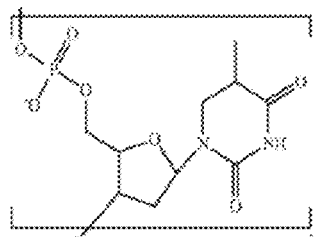
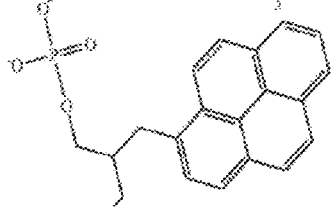
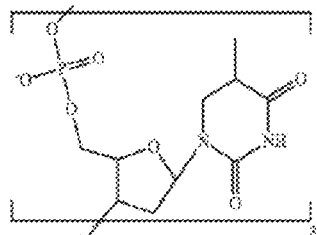
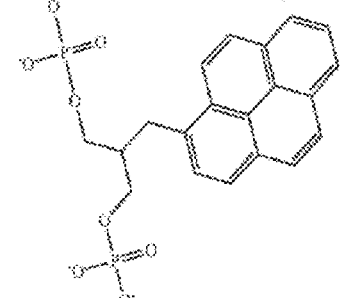

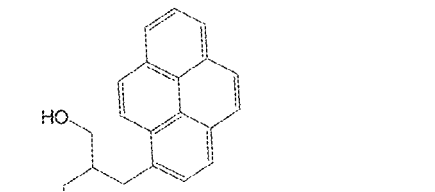
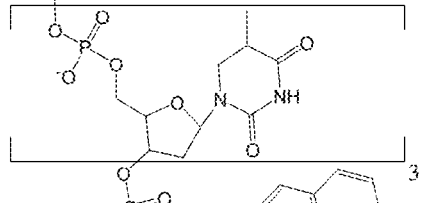
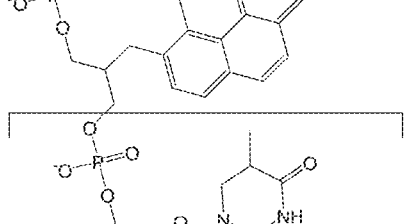
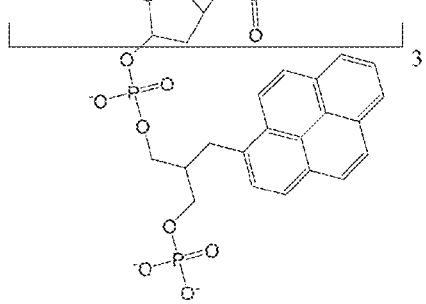

" " should read, -- 5'-YT$_h$T$_h$T$_h$YT$_h$T$_h$T$_h$Y-3' --.

Column 71:
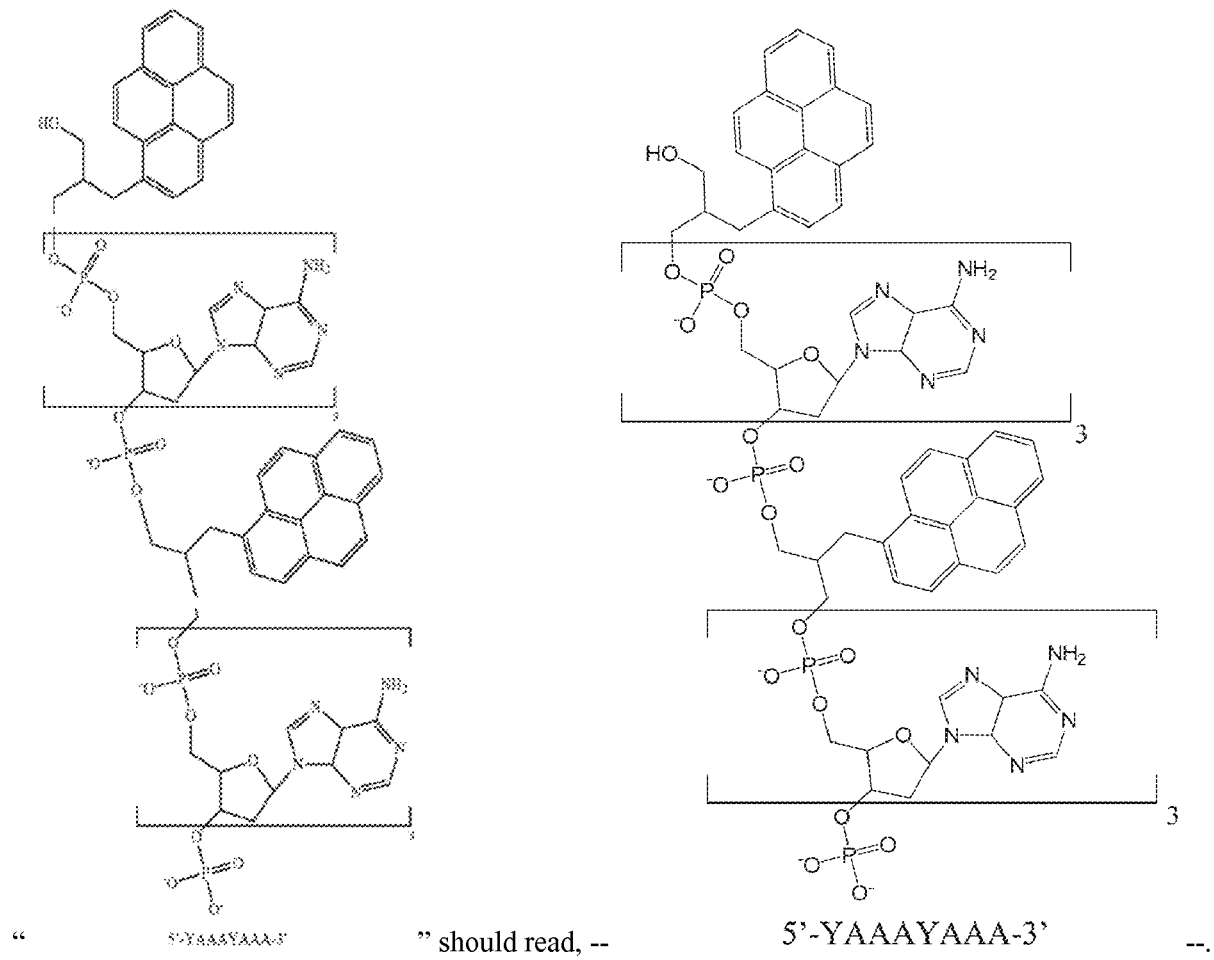

CERTIFICATE OF CORRECTION (continued)
U.S. Pat. No. 9,765,220 B2

Column 72:

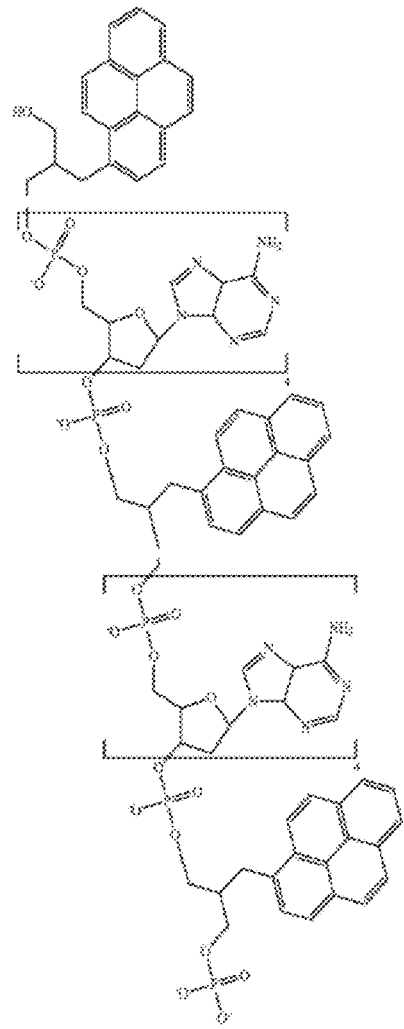 " should read, -- 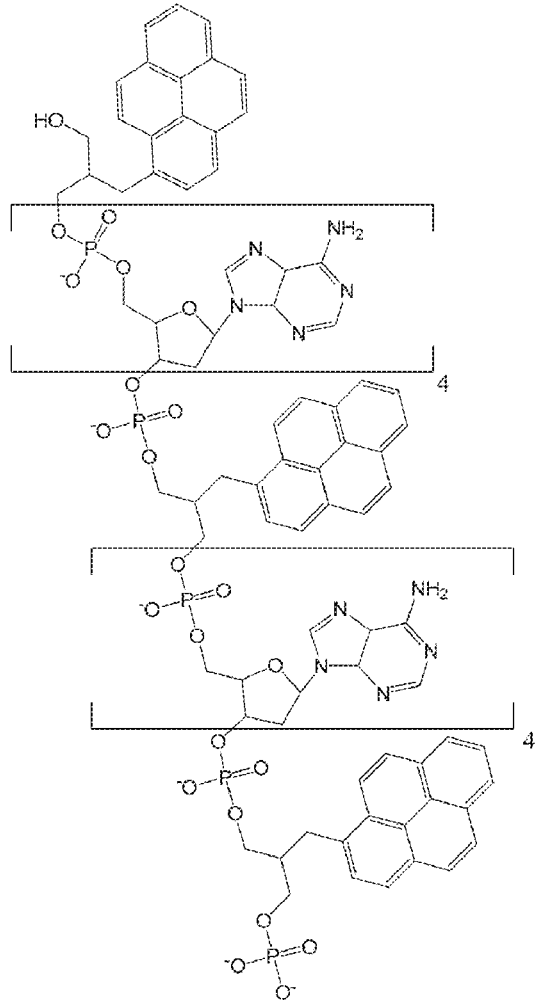 5'-YAAAAYAAAAY-3' --.

CERTIFICATE OF CORRECTION (continued)
U.S. Pat. No. 9,765,220 B2

Column 73:

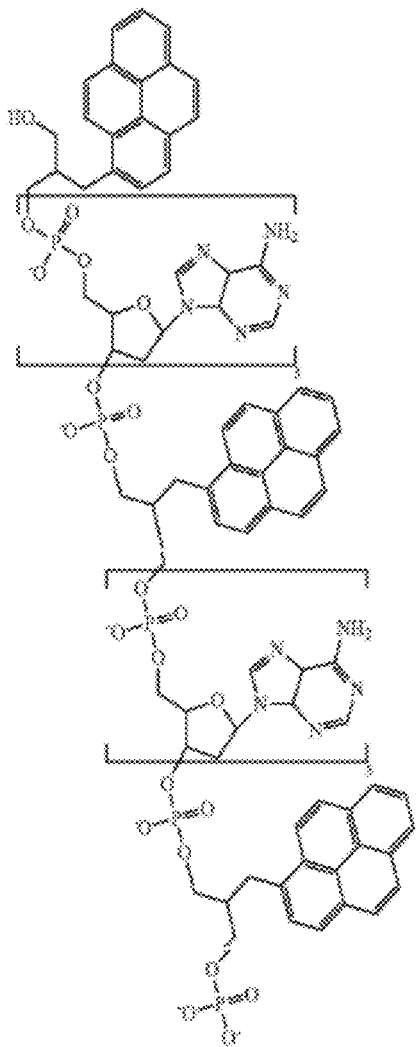 " 5'-YAAAAAYAAAAA-3' " should read, -- 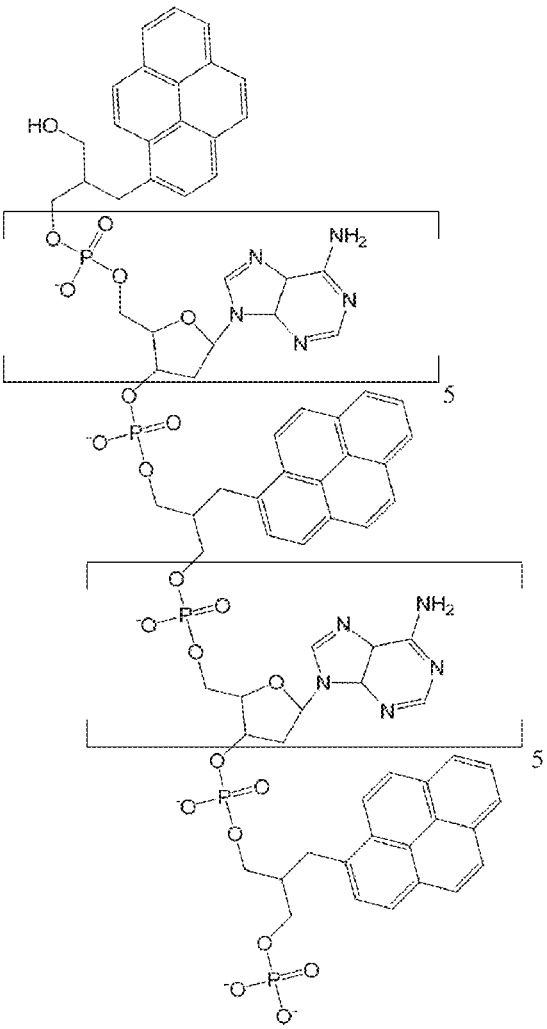 5'-YAAAAAYAAAAAY-3' --.

CERTIFICATE OF CORRECTION (continued)
U.S. Pat. No. 9,765,220 B2

Column 74:

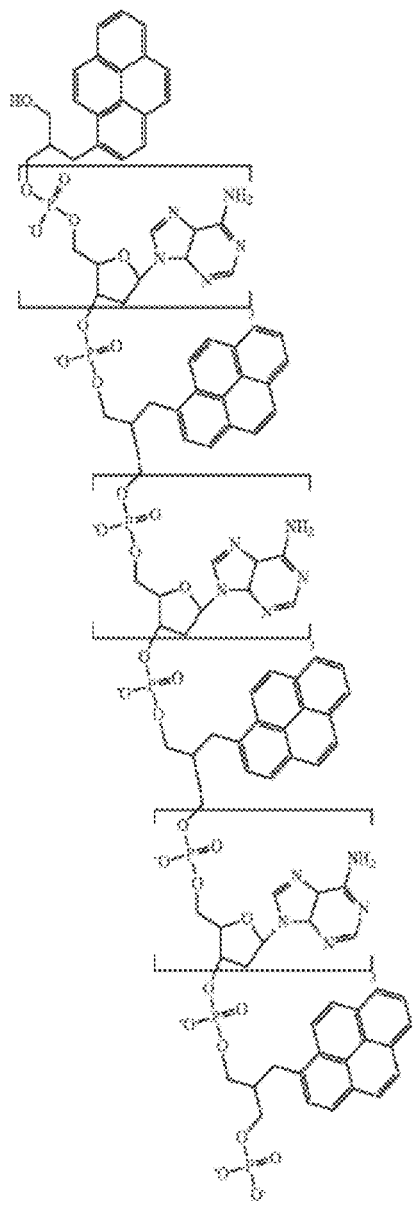 " should read, -- 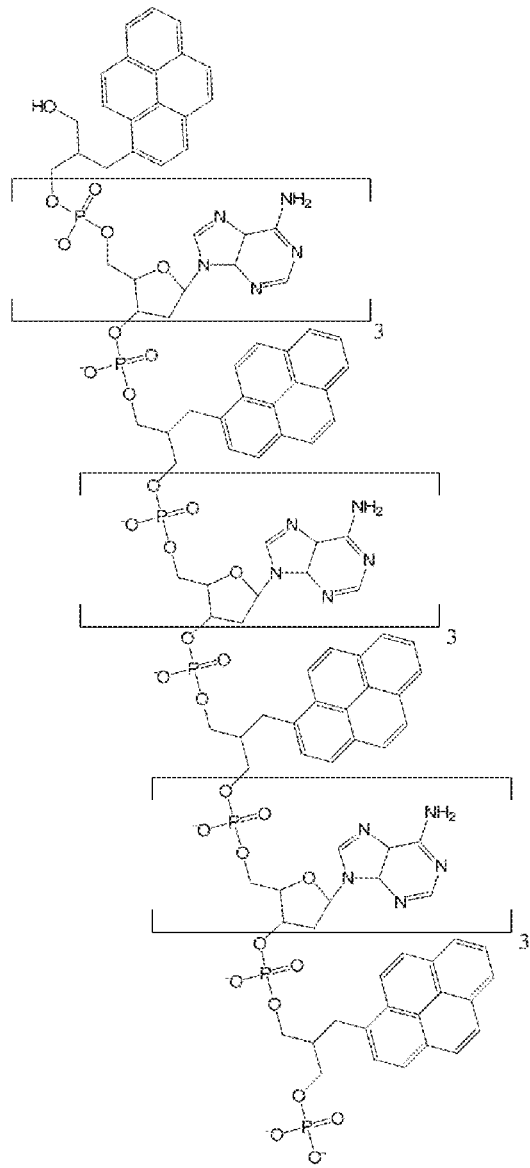 5'-YAAAYAAAYAAAY-3' --.